US005886163A

United States Patent [19]
Hasel et al.

[11] Patent Number: 5,886,163
[45] Date of Patent: Mar. 23, 1999

[54] HIV-1 ANTIGENS, ANTIBODY COMPOSITIONS RELATED THERETO, AND THERAPEUTIC AND PROPHYLACTIC USES THEREOF

[75] Inventors: Karl W. Hasel, Encinitas, Calif.; Paul J. Maddon, New York, N.Y.

[73] Assignee: Progenics Pharmaceuticals, Inc., Tarrytown, N.Y.

[21] Appl. No.: 530,146

[22] PCT Filed: Mar. 25, 1994

[86] PCT No.: PCT/US94/03282

§ 371 Date: Dec. 22, 1995

§ 102(e) Date: Dec. 22, 1995

[87] PCT Pub. No.: WO94/22477

PCT Pub. Date: Oct. 13, 1994

Related U.S. Application Data

[63] Continuation of Ser. No. 37,816, Mar. 26, 1993.
[51] Int. Cl.$^6$ ............... C07H 21/02; C07K 1/00; C07K 14/00; A61K 39/21
[52] U.S. Cl. ............ 536/23.1; 424/188.1; 424/184.1; 424/208.1; 424/204.1; 530/350; 530/395
[58] Field of Search ............ 424/188.1, 208.1, 424/184.1, 204.1; 435/69.3; 536/23.1; 530/350

[56] References Cited

U.S. PATENT DOCUMENTS 5,030,449  7/1991  Berzofsky et al. .................. 424/88

FOREIGN PATENT DOCUMENTS

WO9111461  8/1991  WIPO.
WO9115512  10/1991 WIPO.

OTHER PUBLICATIONS

Lasky, et al. (1987) Cell 50: 975–985.
Letvin (1993) NEJM 329(19): 1400–1405.
Travis, et al. (1992) Virology, 186: 313–317.
Fox (1994) Biotechnology 12: 128.
Greene (1993) Scientific American, Sep. 1993, 99–105.
Haynes (1993) Science 200: 1279–1286.
Brown (1993) "AIDS Vaccine Trials Viewed with Caution", The Washington Post Newspaper, Jun. 10, 1993.
Chiou, S–H., et al. (1992) J. of Cellular Biochem., Supplement 16E, p. 18.
Cohen (1993) Science 262: 980–981.
Bolognesi, D.P. (1990) TIBTech 8: 40–45 (Exhibit 4).
Cohn, E.J. et al., (1994) J. Clin. Invest. 23: 417–432 (Exhibit 5).
Steimer, K.S., et al. (1991) AIDS 5: S135–143 (Exhibit 6).
Steimer, K.S., et al. (1991) Science 254: 105–108 (Exhibit 7).
Wain–Hobson, et al. (1991) Science 252: 961–965 (Exhibit 8).
Zolla–Pazner, S., et al (1992) Sem. In Virology 3: 203–211 (Exhibit 9).
Wyatt, et al, "Relationship of the Human Immuno . . . " Journal of Virology, 66(12): 6997–7004, 1992.
Thali, et al, "Discontinuous; Conserved Neutralization Epitopes Overlapping . . . " Journal of Virology, 1992.

Primary Examiner—Lynette F. Smith
Attorney, Agent, or Firm—John P. White; Cooper & Dunham LLP

[57] ABSTRACT

The subject invention provides a recombinant nucleic acid molecule which encodes a mutant HIV-1 gp120 envelope glycoprotein comprising a V3 loop deletion and a C4 domain$_{(W \to X)}$ point mutation wherein X is an amino acid residue other than tryptophan, and the HIV-1 gp120 envelope glycoprotein encoded thereby.

The subject invention further provides a method of obtaining partially purified antibodies which specifically bind to the CD4-binding domain of HIV-1 gp120 envelope glycoprotein, the partially purified antibodies produced thereby, and pharmaceutical compositions comprising same. Finally, the subject invention provides methods of treating HIV-1-infected subjects, and of reducing the likelihood of HIV-1-exposed and non-HIV-1-exposed subjects' becoming infected with HIV-1 using the pharmaceutical compositions of the subject invention.

9 Claims, 38 Drawing Sheets

FIGURE 3A

```
     HincII
  1  ttgacattgattattgactagttattaatagtaatcaattacgggtcattagttcatagcccatatatgga 73  gttccgcgttacataacttacggtaaatgcccgcctgacgcccaacgaccccgcccattgacgtc 145  aataatgacgtatgttcccatagtaacgccaatagggactttccattgacgtcaatgggtggactatttacg 217  gtaaactgcccacttggcagtacatcaagtgtatcatatgccaagtacgccccctattgacgtcaatgacgg 289  taaatgcccgcctggcattatgcccagtacatgaccttatgggactttcctacttggcagtacatctacgt 361  attagtcatcgctattaccatggtgatgcggttttggcagtacatcaatgggcgtggatagcggtttgactc 433  acggggatttccaagtctccaccccattgacgtcaatgggagtttgttttggcaccaaatcaacgggactt
```

FIGURE 3B

```
505   tccaaaatgtcgtaacaactccgccccattgacgcaaatgggcggtaggcgtgtacggtgggaggtctatat
                                                    Exon A
577   aagcagagctcgtttagtgaaccgTCAGATCGCCTGGAGACGCCATCCACGCTGTTTGACCTCCATAGAAG
                                ↑Transcription Start
649   ACACCGGGACCGATCCAGCCTCCGCGGGCCGGGAACGGTGCATTGGAACGCGGATTCCCCGTGCCAAGAGTGA
                                                    Intron A
721   Cgtaagtaccgcctatagactctataggcacaccccctttggctcttatgcatgctatactgttttggcttg 793   ggccaacacccgtcctagataggtgatggtatagcttagcctataggtgtgggttattgaccattattgac 865   cactcccctattggtgacgatactttccattactaatccataacatggccgctctttgccacaactatctct 937   attggctatatgccaatactctgtccttcagagactgacacgactctgtattttacaggatgggtccca 1009  tttattattacaaattcacatatacaacgccgtggctcttctccggtagcgcggagctccacatccgag 1081  ctccacgcgaatctcggtacgtgttccggacatggctcatggtcgctcggcagctccttgctcctaacagtggaggccag 1153  cctgtcccatgcccaccaccagtgtgccgcacaaggccgtggcggtagggtatgtgtctga 1225  acttaggcacaggacaatgccca
```

FIGURE 3C

```
1297  aaatgagctcggagattgggctcgcaccgctgacgcagatgaagactttaaggcagcggcagaagaagatgc
1369  aggcagctgagttgttgtattctgtagagttggaggtaactcccgttgcgttgctgttaacgtggagggca
1441  gtgtagtcgagcagtactcgttgctgccgcgccgcgccaccagacataatagctgacagactaacagactgt
                                                                tPA signal sequence
                  PstI              Exon B
1513  tcctttccatgggtctttctgcagTCACCGTCCTTGACACGATGGATGCAATGAAGAGAAGAGGGCTCTGCTGT
                                         M  D  A  M  K  R  R  G  L  C  C
                                                                              NarI
1585  GTGCTGCTGCTGTGTGGAGCAGTCTTCGTTTCGCCCAGCCAGGAAATCCATGCCCGATTCAGAAGAGGGCCGCC
   1   V  L  L  C  G  A  V  F  V  S  P  S  Q  E  I  H  A  R  F  R  R  G  A
1657  AGAACAGAAAAATTGTGGGTCACAGTCTATTATGGGTACCTGTGTGGAAGGAAGCAACCACCACTCTATTT
  35   R  T  E  K  L  W  V  T  V  Y  Y  G  V  P  V  W  K  E  A  T  T  T  L  F
              ▲ Signal cleavage
1729  TGTGCATCAGATGCTAAAGCATATGATACAGAGGTACATAATGTTTGGGCCACACATGCCTGTGTACCCACA
  59   C  A  S  D  A  K  A  Y  D  T  E  V  H  N  V  W  A  T  H  A  C  V  P  T
1801  GACCCCAACCCACAAGAAGTAGTATTGGTAAATGTGACAGAAAATTTTAACATGTGGAAAAATGACATGGTA
  83   D  P  N  P  Q  E  V  V  L  V  N  V  T  E  N  F  N  M  W  K  N  D  M  V
```

FIGURE 3D

```
1873  GAACAGATGCATGAGGATATAATCAGTTTATGGGATCAAAGCCTAAAGCCATGTGTAAAATTAACCCCACTC
 107   E  Q  M  H  E  D  I  I  S  L  W  D  Q  S  L  K  P  C  V  K  L  T  P  L

1945  TGTGTTAGTTTAAAGTGCACTGATTTGGGGAATGCTACTAATACCAATAGTAGTAATACCAATAGTAGTAGC
 131   C  V  S  L  K  C  T  D  L  G  N  A  T  N  T  N  S  S  N  T  N  S  S  S

2017  GGGGAAATGATGATGGAGAAAGGAGAGATAAAAAACTGCTCTTTCAATATCAGCACAAGCATAAGAGGTAAG
 155   G  E  M  M  M  E  K  G  E  I  K  N  C  S  F  N  I  S  T  S  I  R  G  K

2089  GTGCAGAAAGAATATGCATTTTTTTATAAACTTGATATAATACCAATAGATAATGATACTACCAGCTATACG
 179   V  Q  K  E  Y  A  F  F  Y  K  L  D  I  I  P  I  D  N  D  T  T  S  Y  T

2161  TTGACAAGTTGTAACACCTCAGTCATTACACAGGCCTGTCCAAAGGTATCCTTTGAGCCAATTCCCATACAT
 203   L  T  S  C  N  T  S  V  I  T  Q  A  C  P  K  V  S  F  E  P  I  P  I  H

2233  TATTGTGCCCCGGCTGGTTTTGCGATTCTAAAATGTAATAATAGACGTTCAATGGAACAGGACCATGTACA
 227   Y  C  A  P  A  G  F  A  I  L  K  C  N  N  K  T  F  N  G  T  G  P  C  T

2305  AATGTCAGCACAGTACACATGGAATTAGGCCAGTAGTATCAACTGCTGTTGAATGGCAGT
 251   N  V  S  T  V  Q  C  T  H  G  I  R  P  V  V  S  T  Q  L  L  L  N  G  S

2377  CTAGCAGAAGAAGAGGTAGTAATTAGATCTGCCAATTTCACAGACAATGCTAAAACCATAATAGTACAGCTG
 275   L  A  E  E  E  V  V  I  R  S  A  N  F  T  D  N  A  K  T  I  I  V  Q  L
```

FIGURE 3E

```
2449  AACCAATCTGTAGAAATTAATTGTACAAGACCCAACAACAATACAAGAAAAAGTATCCGTATCCAGAGGGA
 299   N  Q  S  V  E  I  N  C  T  R  P  N  N  N  T  R  K  S  I  R  I  Q  R  G

2521  CCAGGGAGAGCATTTGTTACAATAGGAAAAATATGAGACAAGCACATTGTAACATTAGTAGAGCA
 323   P  G  R  A  F  V  T  I  G  K  I  G  N  M  R  Q  A  H  C  N  I  S  R  A

2593  AAATGGAATGCCACTTTAAAACAGATAGCTAGCAAATTAAGAGAACAATTTGGAAATAATAAAACAATAATC
 347   K  W  N  A  T  L  K  Q  I  A  S  K  L  R  E  Q  F  G  N  N  K  T  I  I

2665  TTTAAGCAATCCTCAGGAGGGGACCCAGAAATTGTAACGCACAGTTTTAATTGTGGAGGGAATTTTCTAC
 371   F  K  Q  S  S  G  G  D  P  E  I  V  T  H  S  F  N  C  G  G  E  F  F  Y

2737  TGTAATTCAACACACAACTGTTTAATAGTACTTGGTTTAATAGTACTTGAAGGTCAAATAACACT
 395   C  N  S  T  Q  L  F  N  S  T  W  F  N  S  T  W  S  T  E  G  S  N  N  T

2809  GAAGGAAGTGACACACAATCACACTCCCATGCAGAATAAACAATTTATAAACATGTGGCAGGAAGTAGGAAAA
 419   E  G  S  D  T  I  T  L  P  C  R  I  K  Q  F  I  N  M  W  Q  E  V  G  K

2881  GCAATGTATGCCCCTCCCATCAGCGGACAAATTAGATGTTCATCAAATATTACAGGGCTGCTATTAACAAGA
 443   A  M  Y  A  P  P  I  S  G  Q  I  R  C  S  S  N  I  T  G  L  L  L  T  R

2953  GATGGTGGTAATAACAACAATGGGTCCGAGATCTTCAGACCTGGAGGAGGAGATATGAGGGACAATTGGAGA
 467   D  G  G  N  N  N  N  G  S  E  I  F  R  P  G  G  G  D  M  R  D  N  W  R
```

FIGURE 3F

```
3025  AGTGAATTATATAAATATAAAGTAGTAAAAATTGAACCATTAGGAGTAGCACCCACCAAGGCAAAGAGAAGA
491    S  E  L  Y  K  Y  K  V  V  K  I  E  P  L  G  V  A  P  T  K  A  K  R  R
                                        NotI
3097  GTGGTGCAGAGAGAAAAATGAGCGGCCGC
515    V  V  Q  R  E  K  -
```

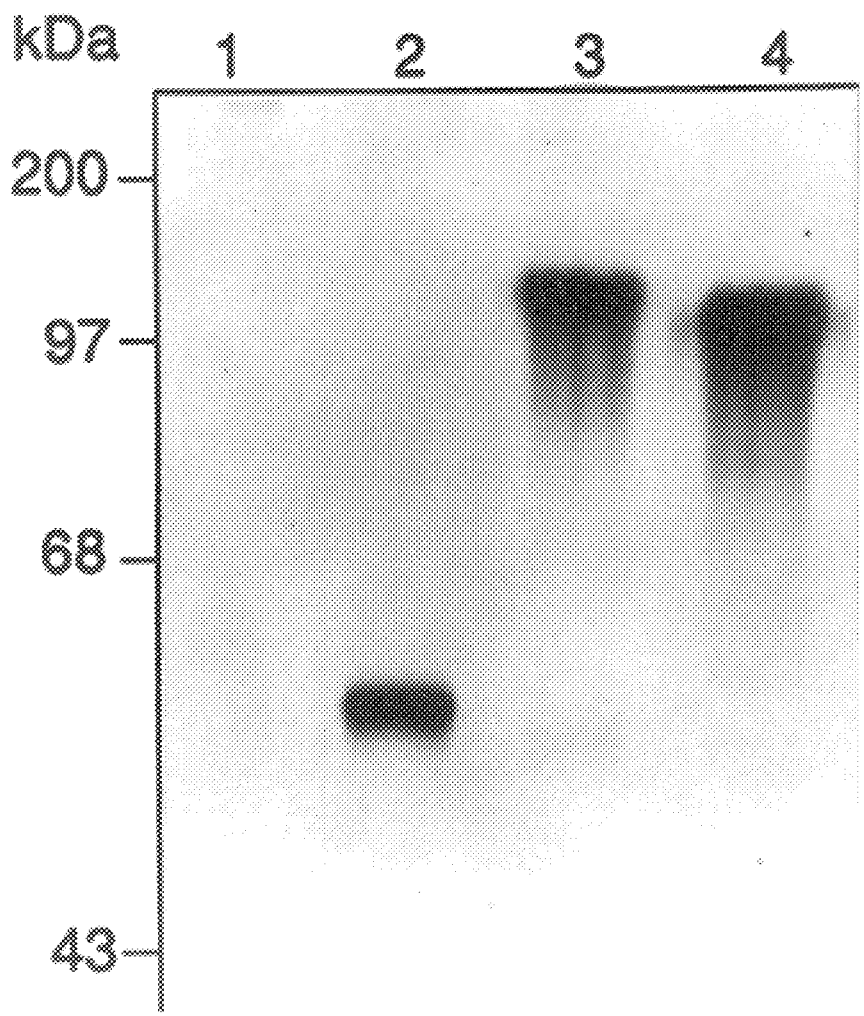

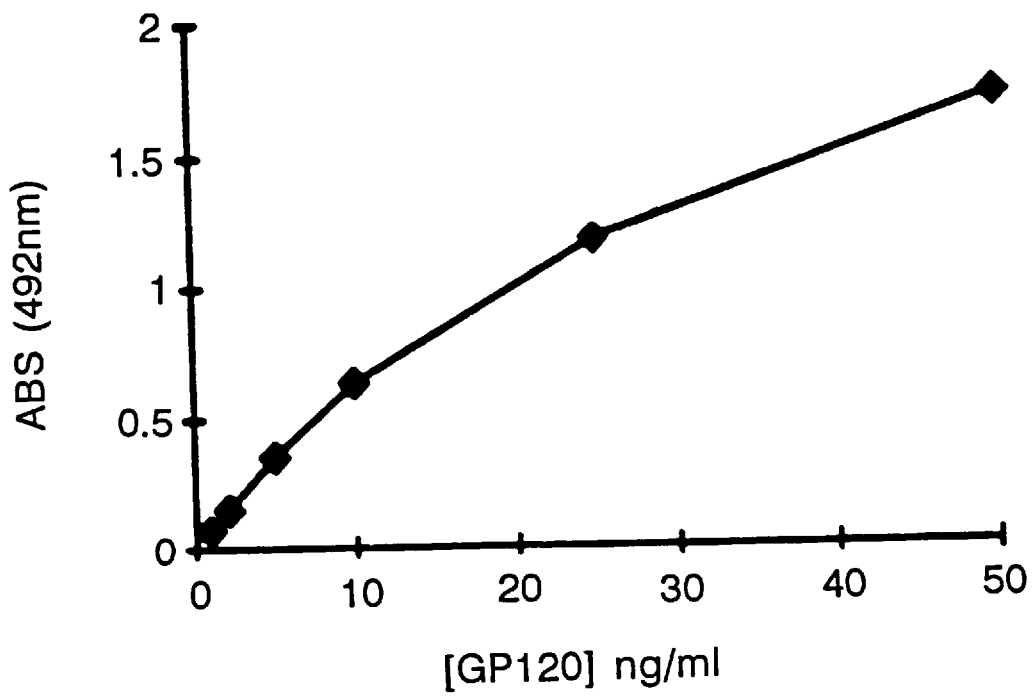

FIGURE 7A

```
JR-FL
  1                                                     ATGGATGCAATGAAGAGA
  1                                                      M  D  A  M  K  R

19  GGGCTCTCTGCTGTGTGTGCTGTGTGGAGCAGTCTTCGTTTCGCCCAGCCAGGAAATC
  7   G  L  C  C  V  L  L  C  G  A  V  F  V  S  P  S  Q  E  I
                                NarI
 79  CATGCCCGATTCAGAGAGAGGCGGCAGAGTAGAAAAGTTGTGGGTCACAGTCTATTATGGG
 27   H  A  R  F  R  R  G  A  R  V  E  K  L  W  V  T  V  Y  Y  G
                          ▲Signal cleavage
139  GTACCTGTGTGGAAAGAAGCAACCACCACTCTATTTTGTGCATCAGATGCTAAAGCATAT
 47   V  P  V  W  K  E  A  T  T  L  F  C  A  S  D  A  K  A  Y 199  GATACAGAGGTACATAATGTTTGGGCCACACATGCCTGTGTACCCACAGACCCCAACCCA
 67   D  T  E  V  H  N  V  W  A  T  H  A  C  V  P  T  D  P  N  P 259  CAAGAAGTAGTATTGGAAAATGTAACAGAACATTTTAACATGTGGAAAAATAACATGGTA
 87   Q  E  V  V  L  E  N  V  T  E  H  F  N  M  W  K  N  N  M  V 319  GAACAGATGCAGGAGGATATAATCAGTTTATGGGATCAAAGCTAAAGCCATGTGTAAAA
107   E  Q  M  Q  E  D  I  I  S  L  W  D  Q  S  L  K  P  C  V  K 379  TTAACCCCACTCTGTGTTACTTTAAATTGCAAGGATGTGAATGCTACTAATACCACTAAT
127   L  T  P  L  C  V  T  L  N  C  K  D  V  N  A  T  N  T  T  N 439  GATAGCGAGGGAACGATGGAGAGAGGAGAAATAAAAAACTGCTCTTTCAATATCACCACA
147   D  S  E  G  T  M  E  R  G  E  I  K  N  C  S  F  N  I  T  T
```

FIGURE 7B

```
499  AGCATAAGAGATGAGGTGCAGAAAGAATATGCTCTTTTTTATAAACTTGATGTAGTACCA
167   S   I   R   D   E   V   Q   K   E   Y   A   L   F   Y   K   L   D   V   V   P

559  ATAGATAATAATAATACCAGCTATAGGTTGTGATAAGTTGTGACACCTCAGTCATTACACAG
187   I   D   N   N   N   T   S   Y   R   L   I   S   C   D   T   S   V   I   T   Q

619  GCCTGTCCAAAGATATCCTTTGAGCCAATTCCCATACATTATTGTGCCCCGGCTGGTTTT
207   A   C   P   K   I   S   F   E   P   I   P   H   Y   C   A   P   A   G   F

679  GCGATTCTAAAGTGTAATGATAAGACGTTCAATGGAAAAGGACCATGTAAAAATGTCAGC
227   A   I   L   K   C   N   D   K   T   F   N   G   K   G   P   C   K   N   V   S

739  ACAGTACAATGTACACATGGAATTAGGCCAGTAGTATCAACTCAACTGCTGCTAAATGGC
247   T   V   Q   C   T   H   G   I   R   P   V   V   S   T   Q   L   L   L   N   G

799  AGTCTAGCAGAAGAAGAGGTAGTAATTAGATCTGAAAGAATCTGTAGAAATTAATTCACGAACAATGCTAAAACC
267   S   L   A   E   E   E   V   V   I   R   S   D   N   F   T   N   N   A   K   T

859  ATAATAGTACAGCTGAAAGAATCTGTAGAAATTAATTGTACAAGACCCAACAACAATACA
287   I   I   V   Q   L   K   E   S   V   E   I   N   C   T   R   P   N   N   T

919  AGAAAAAGTATACATATAGGACCAGGGAGAGCATTTTATACTACAGGAGAAATAATAGGA
307   R   K   S   I   H   I   G   P   G   R   A   F   Y   T   T   G   E   I   I   G

979  GATATAAGACAAGCACATTGTAACATTAGTAGAGCAAAATGGAATGACACTTTAAAACAG
327   D   I   R   Q   A   H   C   N   I   S   R   A   K   W   N   D   T   L   K   Q
```

FIGURE 7C

```
1039  ATAGTTATAAATTAAGAGAACAATTTGAGAATAAAACAATAGTCTTTAATCACTCCTCA
 347    I  V  I  K  L  R  E  Q  F  E  N  K  T  I  V  F  N  H  S  S

1099  GGAGGGGACCCAGAAATTGTAATGCACAGTTTAATTGTGGAGGAGAATTTTCTACTGT
 367    G  G  D  P  E  I  V  M  H  S  F  N  C  G  G  E  F  F  Y  C

1159  AATTCAACACAACTGTTTAATAGTACTTGGAATAATAATACTGAAGGGTCAAATAACACT
 387    N  S  T  Q  L  F  N  S  T  W  N  N  N  T  E  G  S  N  N  T

1219  GAAGGAAATACTATCACACTCCCATGCAGAATAAAACAAATTATAAACATGTGGCAGGAA
 407    E  G  N  T  I  T  L  P  C  R  I  K  Q  I  I  N  M  W  Q  E

1279  GTAGGAAAAGCAATGTATGCCCCTCCCATCAGAGGACAAATTAGATGTTCATCAAATATT
 427    V  G  K  A  M  Y  A  P  P  I  R  G  Q  I  R  C  S  S  N  I

1339  ACAGGGCTGCTATTAACAAGAGATGGTGTATTAATGAGAATGGGACCGAGATCTTCAGA
 447    T  G  L  L  L  T  R  D  G  G  I  N  E  N  G  T  E  I  F  R

1399  CCTGGAGGAGAGATATGAGGGACAATTGGAGAAGTGAATTATATAAATATAAAGTAGTA
 467    P  G  G  G  D  M  R  D  N  W  R  S  E  L  Y  K  V  V

1459  AAAATTGAACCATTAGGAGTAGCACCCACCAAGGCAAAGACTAAAGCAAAGAGAGTGGTGCAAAGAGAA
 487    K  I  E  P  L  G  V  A  P  T  K  A  K  R  R  V  V  Q  R  E
              NotI

1519  AAATGAGCGGCCGC
 507    K
```

FIGURE 8A

```
LAI ΔV3

1                                           ATGGATGCAATGAAGAGAGGGCTCTGCTGTGTGCTG
  1                                            M  D  A  M  K  R  G  L  C  C  V  L
                                                              NarI
 37   CTGCTGTGTGGAGCAGTCTTCGTTTCGCCCAGCCAGGAAATCCATGCCCGATTCAGAAGAGGCGCCAGAACA
 13    L  L  C  G  A  V  F  V  S  P  S  Q  E  I  H  A  R  F  R  R  G  A  R  T
                                                        Signal cleavage ▲

109   GAAAAATTGTGGGTCACAGTCTATTATGGGGTACCTGTGTGGAAGGAAGCAACCACTCTATTTTGTGCA
 37    E  K  L  W  V  T  V  Y  Y  G  V  P  V  W  K  E  A  T  T  L  F  C  A

181   TCAGATGCTAAAGCATATGATACAGAGGTACATAATGTTTGGGCCACACATGCCTGTGTACCCACAGACCCC
 61    S  D  A  K  A  Y  D  T  E  V  H  N  V  W  A  T  H  A  C  V  P  T  D  P

253   AACCCACAAGAAGTAGTACTGGTAAATGTGACAGAAAATTTTAACATGTGGAAAAATGACATGGTAGAACAG
 85    N  P  Q  E  V  V  L  V  N  V  T  E  N  F  N  M  W  K  N  D  M  V  E  Q

325   ATGCATGAGGATATAATCAGTTTATGGGATCAAAGCCTAAAGCCATGTGTAAAATTAACCCCACTCTGTGTT
109    M  H  E  D  I  I  S  L  W  D  Q  S  L  K  P  C  V  K  L  T  P  L  C  V

397   AGTTTAAAGTGCACTGATTTGGGGAATGCTACTAATACCAATAGTAGTAATACCAATAGTAGTAGCGGGGAA
133    S  L  K  C  T  D  L  G  N  A  T  N  T  N  S  S  N  T  N  S  S  S  G  E
```

FIGURE 8B

```
469  ATGATGATGGGAGAAAGGAGAGATAAAAAACTGCTCTTTCAATATCAGCACAAGCATAAGAGGTAAGGTGCAG
157   M  M  M  E  K  G  E  I  K  N  C  S  F  N  I  S  T  S  I  R  G  K  V  Q

541  AAAGAATATGCATTTTTTATAAACTTGATATAATACCAATAGATAATGATACTACCAGCTATACGTTGACA
181   K  E  Y  A  F  F  Y  K  L  D  I  I  P  I  D  N  D  T  T  S  Y  T  L  T

613  AGTTGTAACACCTCAGTCATTACACAGGCCTGTCCAAAGGTATCCTTTGAGCCAATTCCCATACATTATTGT
205   S  C  N  T  S  V  I  T  Q  A  C  P  K  V  S  F  E  P  I  P  I  H  Y  C

685  GCCCCGGCTGGTTTTGCGATTCTAAAATGTAATAATAAGACGTTCAATGGAACAGGACCATGTACAAATGTC
229   A  P  A  G  F  A  I  L  K  C  N  N  K  T  F  N  G  T  G  P  C  T  N  V

757  AGCACAGTACAATGTACACATGGAATTAGGCCAGTAGTATCAACTGCTGTTGAATGGCAGTCTAGCA
253   S  T  V  Q  C  T  H  G  I  R  P  V  V  S  T  Q  L  L  L  N  G  S  L  A

829  GAAGAAGAGGTAGTAATTAGATCTGCCAATTTCACAGACAATGCTAAAACCATAATAGTACAGCTGAACCAA
277   E  E  E  V  V  I  R  S  A  N  F  T  D  N  A  K  T  I  I  V  Q  L  N  Q

901  TCTGTAGAAATTAATTGTACAGGTGCTGGACATTGTAACATTAGTAGAGCAAAATGGAATGCCACTTTAAAA
301   S  V  E  I  N  C  T  G  A  G  H  C  N  I  S  R  A  K  W  N  A  T  L  K
```

FIGURE 8C

```
 973  CAGATAGCTAGCAAATTAAGAGAACAATTTGGAAATAATAAAACAATAATCTTTAAGCAATCCTCAGGAGG
 325    Q   I   A   S   K   L   R   E   Q   F   G   N   N   K   T   I   I   F   K   Q   S   S   G   G

1045  GACCCAGAAATTGTAACGCACAGTTTTAATTGTGGAGGGAATTTTCTACTGTAATTCAACACAACTGTTT
 349    D   P   E   I   V   T   H   S   F   N   C   G   G   E   F   F   Y   C   N   S   T   Q   L   F

1117  AATAGTACTTGGTTTAATAGTACTTGGAGTACTGAAGGGTCAAATAACACTGAAGGAAGTGACACAATCACA
 373    N   S   T   W   F   N   S   T   W   S   T   E   G   S   N   N   T   E   G   S   D   T   I   T

1189  CTCCCATGCAGAATAAAACAATTTATAAACATGTGGCAGGAAGTAGGAAAAGCAATGTATGCCCCTCCCATC
 397    L   P   C   R   I   K   Q   F   I   N   M   W   Q   E   V   G   K   A   M   Y   A   P   P   I

1261  AGCGGGACAAATTAGAGATGTTCATCAAATATTACAGGGCTGCTATTAACAAGAGATGGTGGTAATAACAAT
 421    S   G   Q   I   R   C   S   S   N   I   T   G   L   L   L   T   R   D   G   G   N   N   N   N

1333  GGGTCCGAGATCTTCAGACCTGGAGGAGGAGATATGAGGGACAATTGGAGAAGTGAATTATATAAATATAAA
 445    G   S   E   I   F   R   P   G   G   G   D   M   R   D   N   W   R   S   E   L   Y   K   Y   K

1405  GTAGTAAAAATTGAACCATTAGGAGTAGCACCCACCAAGGCAAAGAGAAGAGTGGTGCAGAGAGAAAAATGA
 469    V   V   K   I   E   P   L   G   V   A   P   T   K   A   K   R   R   V   V   Q   R   E   K   -

NotI
1477  GCGGCCGC
```

```
  1                                                   ATGGATGCAATGAAGAGA
  1                                                    M  D  A  M  K  R

19  GGGCTCTGCTGTGTGCTGTGTGCTGTGTGGAGCAGTCTTCGTTTCGCCCAGCCAGGAAATC
  7   G  L  C  C  V  L  L  C  G  A  V  F  V  S  P  S  Q  E  I
                                        NarI
 79  CATGCCCGATTCAGAGAGGCGGCAGAGAGTAGAAAAGTTGTGGTCACAGTCTATTATGGG
 27   H  A  R  F  R  R  G  A  R  V  E  K  L  W  V  T  V  Y  Y  G
                       ▲ Signal cleavage
139  GTACCTGTGTGGAAAGAAGCAACCACCACTCTATTTGTGCATCAGATGCTAAAGCATAT
 47   V  P  V  W  K  E  A  T  T  L  F  C  A  S  D  A  K  A  Y 199  GATACAGAGGTACATAATGTTTGGGCCACAGACCCCACCCA
 67   D  T  E  V  H  N  V  W  A  T  H  A  C  V  P  T  D  P  N  P 259  CAAGAAGTAGTATTGGAAAATGTAACAGAACATTTTAACATGTGGAAAAATAACATGGTA
 87   Q  E  V  V  L  E  N  V  T  E  H  F  N  M  W  K  N  N  M  V 319  GAACAGATGCAGGAGGATATAATCAGTTTATGGGATCAAAGCCTAAAGCCATGTGTAAAA
107   E  Q  M  Q  E  D  I  I  S  L  W  D  Q  S  L  K  P  C  V  K 379  TTAACCCCACTCTGTGTTACTTTAAATTGCAAGGATGTGAATGCTACTAATACCACTAAT
127   L  T  P  L  C  V  T  L  N  C  K  D  V  N  A  T  N  T  T  N 439  GATAGCGAGGGAACGATGGAGAGAGGAGAAATAAAAAAACTGCTCTTTCAATATCACCACA
147   D  S  E  G  T  M  E  R  G  E  I  K  N  C  S  F  N  I  T  T
```

FIGURE 9B

```
499  AGCATAAGAGATGAGGTGCAGAAAGAATATGCTCTTTTTTATAAACTTGATGTAGTACCA
167   S  I  R  D  E  V  Q  K  E  Y  A  L  F  Y  K  L  D  V  V  P

559  ATAGATAATAATACCAGCTATAGGTTGATAAGTTGTGACACCTCAGTCATTACACAG
187   I  D  N  N  T  S  Y  R  L  I  S  C  D  T  S  V  I  T  Q

619  GCCTGTCCAAAGATATCCTTTGAGCCAATTCCCATACATTATTGTGCCCCGGCTGGTTTT
207   A  C  P  K  I  S  F  E  P  I  P  I  H  Y  C  A  P  A  G  F

679  GCGATTCTAAAGTGTAATGATAAGACGTTCAATGGAAAAGGACCATGTAAAAATGTCAGC
227   A  I  L  K  C  N  D  K  T  F  N  G  K  G  P  C  K  N  V  S

739  ACAGTACAATGTACACATGGAATTAGGCCAGTAGTATCAACTCAACTGCTAAATGGC
247   T  V  Q  C  T  H  G  I  R  P  V  V  S  T  Q  L  L  L  N  G

799  AGTCTAGCAGAAGAAGAGGTAGTAATTAGATCTGACAATTTCACGAACAATGCTAAAACC
267   S  L  A  E  E  E  V  V  I  R  S  D  N  F  T  N  N  A  K  T

859  ATAATAGTACAGCTGAAAGAATCTGTAGAAATTAATTGTACAGGTGCTGGACATTGTAAC
287   I  I  V  Q  L  K  E  S  V  E  I  N  C  T  G  A  G  H  C  N

919  ATTAGTAGACAAAATGGAATGACACTTTAAAACAGATAGTTATAAAATTAAGAGAACAA
307   I  S  R  K  W  N  D  T  L  K  Q  I  V  I  K  L  R  E  Q

979  TTTGAGAATAAAACAATAGTCTTTAATCACTCCTCAGGAGGGGACCCAGAAATTGTAATG
327   F  E  N  K  T  I  V  F  N  H  S  S  G  G  D  P  E  I  V  M
```

FIGURE 9C

```
1039  CACAGTTTAATTGTGGAGGAGAATTTTCTACTGTAATTCAACACAACTGTTTAATAGT
 347    H  S  F  N  C  G  G  E  F  F  Y  C  N  S  T  Q  L  F  N  S

1099  ACTTGGAATAATAATACTGAAGGGTCAAATAACACTGAAGGAAATACTATCACACTCCCA
 367    T  W  N  N  N  T  E  G  S  N  N  T  E  G  N  T  I  T  L  P

1159  TGCAGAATAAAACAAATTAGATGTTCATCAAATATTACAGGGCTGCTATTAACAAGAGAT
 387    C  R  I  K  Q  I  I  N  M  W  Q  E  V  G  K  A  M  Y  A  P

1219  CCCATCAGAGGACAAATTAGATGTTCATCAAATATTACAGGGCTGCTATTAACAAGAGAT
 407    P  I  R  G  Q  I  R  C  S  S  N  I  T  G  L  L  L  T  R  D

1279  GGTGGTATTAATGAGAATGGGACCGAGATCTTCAGACCTGGAGGAGAGATATGAGGGAC
 427    G  G  I  N  E  N  G  T  E  I  F  R  P  G  G  G  D  M  R  D

1339  AATTGGAGAAGTGAATTATATAAATATAAAGTAGTAAAAATTGAACCATTAGGAGTAGCA
 447    N  W  R  S  E  L  Y  K  Y  K  V  V  K  I  E  P  L  G  V  A
                                                            NotI
1399  CCCACCAAGGCAAAGAGAAGAGTGGTGCAAAGAGAAAAATGAGGCGGCCGC
 487    P  T  K  A  K  R  R  V  V  Q  R  E  K  -
```

FIGURE 10A

LAI ΔV3-CD4⁻

```
  1  ATGGATGCAATGAAGAGAGGGCTCTGTGTGCTG
  1   M  D  A  M  K  R  G  L  C  C  V  L

37  CTGCTGTGTGGAGCAGTCTTCGTTTCGCCCAGCCAGGAAATCCATGCCCGATTCAGAAGAGGGCCAGAACA
 13   L  L  C  G  A  V  F  V  S  P  S  Q  E  I  H  A  R  F  R  R  G  A  R  T
                         NarI          Signal cleavage ▲

109  GAAAAATTGTGGGTCACAGTCTATTATGGGTACCTGTGTGGAAGGAAGCAACCACTCTATTTGTGCA
 37   E  K  L  W  V  T  V  Y  Y  G  V  P  V  W  K  E  A  T  T  L  F  C  A

181  TCAGATGCTAAAGCATATGATACAGAGGTACATAATGTTTGGGCCACACATGCCTGTGTACCCACAGACCCC
 61   S  D  A  K  A  Y  D  T  E  V  H  N  V  W  A  T  H  A  C  V  P  T  D  P

253  AACCCACAAGAAGTAGTATTGGTAATGTGACAGAAAATTTAACATGTGGAAAAATGACATGGTAGAACAG
 85   N  P  Q  E  V  V  L  V  N  V  T  E  N  F  N  M  W  K  N  D  M  V  E  Q

325  ATGCATGAGGATATAATCAGTTTATGGGATCAAAGCCTAAAGCCATGTGTAAAATTAACCCCACTCTGTGTT
109   M  H  E  D  I  I  S  L  W  D  Q  S  L  K  P  C  V  K  L  T  P  L  C  V

397  AGTTTAAAGTGCACTGATTTGGGGAATGCTACTAATAATACCAATAGTAGTAGCGGGGAA
133   S  L  K  C  T  D  L  G  N  A  T  N  T  N  S  S  N  T  N  S  S  S  G  E

469  ATGATGATGGAGAAAGGAGAGATAAAAAACTGCTCTTTCAATATCAGCACAAGCATAAGAGGTAAGGTGCAG
157   M  M  M  E  K  G  E  I  K  N  C  S  F  N  I  S  T  S  I  R  G  K  V  Q
```

FIGURE 10B

```
541   AAAGAATATGCATTTTTTATAAACTTGATATAATACCAATAGATAATGATACTACCAGCTATACGTTGACA
181     K  E  Y  A  F  F  Y  K  L  D  I  I  P  I  D  N  D  T  T  S  Y  T  L  T

613   AGTTGTAACACCTCAGTCATTACACAGGCCTGTCCAAAGGTATCCTTTGAGCCAATTCCCATACATTATGT
205     S  C  N  T  S  V  I  T  Q  A  C  P  K  V  S  F  E  P  I  P  I  H  Y  C

685   GCCCCGGCTGGTTTTGCGATTCTAAAATGTAATAATAAGACGTTCAATGGAACAGGACCATGTACAAATGTC
229     A  P  A  G  F  A  I  L  K  C  N  N  K  T  F  N  G  T  G  P  C  T  N  V

757   AGCACAGTACAATGTACACACATGGAATTAGGCCAGTAGTATCAACTCAACTGCTGTTGAATGGCAGTCTAGCA
253     S  T  V  Q  C  T  H  G  I  R  P  V  V  S  T  Q  L  L  L  N  G  S  L  A

829   GAAGAAGAGGTAGTAATTAGATCTGCCAATTTCACAGACAATGCTAAAACCATAATAGTACAGCTGAACCAA
277     E  E  V  V  I  R  S  A  N  F  T  D  N  A  K  T  I  I  V  Q  L  N  Q

901   TCTGTAGAAATTAATTGTACAGGTGCTGGACATTGTAACATTAGTAGAGCAAAATGGAATGCCACTTTAAAA
301     S  V  E  I  N  C  T  G  A  G  H  C  N  I  S  R  A  K  W  N  A  T  L  K

973   CAGATAGCTAGCAAATTAAGAGAACAATTTGGAAATAAAACAATAATCTTTAAGCAATCCTCAGGAGGG
325     Q  I  A  S  K  L  R  E  Q  F  G  N  N  K  T  I  I  F  K  Q  S  S  G  G

1045  GACCCAGAAATTGTAACGCACACAGTTTTAATTGTGGAGGGAATTTTTCTACTGTAATTCAACACAACTGTTT
349     D  P  E  I  V  T  H  S  F  N  C  G  G  E  F  F  Y  C  N  S  T  Q  L  F
```

FIGURE 10C

```
1117  AATAGTACTTGGTTTAATAGTACTTGGAGTACTGAAGGTCAAATAACACTGAAGGAAGTGACACAATCACA
 373    N  S  T  W  F  N  S  T  W  S  T  E  G  S  N  N  T  E  G  S  D  T  I  T

1189  CTCCCATGCAGAATAAACAATTTATAAACATGGTGCAGGAAGTAGGAAAAGCAATGTATGCCCCTCCCATC
 397    L  P  C  R  I  K  Q  F  I  N  M  V  Q  E  V  G  K  A  M  Y  A  P  P  I

1261  AGCGGGACAAATTAGATGTTCATCAAATATTACAGGGCTGCTATTAACAAGAGATGGTGGTAATAACAACAAT
 421    S  G  Q  I  R  C  S  S  N  I  T  G  L  L  L  T  R  D  G  G  N  N  N  N

1333  GGGTCCGAGATCTTCAGACCTGGAGGAGGAGATATGAGGGACAATTGGAGAAGTGAATTATATAAATATAAA
 445    G  S  E  I  F  R  P  G  G  G  D  M  R  D  N  W  R  S  E  L  Y  K  Y  K

1405  GTAGTAAAAATTGAACCATTAGGAGTAGCACCCACCAAGGCAAAGAGAAGAGTGGTGCAGAGAGAAAAATGA
 469    V  V  K  I  E  P  L  G  V  A  P  T  K  A  K  R  R  V  V  Q  R  E  K  -

NotI
1447                                                  GCGGCCGC
```

```
499   AGCATAAGAGATGAGGTGCAGAAAGAATATGCTCTCTTTTTATAAACTTGATGTAGTACCA
167    S  I  R  D  E  V  Q  K  E  Y  A  L  F  Y  K  L  D  V  V  P

559   ATAGATAATAATAACCAGCTATAGGTTGATAAGTTGTGACACCTCAGTCATTACACAG
187    I  D  N  N  T  S  Y  R  L  I  S  C  D  T  S  V  I  T  Q

619   GCCTGTCCAAAGATATCCTTTGAGCCAATTCCCATACATTATTGTGCCCCGGCTGGTTTT
207    A  C  P  K  I  S  F  E  P  I  P  I  H  Y  C  A  P  A  G  F

679   GCGATTCTAAAGTGTAATGATAAGACGTTCAATGGAAAAGGACCATGTAAAAATGTCAGC
227    A  I  L  K  C  N  D  K  T  F  N  G  K  G  P  C  K  N  V  S

739   ACAGTACAATGTACACACATGGAATTAGGCCAGTAGTATCAACTCAACTGCTGCTAAATGGC
247    T  V  Q  C  T  H  G  I  R  P  V  V  S  T  Q  L  L  L  N  G

799   AGTCTAGCAGAAGAGAGGTAGTAATTAGATCTGACAATTTCACGAACAATGCTAAAACC
267    S  L  A  E  E  E  V  V  I  R  S  D  N  F  T  N  N  A  K  T

859   ATAATAGTACAGCTGAAAGAATCTGTAGAATTAATTGTACAGGTGCTGGACATTGTAAC
287    I  I  V  Q  L  K  E  S  V  E  I  N  C  T  G  A  G  H  C  N

919   ATTAGTAGAGCAAAATGGAATGACACTTTAAAACAGATAGTTATAAATTAAGAGAACAA
307    I  S  R  A  K  W  N  D  T  L  K  Q  I  V  I  K  L  R  E  Q

979   TTTGAGAATAAAACAATAGTCTTTAATCACTCCTCAGGAGGGGACCCAGAAATTGTAATG
327    F  E  N  K  T  I  V  F  N  H  S  S  G  G  D  P  E  I  V  M
```

FIGURE 11C

```
1039  CACAGTTTTAATTGTGTGGAGGAGAATTTTCTACTGTAATTCAACACAACTGTTTAATAGT
 347   H  S  F  N  C  G  G  E  F  F  Y  C  N  S  T  Q  L  F  N  S

1099  ACTTGGAATAATAATACTGAAGGGTCAAATAACACTGAAGGAAATACTATCACACTCCCA
 367   T  W  N  N  N  T  E  G  S  N  N  T  E  G  N  T  I  T  L  P

1159  TGCAGAATAAAACAAATTATAAACATGGTGCAGGAAGTAGGAAAAGCAATGTATGCCCCT
 387   C  R  I  K  Q  I  I  N  M  V  Q  E  V  G  K  A  M  Y  A  P

1219  CCCATCAGAGGACAAATTAGATGTTCATCAAATATTACAGGGCTGCTATTAACAAGAGAT
 407   P  I  R  G  Q  I  R  C  S  S  N  I  T  G  L  L  T  R  D

1279  GGTGGTATTAATGAGAATGGGACCGAGATCTTCAGACCTGGAGGAGGAGATATGAGGGAC
 427   G  G  I  N  E  N  G  T  E  I  F  R  P  G  G  G  D  M  R  D

1339  AATTGGAGAAGTGAATTATATAAAGTAGTAAAAATTGAACCATTAGGAGTAGCA
 447   N  W  R  S  E  L  Y  K  V  K  V  V  K  I  E  P  L  G  V  A
                                                        NotI
1399  CCCACCAAGGCAAAGAGAAGAGTGGTGCAAAGAGAAAAATGAGCGGCCGC
 487   P  T  K  A  K  R  R  V  V  Q  R  E  K  -
```

FIGURE 12A

```
                                      tPA signal sequence
                       ATGGATGCAATGAAGAGACCCGATTCAGAAGAGGCTCTGCTGT
                        M  D  A  M  K  R  G  L  C  C
LAI CD4⁻                                                NarI
  1                                                   GGCGCC
  1

37  GTGCTGCTGCTGTGTGGAGCAGTCTCTTCGTTTCGCCCAGGAAATCCATGCCCGATTCAGAAGAGGCTCTGCTGT
 13   V  L  L  C  G  A  V  F  V  S  P  S  Q  E  I  H  A  R  F  R  R  G  A

109  AGAACAGAAAAATTGTGGGTCACAGTCTATTATGGGTACCTGTGTGGAAGGAAGCAACCACCACTCTATTT
 37   R  T  E  K  L  W  V  T  V  Y  Y  G  V  P  V  W  K  E  A  T  T  T  L  F
     ▲ Signal cleavage 181  TGTGCAGATCAGATGCTAAAGCATATGATACAGAGGTACACATAATGTTTGGGCCACACATGCCTGTGTACCCACA
 61   C  A  S  D  A  K  A  Y  D  T  E  V  H  N  V  W  A  T  H  A  C  V  P  T 253  GACCCCCAACCCCACAAGAGTATTGGTAAATGTGACAGAAAATTTAACATGTGGAAAAATGACATGGTA
 85   D  P  N  P  Q  E  V  V  L  V  N  V  T  E  N  F  N  M  W  K  N  D  M  V 325  GAACAGATGCATGAGGATATAATCAGTTTATGGGATCAAAGCCTAAAGCCATGTGTAAAATTAACCCCACTC
109   E  Q  M  H  E  D  I  I  S  L  W  D  Q  S  L  K  P  C  V  K  L  T  P  L 397  TGTGTTAGTTTAAAGTGCACTGATTTGGGGAATGCTACTAATACCAATAGTAGTAACAATAGTAGTAGC
133   C  V  S  L  K  C  T  D  L  G  N  A  T  N  T  N  S  S  N  T  N  S  S  S 469  GGGGAAATGATGATGGAGAAAGGAGAGATAAAAAACTGCTCTTTCAATATCAGCACACAAGCATAAGAGGTAAG
157   G  E  M  M  E  K  G  E  I  K  N  C  S  F  N  I  S  T  S  I  R  G  K
```

FIGURE 12B

```
541   GTGCAGAAAGAATATGCATTTTTTATAAACTTGATATAATACCAATAGATAATGATACTACCAGCTATACG
181    V  Q  K  E  Y  A  F  F  Y  K  L  D  I  I  P  I  D  N  D  T  T  S  Y  T

613   TTGACAAGTTGTAACACCTCAGTCATTACACAGGCCTGTCCAAAGGTATCCTTTGAGCCAATTCCCATACAT
205    L  T  S  C  N  T  S  V  I  T  Q  A  C  P  K  V  S  F  E  P  I  P  I  H

685   TATTGTGCCCCGGCTGGTTTTGCGATTCTAAAATGTAATAATAAGACGTTCAATGGAACAGGACCATGTACA
229    Y  C  A  P  A  G  F  A  I  L  K  C  N  N  K  T  F  N  G  T  G  P  C  T

757   AATGTCAGCACAGTACAATGTACACATGGAATTAGGCCAGTAGTATCAACTCAACTGCTGTTGAATGGCAGT
253    N  V  S  T  V  Q  C  T  H  G  I  R  P  V  V  S  T  Q  L  L  L  N  G  S

829   CTAGCAGAAGAAGAGGTAGTAATTAGATCTGCCAATTTCACAGACAATGCTAAAACCATAATAGTACAGCTG
277    L  A  E  E  E  V  V  I  R  S  A  N  F  T  D  N  A  K  T  I  I  V  Q  L

901   AACCAATCTGTAGAAATTAATTGTACAAGACCCAACAACAATACAAGAAAAAGTATCCGTATCCAGAGGGGA
301    N  Q  S  V  E  I  N  C  T  R  P  N  N  N  T  R  K  S  I  R  I  Q  R  G

973   CCAGGGAGAGCATTTGTTACAATAGGAAAAATATGAGACAAGCACATTGTAACATTAGTAGAGCA
325    P  G  R  A  F  V  T  I  G  K  I  G  N  M  R  Q  A  H  C  N  I  S  R  A

1045  AAATGGAATGCCACTTTAAAACAGATAGCTAGCAAATTAAGAGAACAATTTGGAAATAATAAAACAATAATC
349    K  W  N  A  T  L  K  Q  I  A  S  K  L  R  E  Q  F  G  N  N  K  T  I  I
```

FIGURE 12C

```
1117  TTTAAGCAATCCTCAGGAGGGGACCCAGAAATTGTAACGCACAGTTTAATTGTGGAGGGAATTTTCTAC
 373   F  K  Q  S  S  G  G  D  P  E  I  V  T  H  S  F  N  C  G  G  E  F  F  Y

1189  TGTAATTCAACACAACTGTTTAATAGTACTTGGTTTAATAGTACTGAAGGTCAAATAACACT
 397   C  N  S  T  Q  L  F  N  S  T  W  F  N  S  T  E  G  S  N  T

1261  GAAGGAAGTGACACAATCACACTCCCATGCAGAATAAACAATTTATAAACATGGTGAGGAAGTAGGAAAA
 421   E  G  S  D  T  I  T  L  P  C  R  I  K  Q  F  I  N  M  V  Q  E  V  G  K

1333  GCAATGTATGCCCCTCCCATCAGCGGGACAAATTAGATGTTCATCAAATATTACAGGGCTGCTATTAACAAGA
 445   A  M  Y  A  P  P  I  S  G  Q  I  R  C  S  S  N  I  T  G  L  L  L  T  R

1405  GATGGTGGTAATAACAACAATGGGTCCGAGATCTTCAGACCTGGAGGAGGAGATATGAGGGACAATTGGAGA
 469   D  G  G  N  N  N  N  G  S  E  I  F  R  P  G  G  G  D  M  R  D  N  W  R

1477  AGTGAATTATATATAAATATAAAGTAGTAAAAATTGAACCATTAGGAGTAGCACCCAAGGCAAAGAGAAGA
 493   S  E  L  Y  K  Y  K  V  V  K  I  E  P  L  G  V  A  P  T  K  A  K  R  R
                                                       NotI
1549  GTGGTGCAGAGAGAAAAATGAGCGGCCGC
 517   V  V  Q  R  E  K  -
```

```
1                                                          ATGGATGCAATGAAGAGA
1                                                           M  D  A  M  K  R

19   GGGCTCTGCTGTGTGCTGTGTGTGGAGCAGTCTTCGTTTCGCCCAGCCAGGAAATC
7     G  L  C  C  V  L  L  C  G  A  V  F  V  S  P  S  Q  E  I
                             NarI
79   CATGCCCGATTCAGAGAGGCGGCAGAGTAGAAAAGTTGTGGGTCACAGTCTATTATGGG
27    H  A  R  F  R  R  G  A  R  V  E  K  L  W  V  T  V  Y  Y  G
                        ▲ Signal cleavage
139  GTACCTGTGTGGAAAGAAGCAACCACCACTCTATTTTGTGCATCAGATGCTAAAGCATAT
47    V  P  V  W  K  E  A  T  T  T  L  F  C  A  S  D  A  K  A  Y 199  GATACAGAGGTACATAATGTTTGGGCCACACATGCCTGTGTACCCACAGACCCCAACCCA
67    D  T  E  V  H  N  V  W  A  T  H  A  C  V  P  T  D  P  N  P 259  CAAGAAGTAGTATTGGAAAATGTAACAGAACATTTTAACATGTGGAAAAATAACATGGTA
87    Q  E  V  V  L  E  N  V  T  E  H  F  N  M  W  K  N  N  M  V 319  GAACAGATGCAGGAGGATATAATCAGTTTATGGGATCAAAGCCTAAAGCCATGTGTAAAA
107   E  Q  M  Q  E  D  I  I  S  L  W  D  Q  S  L  K  P  C  V  K
```

FIGURE 13B

```
379  TTAACCCCCACTCTGTGTTACTTTAAATTGCAAGGATGTGAATGCTACTAATACCACTAAT
127   L  T  P  L  C  V  T  L  N  C  K  D  V  N  A  T  N  T  T  N

439  GATAGCGAGGGAACGATGGAGAGAGAGGAGAAATAAAAAACTGCTCTTTCAATATCACCACA
147   D  S  E  G  T  M  E  R  G  E  I  K  N  C  S  F  N  I  T  T

499  AGCATAAGAGATGAGGTGCAGAAAGAATATGCTCTCTTTTTATAAACTTGATGTAGTACCA
167   S  I  R  D  E  V  Q  K  E  Y  A  L  F  Y  K  L  D  V  V  P

559  ATAGATAATAATAACCAGCTATAGGTTGATAAGTTGTGACACCTCAGTCATTACACAG
187   I  D  N  N  T  S  Y  R  L  I  S  C  D  T  S  V  I  T  Q

619  GCCTGTCCAAAGATATCCTTTGAGCCAATTCCCATACATTATTGTGCCCCGGCTGGTTTT
207   A  C  P  K  I  S  F  E  P  I  P  I  H  Y  C  A  P  A  G  F

679  GCGATTCTAAAGTGTAATGATAAGACGTTCAATGGAAAAGGACCATGTAAAAATGTCAGC
227   A  I  L  K  C  N  D  K  T  F  N  G  K  G  P  C  K  N  V  S
```

FIGURE 13C

```
739  ACAGTACAATGTACACATGGAATTAGGCCAGTAGTATCAACTCAACTGCTGCTAAATGGC
247   T  V  Q  C  T  H  G  I  R  P  V  V  S  T  Q  L  L  L  N  G

799  AGTCTAGCAGAAGAAGAGGTAGTAATTAGATCTGACAATTTCACGAACAATGCTAAAACC
267   S  L  A  E  E  E  V  V  I  R  S  D  N  F  T  N  N  A  K  T

859  ATAATAGTACAGCTGAAAAGAATCTGTAGAAATTAATTGTACAAGACCCAACAACAATACA
287   I  I  V  Q  L  K  E  S  V  E  I  N  C  T  R  P  N  N  N  T

919  AGAAAAAGTATACATATAGGACCAGGGAGAGCATTTTATACTACAGGAGAAATAATAGGA
307   R  K  S  I  H  I  G  P  G  R  A  F  Y  T  T  G  E  I  I  G

979  GATATAAGACAAGCACATTGTAACATTAGTAGAGCAAAATGGAATGACACTTTAAAACAG
327   D  I  R  Q  A  H  C  N  I  S  R  A  K  W  N  D  T  L  K  Q
```

FIGURE 13D

```
1039  ATAGTTATAAAATTAAGAGAACAATTGAGAATAAAACAATAGTCTTTAATCACTCCTCA
 347   I  V  I  K  L  R  E  Q  F  E  N  K  T  I  V  F  N  H  S  S

1099  GGAGGGGACCCAGAAATTGTAATGCACAGTTTTAATTGTGGAGGAGAATTTTTCTACTGT
 367   G  G  D  P  E  I  V  M  H  S  F  N  C  G  G  E  F  F  Y  C

1159  AATTCAACAACTGTTTAATAGTACTTGGAATAATAATACTGAAGGGTCAAATAACACT
 387   N  S  T  Q  L  F  N  S  T  W  N  N  N  T  E  G  S  N  N  T

1219  GAAGGAAATACTATCACACTCCCATGCAGAATAAAACAAATTATAAACATGGTGCAGGAA
 407   E  G  N  T  I  T  L  P  C  R  I  K  Q  I  I  N  M  V  Q  E

1279  GTAGGAAAAGCAATGTATGCCCCTCCCATCAGAGGACAAATTAGATGTTCATCAAATATT
 427   V  G  K  A  M  Y  A  P  P  I  R  G  Q  I  R  C  S  S  N  I

1339  ACAGGGCTGCTATTAACAAGAGATGGTGGTATTAATGAGAATGGGACCGAGATCTTCAGA
 447   T  G  L  L  L  T  R  D  G  G  I  N  E  N  G  T  E  I  F  R

1399  CCTGGAGGAGGAGATATGAGGGACAATTGGAGAGAAGTGAATTATATAAATATAAGTAGTA
 467   P  G  G  G  D  M  R  D  N  W  R  S  E  L  Y  K  V  V

1459  AAAATTGAACCATTAGGAGTAGCACCCAAGGCAAAGAGAAGAGAGTGGTGCAAAGAGAA
 487   K  I  E  P  L  G  V  A  P  T  K  A  K  R  R  V  V  Q  R  E
                                              NotI
1519  AAATGAGCGGCCGC
 507   K
```

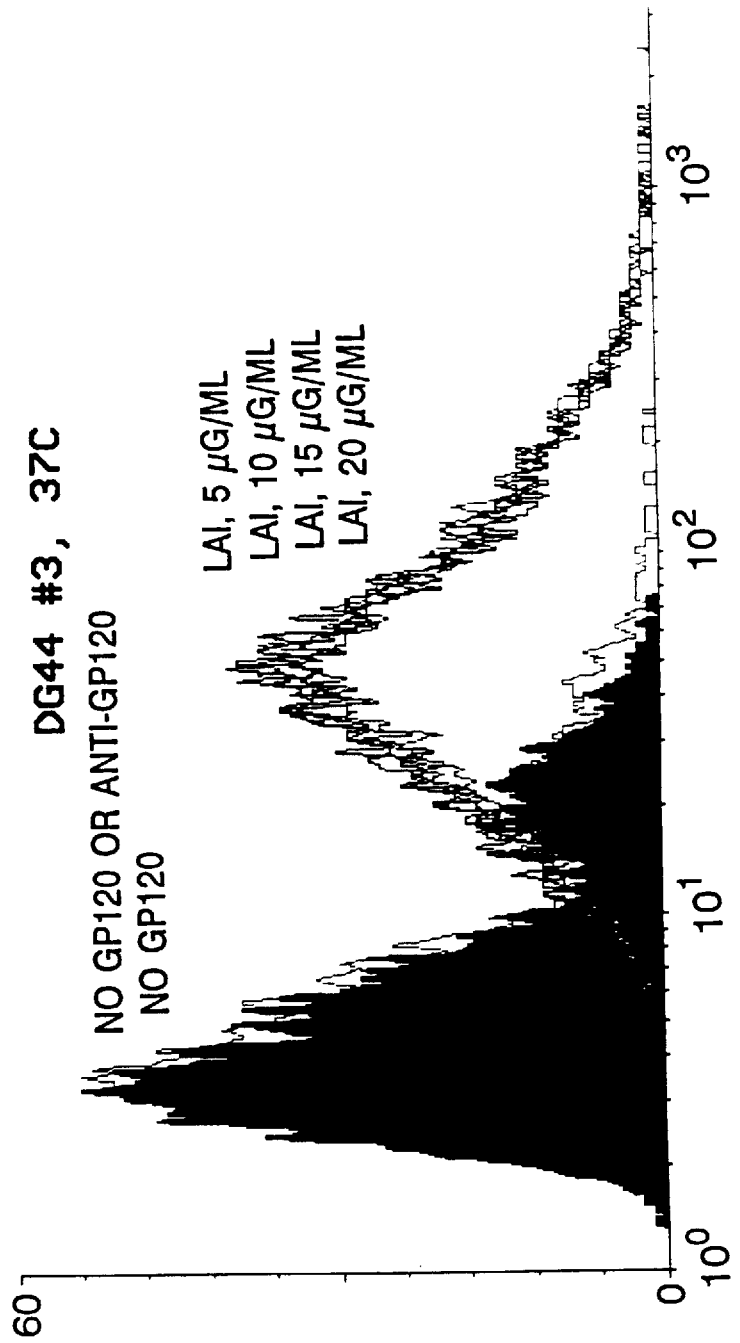

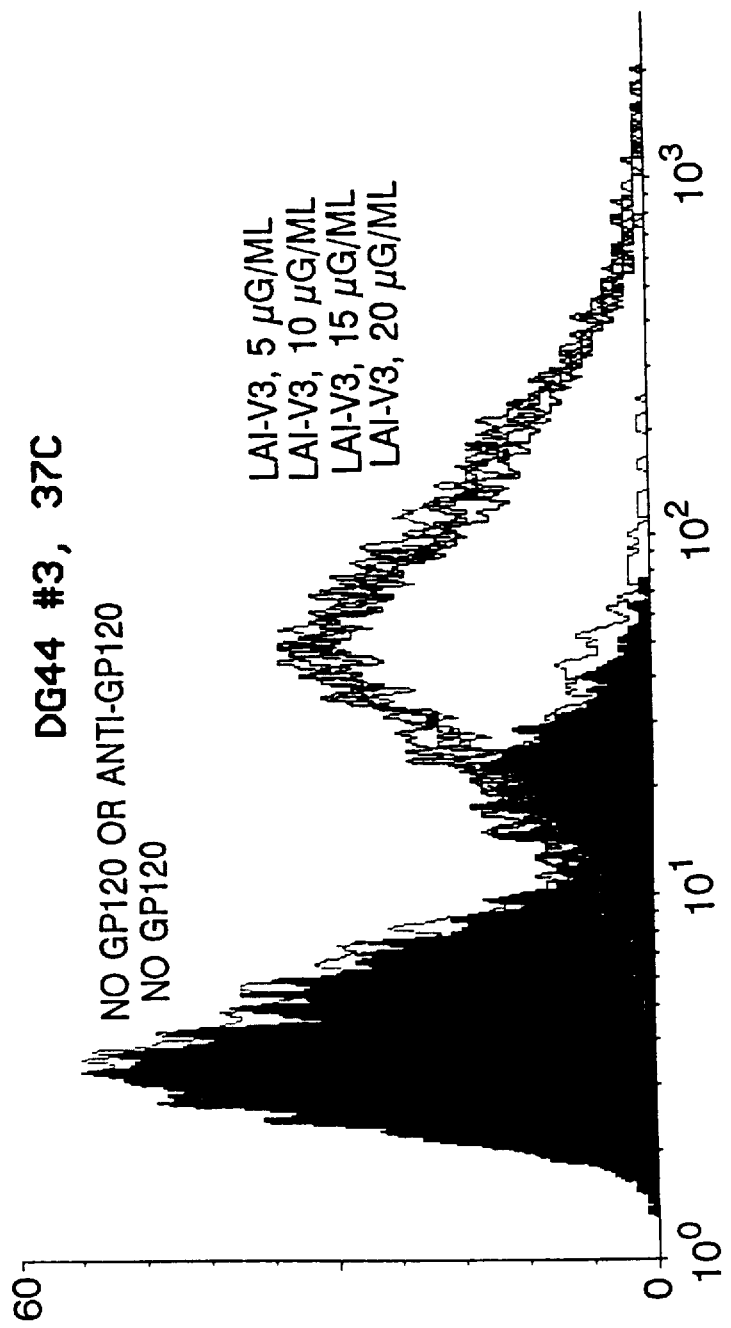

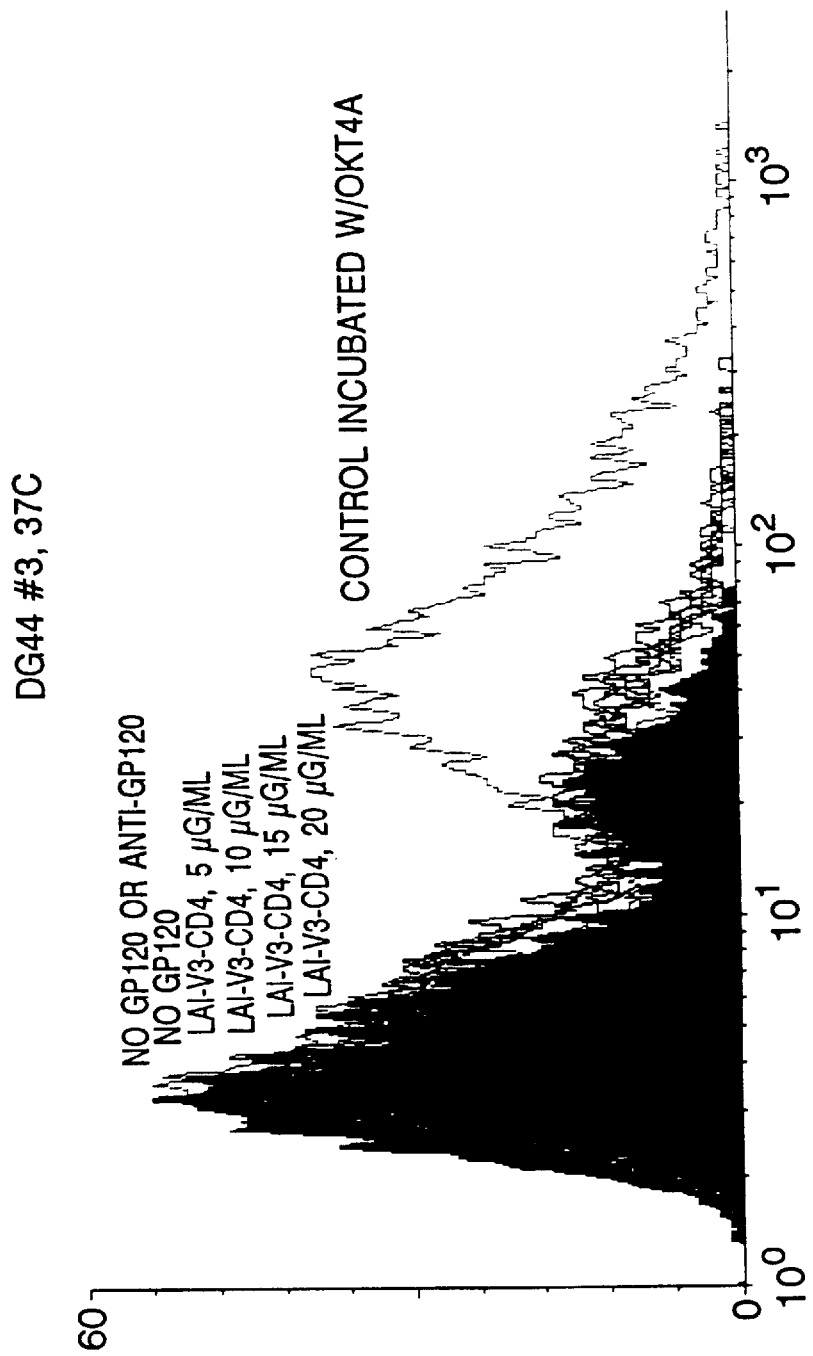

SEQUENCE LISTING ( 1 ) GENERAL INFORMATION:

( i i i ) NUMBER OF SEQUENCES: 29

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:1:

```
Xaa  Xaa  Xaa  Cys  Xaa  Ile  Xaa  Xaa  Xaa  Xaa  Xaa  Xaa  Trp  Xaa  Xaa  Xaa
 1                  5                        10                       15
Xaa  Xaa  Ala  Xaa  Tyr  Xaa  Xaa  Pro  Xaa  Xaa  Xaa  Xaa  Xaa  Xaa  Xaa  Xaa
               20                       25                       30
Ser  Xaa  Xaa  Thr  Gly  Xaa  Xaa  Xaa  Xaa  Arg  Xaa  Gly  Xaa
          35                       40                       45
```

( 2 ) INFORMATION FOR SEQ ID NO:2:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:2:

```
Thr  Leu  Pro  Cys  Arg  Ile  Lys  Gln  Phe  Ile  Asn  Met  Trp  Gln  Glu  Val
1                  5                            10                           15

Gly  Lys  Ala  Met  Tyr  Ala  Pro  Pro  Ile  Ser  Gly  Gln  Ile  Arg  Cys  Ser
              20                       25                      30

Ser  Asn  Ile  Thr  Gly  Leu  Leu  Leu  Thr  Arg  Asp  Gly  Gly
              35                       40                      45
```

( 2 ) INFORMATION FOR SEQ ID NO:3:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:3:

```
Thr  Leu  Pro  Cys  Arg  Ile  Lys  Gln  Ile  Ile  Asn  Met  Trp  Gln  Glu  Val
1                  5                            10                           15

Gly  Lys  Ala  Met  Tyr  Ala  Pro  Pro  Ile  Arg  Gly  Gln  Ile  Arg  Cys  Ser
              20                       25                      30

Ser  Asn  Ile  Thr  Gly  Leu  Leu  Leu  Thr  Arg  Asp  Gly  Gly
              35                       40                      45
```

( 2 ) INFORMATION FOR SEQ ID NO:4:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

GATCCTGCAG TCACCGTCCT TGACACGATG GATGCAATGA AGAGA        4 5

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AAGTCTTCTC CTCGGTCTTG TCTTTTTAAC ACCCAG        3 6

( 2 ) INFORMATION FOR SEQ ID NO:6:

( i ) SEQUENCE CHARACTERISTICS:
        ( A ) LENGTH: 36 base pairs
        ( B ) TYPE: nucleic acid (C) STRANDEDNESS: single
(D) TOPOLOGY: linear (i i) MOLECULE TYPE: DNA (genomic)

(x i) SEQUENCE DESCRIPTION: SEQ ID NO:6:

TTCAGAAGAG GAGCCAGAAC AGAAAAATTG TGGGTC 36

(2) INFORMATION FOR SEQ ID NO:7:

(i) SEQUENCE CHARACTERISTICS:
(A) LENGTH: 39 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:7:

GGAAAAAGC GGCCGCTCAT TTTTCTCTCT GCACCACTC 39

(2) INFORMATION FOR SEQ ID NO:8:

(i) SEQUENCE CHARACTERISTICS:
(A) LENGTH: 33 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:8:

GATCGGCGCC AGAGTAGAAA AGTTGTGGGT CAC 33

(2) INFORMATION FOR SEQ ID NO:9:

(i) SEQUENCE CHARACTERISTICS:
(A) LENGTH: 49 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:9:

CTGTAGAAAT TAATTGTACA GGTGCTGGAC ATTGTAACAT TAGTAGAGC 49

(2) INFORMATION FOR SEQ ID NO:10:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

(x i) SEQUENCE DESCRIPTION: SEQ ID NO:10:

CTCGAGCATG CATTCGAAGC TCGCTGATC 29

(2) INFORMATION FOR SEQ ID NO:11:

(i) SEQUENCE CHARACTERISTICS:
(A) LENGTH: 29 base pairs
(B) TYPE: nucleic acid
(C) STRANDEDNESS: single
(D) TOPOLOGY: linear (i i) MOLECULE TYPE: DNA (genomic)

( x i ) SEQUENCE DESCRIPTION: SEQ ID NO:11:

CAATTTATAA ACATGGTGCA GGAAGTAGG  29

( 2 ) INFORMATION FOR SEQ ID NO:12:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:12:

CAAATTATAA ACATGGTGCA GGAAGTAGG  29

( 2 ) INFORMATION FOR SEQ ID NO:13:

( i ) SEQUENCE CHARACTERISTICS:
        ( A ) LENGTH: 3125 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1555..3115
        ( D ) OTHER INFORMATION:

( x i ) SEQUENCE DESCRIPTION: SEQ ID NO:13:

```
TTGACATTGA TTATTGACTA GTTATTAATA GTAATCAATT ACGGGGTCAT TAGTTCATAG      60
CCCATATATG GAGTTCCGCG TTACATAACT TACGGTAAAT GGCCCGCCTG GCTGACCGCC     120
CAACGACCCC CGCCCATTGA CGTCAATAAT GACGTATGTT CCCATAGTAA CGCCAATAGG     180
GACTTTCCAT TGACGTCAAT GGGTGGACTA TTTACGGTAA ACTGCCCACT TGGCAGTACA     240
TCAAGTGTAT CATATGCCAA GTACGCCCCC TATTGACGTC AATGACGGTA ATGGCCCGC      300
CTGGCATTAT GCCCAGTACA TGACCTTATG GACTTTCCT ACTTGGCAGT ACATCTACGT      360
ATTAGTCATC GCTATTACCA TGGTGATGCG GTTTTGGCAG TACATCAATG GGCGTGGATA     420
GCGGTTTGAC TCACGGGGAT TTCCAAGTCT CCACCCCATT GACGTCAATG GGAGTTTGTT     480
TTGGCACCAA AATCAACGGG ACTTTCCAAA ATGTCGTAAC AACTCCGCCC CATTGACGCA     540
AATGGGCGGT AGGCGTGTAC GGTGGGAGGT CTATATAAGC AGAGCTCGTT TAGTGAACCG     600
TCAGATCGCC TGGAGACGCC ATCCACGCTG TTTTGACCTC CATAGAAGAC ACCGGGACCG     660
ATCCAGCCTC CGCGGCCGGG AACGGTGCAT TGGAACGCGG ATTCCCCGTG CCAAGAGTGA     720
CGTAAGTACC GCCTATAGAC TCTATAGGCA CACCCCTTTG GCTCTTATGC ATGCTATACT     780
GTTTTTGGCT TGGGCCAACA CCCCGTCCTA GATAGGTGAT GGTATAGCTT AGCCTATAGG     840
TGTGGGTTAT TGACCATTAT TGACCACTCC CCTATTGGTG ACGATACTTT CCATTACTAA     900
TCCATAACAT GGCCGCTCTT TGCCACAACT ATCTCTATTG CTATATGCC AATACTCTGT      960
CCTTCAGAGA CTGACACGGA CTCTGTATTT TTACAGGATG GGTCCCATT TATTATTTAC     1020
AAATTCACAT ATACAACAAC GCCGTCCCCC GTGCCCGCAG TTTTTATTAA CATGCGGGAT    1080
CTCCACGCGA ATCTCGGGTA CGTGTTCCGG ACATGGGCTC TTCTCCGGTA GCGGCGGAGC    1140
TCCACATCCG AGCCTGTCCC ATGCCCATGC CTCCAGCGGC TCATGGTCGC TCGGCAGCTC    1200
CTTGCTCCTA ACAGTGGAGG CCAGACTTAG GCACAGGACA ATGCCCACCA CCACCAGTGT    1260
GCCGCACAAG GCCGTGGCGG TAGGGTATGT GTCTGAAAAT GAGCTCGGAG ATTGGGCTCG    1320
```

```
CACCGCTGAC GCAGATGGAA GACTTAAGGC AGCGGCAGAA GAAGATGCAG GCAGCTGAGT    1380

TGTTGTATTC TGTAGAGTTG GAGGTAACTC CCGTTGCGGT GCTGTTAACG GTGGAGGGCA    1440

GTGTAGTCTG AGCAGTACTC GTTGCTGCCG CGCGCGCCAC CAGACATAAT AGCTGACAGA    1500

CTAACAGACT GTTCCTTTCC ATGGGTCTTT TCTGCAGTCA CCGTCCTTGA CACG ATG      1557
                                                              Met
                                                               1
```

| | | | | | | | | | | | | | | | | |
|---|---|---|---|---|---|---|---|---|---|---|---|---|---|---|---|---|
| GAT | GCA | ATG | AAG | AGA | GGG | CTC | TGC | TGT | GTG | CTG | CTG | CTG | TGT | GGA | GCA | 1605 |
| Asp | Ala | Met | Lys | Arg | Gly | Leu | Cys | Cys | Val | Leu | Leu | Leu | Cys | Gly | Ala | |
| | | | 5 | | | | | 10 | | | | | 15 | | | |
| GTC | TTC | GTT | TCG | CCC | AGC | CAG | GAA | ATC | CAT | GCC | CGA | TTC | AGA | AGA | GGC | 1653 |
| Val | Phe | Val | Ser | Pro | Ser | Gln | Glu | Ile | His | Ala | Arg | Phe | Arg | Arg | Gly | |
| | | | 20 | | | | 25 | | | | | 30 | | | | |
| GCC | AGA | ACA | GAA | AAA | TTG | TGG | GTC | ACA | GTC | TAT | TAT | GGG | GTA | CCT | GTG | 1701 |
| Ala | Arg | Thr | Glu | Lys | Leu | Trp | Val | Thr | Val | Tyr | Tyr | Gly | Val | Pro | Val | |
| | 35 | | | | | 40 | | | | | 45 | | | | | |
| TGG | AAG | GAA | GCA | ACC | ACC | ACT | CTA | TTT | TGT | GCA | TCA | GAT | GCT | AAA | GCA | 1749 |
| Trp | Lys | Glu | Ala | Thr | Thr | Thr | Leu | Phe | Cys | Ala | Ser | Asp | Ala | Lys | Ala | |
| 50 | | | | | 55 | | | | | 60 | | | | | 65 | |
| TAT | GAT | ACA | GAG | GTA | CAT | AAT | GTT | TGG | GCC | ACA | CAT | GCC | TGT | GTA | CCC | 1797 |
| Tyr | Asp | Thr | Glu | Val | His | Asn | Val | Trp | Ala | Thr | His | Ala | Cys | Val | Pro | |
| | | | | 70 | | | | | 75 | | | | | 80 | | |
| ACA | GAC | CCC | AAC | CCA | CAA | GAA | GTA | GTA | TTG | GTA | AAT | GTG | ACA | GAA | AAT | 1845 |
| Thr | Asp | Pro | Asn | Pro | Gln | Glu | Val | Val | Leu | Val | Asn | Val | Thr | Glu | Asn | |
| | | | 85 | | | | | 90 | | | | | 95 | | | |
| TTT | AAC | ATG | TGG | AAA | AAT | GAC | ATG | GTA | GAA | CAG | ATG | CAT | GAG | GAT | ATA | 1893 |
| Phe | Asn | Met | Trp | Lys | Asn | Asp | Met | Val | Glu | Gln | Met | His | Glu | Asp | Ile | |
| | | 100 | | | | | 105 | | | | | 110 | | | | |
| ATC | AGT | TTA | TGG | GAT | CAA | AGC | CTA | AAG | CCA | TGT | GTA | AAA | TTA | ACC | CCA | 1941 |
| Ile | Ser | Leu | Trp | Asp | Gln | Ser | Leu | Lys | Pro | Cys | Val | Lys | Leu | Thr | Pro | |
| | 115 | | | | | 120 | | | | | 125 | | | | | |
| CTC | TGT | GTT | AGT | TTA | AAG | TGC | ACT | GAT | TTG | GGG | AAT | GCT | ACT | AAT | ACC | 1989 |
| Leu | Cys | Val | Ser | Leu | Lys | Cys | Thr | Asp | Leu | Gly | Asn | Ala | Thr | Asn | Thr | |
| 130 | | | | | 135 | | | | | 140 | | | | | 145 | |
| AAT | AGT | AGT | AAT | ACC | AAT | AGT | AGT | AGC | GGG | GAA | ATG | ATG | ATG | GAG | AAA | 2037 |
| Asn | Ser | Ser | Asn | Thr | Asn | Ser | Ser | Ser | Gly | Glu | Met | Met | Met | Glu | Lys | |
| | | | | 150 | | | | | 155 | | | | | 160 | | |
| GGA | GAG | ATA | AAA | AAC | TGC | TCT | TTC | AAT | ATC | AGC | ACA | AGC | ATA | AGA | GGT | 2085 |
| Gly | Glu | Ile | Lys | Asn | Cys | Ser | Phe | Asn | Ile | Ser | Thr | Ser | Ile | Arg | Gly | |
| | | | 165 | | | | | 170 | | | | | 175 | | | |
| AAG | GTG | CAG | AAA | GAA | TAT | GCA | TTT | TTT | TAT | AAA | CTT | GAT | ATA | ATA | CCA | 2133 |
| Lys | Val | Gln | Lys | Glu | Tyr | Ala | Phe | Phe | Tyr | Lys | Leu | Asp | Ile | Ile | Pro | |
| | | 180 | | | | | 185 | | | | | 190 | | | | |
| ATA | GAT | AAT | GAT | ACT | ACC | AGC | TAT | ACG | TTG | ACA | AGT | TGT | AAC | ACC | TCA | 2181 |
| Ile | Asp | Asn | Asp | Thr | Thr | Ser | Tyr | Thr | Leu | Thr | Ser | Cys | Asn | Thr | Ser | |
| | 195 | | | | | 200 | | | | | 205 | | | | | |
| GTC | ATT | ACA | CAG | GCC | TGT | CCA | AAG | GTA | TCC | TTT | GAG | CCA | ATT | CCC | ATA | 2229 |
| Val | Ile | Thr | Gln | Ala | Cys | Pro | Lys | Val | Ser | Phe | Glu | Pro | Ile | Pro | Ile | |
| 210 | | | | | 215 | | | | | 220 | | | | | 225 | |
| CAT | TAT | TGT | GCC | CCG | GCT | GGT | TTT | GCG | ATT | CTA | AAA | TGT | AAT | AAT | AAG | 2277 |
| His | Tyr | Cys | Ala | Pro | Ala | Gly | Phe | Ala | Ile | Leu | Lys | Cys | Asn | Asn | Lys | |
| | | | | 230 | | | | | 235 | | | | | 240 | | |
| ACG | TTC | AAT | GGA | ACA | GGA | CCA | TGT | ACA | AAT | GTC | AGC | ACA | GTA | CAA | TGT | 2325 |
| Thr | Phe | Asn | Gly | Thr | Gly | Pro | Cys | Thr | Asn | Val | Ser | Thr | Val | Gln | Cys | |
| | | | 245 | | | | | 250 | | | | | 255 | | | |
| ACA | CAT | GGA | ATT | AGG | CCA | GTA | GTA | TCA | ACT | CAA | CTG | CTG | TTG | AAT | GGC | 2373 |
| Thr | His | Gly | Ile | Arg | Pro | Val | Val | Ser | Thr | Gln | Leu | Leu | Leu | Asn | Gly | |
| | | | 260 | | | | | 265 | | | | | 270 | | | |
| AGT | CTA | GCA | GAA | GAA | GAG | GTA | GTA | ATT | AGA | TCT | GCC | AAT | TTC | ACA | GAC | 2421 |

|  |  |  |  |  |  |  |  |  |  |  |  |  |  |  |
|---|---|---|---|---|---|---|---|---|---|---|---|---|---|---|
| Ser | Leu | Ala | Glu | Glu | Glu | Val | Val | Ile | Arg | Ser | Ala | Asn | Phe | Thr | Asp |
| 275 |  |  |  |  | 280 |  |  |  |  | 285 |  |  |  |  |

| AAT | GCT | AAA | ACC | ATA | ATA | GTA | CAG | CTG | AAC | CAA | TCT | GTA | GAA | ATT | AAT | 2469 |
|---|---|---|---|---|---|---|---|---|---|---|---|---|---|---|---|---|
| Asn | Ala | Lys | Thr | Ile | Ile | Val | Gln | Leu | Asn | Gln | Ser | Val | Glu | Ile | Asn |  |
| 290 |  |  |  |  | 295 |  |  |  |  | 300 |  |  |  |  | 305 |  |

| TGT | ACA | AGA | CCC | AAC | AAC | AAT | ACA | AGA | AAA | AGT | ATC | CGT | ATC | CAG | AGG | 2517 |
|---|---|---|---|---|---|---|---|---|---|---|---|---|---|---|---|---|
| Cys | Thr | Arg | Pro | Asn | Asn | Asn | Thr | Arg | Lys | Ser | Ile | Arg | Ile | Gln | Arg |  |
|  |  |  |  |  | 310 |  |  |  |  | 315 |  |  |  |  | 320 |  |

| GGA | CCA | GGG | AGA | GCA | TTT | GTT | ACA | ATA | GGA | AAA | ATA | GGA | AAT | ATG | AGA | 2565 |
|---|---|---|---|---|---|---|---|---|---|---|---|---|---|---|---|---|
| Gly | Pro | Gly | Arg | Ala | Phe | Val | Thr | Ile | Gly | Lys | Ile | Gly | Asn | Met | Arg |  |
|  |  |  | 325 |  |  |  |  |  | 330 |  |  |  |  | 335 |  |  |

| CAA | GCA | CAT | TGT | AAC | ATT | AGT | AGA | GCA | AAA | TGG | AAT | GCC | ACT | TTA | AAA | 2613 |
|---|---|---|---|---|---|---|---|---|---|---|---|---|---|---|---|---|
| Gln | Ala | His | Cys | Asn | Ile | Ser | Arg | Ala | Lys | Trp | Asn | Ala | Thr | Leu | Lys |  |
|  |  | 340 |  |  |  |  | 345 |  |  |  |  | 350 |  |  |  |  |

| CAG | ATA | GCT | AGC | AAA | TTA | AGA | GAA | CAA | TTT | GGA | AAT | AAT | AAA | ACA | ATA | 2661 |
|---|---|---|---|---|---|---|---|---|---|---|---|---|---|---|---|---|
| Gln | Ile | Ala | Ser | Lys | Leu | Arg | Glu | Gln | Phe | Gly | Asn | Asn | Lys | Thr | Ile |  |
|  |  | 355 |  |  |  |  | 360 |  |  |  |  | 365 |  |  |  |  |

| ATC | TTT | AAG | CAA | TCC | TCA | GGA | GGG | GAC | CCA | GAA | ATT | GTA | ACG | CAC | AGT | 2709 |
|---|---|---|---|---|---|---|---|---|---|---|---|---|---|---|---|---|
| Ile | Phe | Lys | Gln | Ser | Ser | Gly | Gly | Asp | Pro | Glu | Ile | Val | Thr | His | Ser |  |
| 370 |  |  |  |  | 375 |  |  |  |  | 380 |  |  |  |  | 385 |  |

| TTT | AAT | TGT | GGA | GGG | GAA | TTT | TTC | TAC | TGT | AAT | TCA | ACA | CAA | CTG | TTT | 2757 |
|---|---|---|---|---|---|---|---|---|---|---|---|---|---|---|---|---|
| Phe | Asn | Cys | Gly | Gly | Glu | Phe | Phe | Tyr | Cys | Asn | Ser | Thr | Gln | Leu | Phe |  |
|  |  |  |  | 390 |  |  |  |  | 395 |  |  |  |  | 400 |  |  |

| AAT | AGT | ACT | TGG | TTT | AAT | AGT | ACT | TGG | AGT | ACT | GAA | GGG | TCA | AAT | AAC | 2805 |
|---|---|---|---|---|---|---|---|---|---|---|---|---|---|---|---|---|
| Asn | Ser | Thr | Trp | Phe | Asn | Ser | Thr | Trp | Ser | Thr | Glu | Gly | Ser | Asn | Asn |  |
|  |  |  | 405 |  |  |  |  | 410 |  |  |  |  | 415 |  |  |  |

| ACT | GAA | GGA | AGT | GAC | ACA | ATC | ACA | CTC | CCA | TGC | AGA | ATA | AAA | CAA | TTT | 2853 |
|---|---|---|---|---|---|---|---|---|---|---|---|---|---|---|---|---|
| Thr | Glu | Gly | Ser | Asp | Thr | Ile | Thr | Leu | Pro | Cys | Arg | Ile | Lys | Gln | Phe |  |
|  |  | 420 |  |  |  |  | 425 |  |  |  |  | 430 |  |  |  |  |

| ATA | AAC | ATG | TGG | CAG | GAA | GTA | GGA | AAA | GCA | ATG | TAT | GCC | CCT | CCC | ATC | 2901 |
|---|---|---|---|---|---|---|---|---|---|---|---|---|---|---|---|---|
| Ile | Asn | Met | Trp | Gln | Glu | Val | Gly | Lys | Ala | Met | Tyr | Ala | Pro | Pro | Ile |  |
|  | 435 |  |  |  |  | 440 |  |  |  |  | 445 |  |  |  |  |  |

| AGC | GGA | CAA | ATT | AGA | TGT | TCA | TCA | AAT | ATT | ACA | GGG | CTG | CTA | TTA | ACA | 2949 |
|---|---|---|---|---|---|---|---|---|---|---|---|---|---|---|---|---|
| Ser | Gly | Gln | Ile | Arg | Cys | Ser | Ser | Asn | Ile | Thr | Gly | Leu | Leu | Leu | Thr |  |
| 450 |  |  |  |  | 455 |  |  |  |  | 460 |  |  |  |  | 465 |  |

| AGA | GAT | GGT | GGT | AAT | AAC | AAC | AAT | GGG | TCC | GAG | ATC | TTC | AGA | CCT | GGA | 2997 |
|---|---|---|---|---|---|---|---|---|---|---|---|---|---|---|---|---|
| Arg | Asp | Gly | Gly | Asn | Asn | Asn | Asn | Gly | Ser | Glu | Ile | Phe | Arg | Pro | Gly |  |
|  |  |  |  | 470 |  |  |  |  | 475 |  |  |  |  | 480 |  |  |

| GGA | GGA | GAT | ATG | AGG | GAC | AAT | TGG | AGA | AGT | GAA | TTA | TAT | AAA | TAT | AAA | 3045 |
|---|---|---|---|---|---|---|---|---|---|---|---|---|---|---|---|---|
| Gly | Gly | Asp | Met | Arg | Asp | Asn | Trp | Arg | Ser | Glu | Leu | Tyr | Lys | Tyr | Lys |  |
|  |  |  | 485 |  |  |  |  | 490 |  |  |  |  | 495 |  |  |  |

| GTA | GTA | AAA | ATT | GAA | CCA | TTA | GGA | GTA | GCA | CCC | ACC | AAG | GCA | AAG | AGA | 3093 |
|---|---|---|---|---|---|---|---|---|---|---|---|---|---|---|---|---|
| Val | Val | Lys | Ile | Glu | Pro | Leu | Gly | Val | Ala | Pro | Thr | Lys | Ala | Lys | Arg |  |
|  |  | 500 |  |  |  |  | 505 |  |  |  |  | 510 |  |  |  |  |

| AGA | GTG | GTG | CAG | AGA | GAA | AAA | T | GAGCGGCCGC |  |  |  |  |  |  |  | 3125 |
|---|---|---|---|---|---|---|---|---|---|---|---|---|---|---|---|---|
| Arg | Val | Val | Gln | Arg | Glu | Lys |  |  |  |  |  |  |  |  |  |  |
|  | 515 |  |  |  |  | 520 |  |  |  |  |  |  |  |  |  |  |

( 2 ) INFORMATION FOR SEQ ID NO:14:

( i ) SEQUENCE CHARACTERISTICS:
        ( A ) LENGTH: 520 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| Met | Asp | Ala | Met | Lys | Arg | Gly | Leu | Cys | Cys | Val | Leu | Leu | Leu | Cys | Gly |
|---|---|---|---|---|---|---|---|---|---|---|---|---|---|---|---|
| 1 |  |  |  | 5 |  |  |  |  | 10 |  |  |  |  | 15 |  |

| Ala | Val | Phe | Val | Ser | Pro | Ser | Gln | Glu | Ile | His | Ala | Arg | Phe | Arg | Arg |
|---|---|---|---|---|---|---|---|---|---|---|---|---|---|---|---|
|  |  |  | 20 |  |  |  |  | 25 |  |  |  |  | 30 |  |  |

-continued

```
Gly  Ala  Arg  Thr  Glu  Lys  Leu  Trp  Val  Thr  Val  Tyr  Tyr  Gly  Val  Pro
          35                  40                       45

Val  Trp  Lys  Glu  Ala  Thr  Thr  Thr  Leu  Phe  Cys  Ala  Ser  Asp  Ala  Lys
     50                  55                       60

Ala  Tyr  Asp  Thr  Glu  Val  His  Asn  Val  Trp  Ala  Thr  His  Ala  Cys  Val
65                       70                  75                            80

Pro  Thr  Asp  Pro  Asn  Pro  Gln  Glu  Val  Val  Leu  Val  Asn  Val  Thr  Glu
               85                       90                            95

Asn  Phe  Asn  Met  Trp  Lys  Asn  Asp  Met  Val  Glu  Gln  Met  His  Glu  Asp
               100                 105                      110

Ile  Ile  Ser  Leu  Trp  Asp  Gln  Ser  Leu  Lys  Pro  Cys  Val  Lys  Leu  Thr
               115                 120                      125

Pro  Leu  Cys  Val  Ser  Leu  Lys  Cys  Thr  Asp  Leu  Gly  Asn  Ala  Thr  Asn
     130                      135                      140

Thr  Asn  Ser  Ser  Asn  Thr  Asn  Ser  Ser  Ser  Gly  Glu  Met  Met  Met  Glu
145                           150                      155                    160

Lys  Gly  Glu  Ile  Lys  Asn  Cys  Ser  Phe  Asn  Ile  Ser  Thr  Ser  Ile  Arg
                    165                 170                      175

Gly  Lys  Val  Gln  Lys  Glu  Tyr  Ala  Phe  Phe  Tyr  Lys  Leu  Asp  Ile  Ile
               180                      185                      190

Pro  Ile  Asp  Asn  Asp  Thr  Thr  Ser  Tyr  Thr  Leu  Thr  Ser  Cys  Asn  Thr
          195                      200                      205

Ser  Val  Ile  Thr  Gln  Ala  Cys  Pro  Lys  Val  Ser  Phe  Glu  Pro  Ile  Pro
     210                      215                      220

Ile  His  Tyr  Cys  Ala  Pro  Ala  Gly  Phe  Ala  Ile  Leu  Lys  Cys  Asn  Asn
225                      230                      235                         240

Lys  Thr  Phe  Asn  Gly  Thr  Gly  Pro  Cys  Thr  Asn  Val  Ser  Thr  Val  Gln
               245                      250                      255

Cys  Thr  His  Gly  Ile  Arg  Pro  Val  Val  Ser  Thr  Gln  Leu  Leu  Leu  Asn
               260                      265                      270

Gly  Ser  Leu  Ala  Glu  Glu  Glu  Val  Val  Ile  Arg  Ser  Ala  Asn  Phe  Thr
          275                      280                      285

Asp  Asn  Ala  Lys  Thr  Ile  Ile  Val  Gln  Leu  Asn  Gln  Ser  Val  Glu  Ile
290                      295                      300

Asn  Cys  Thr  Arg  Pro  Asn  Asn  Thr  Arg  Lys  Ser  Ile  Arg  Ile  Gln
305                      310                      315                         320

Arg  Gly  Pro  Gly  Arg  Ala  Phe  Val  Thr  Ile  Gly  Lys  Ile  Gly  Asn  Met
               325                      330                      335

Arg  Gln  Ala  His  Cys  Asn  Ile  Ser  Arg  Ala  Lys  Trp  Asn  Ala  Thr  Leu
               340                      345                      350

Lys  Gln  Ile  Ala  Ser  Lys  Leu  Arg  Glu  Gln  Phe  Gly  Asn  Asn  Lys  Thr
          355                      360                      365

Ile  Ile  Phe  Lys  Gln  Ser  Ser  Gly  Gly  Asp  Pro  Glu  Ile  Val  Thr  His
     370                      375                      380

Ser  Phe  Asn  Cys  Gly  Gly  Glu  Phe  Phe  Tyr  Cys  Asn  Ser  Thr  Gln  Leu
385                      390                      395                         400

Phe  Asn  Ser  Thr  Trp  Phe  Asn  Ser  Thr  Trp  Ser  Thr  Glu  Gly  Ser  Asn
               405                      410                      415

Asn  Thr  Glu  Gly  Ser  Asp  Thr  Ile  Thr  Leu  Pro  Cys  Arg  Ile  Lys  Gln
               420                      425                      430

Phe  Ile  Asn  Met  Trp  Gln  Glu  Val  Gly  Lys  Ala  Met  Tyr  Ala  Pro  Pro
          435                      440                      445

Ile  Ser  Gly  Gln  Ile  Arg  Cys  Ser  Ser  Asn  Ile  Thr  Gly  Leu  Leu  Leu
```

|       |       |       | 450   |       |       |       | 455   |       |       |       | 460   |       |       |       |
|-------|-------|-------|-------|-------|-------|-------|-------|-------|-------|-------|-------|-------|-------|-------|
| Thr   | Arg   | Asp   | Gly   | Gly   | Asn   | Asn   | Asn   | Asn   | Gly   | Ser   | Glu   | Ile   | Phe   | Arg   | Pro   |
| 465   |       |       |       |       | 470   |       |       |       | 475   |       |       |       |       | 480   |

| Gly | Gly | Gly | Asp | Met | Arg | Asp | Asn | Trp | Arg | Ser | Glu | Leu | Tyr | Lys | Tyr |
|-----|-----|-----|-----|-----|-----|-----|-----|-----|-----|-----|-----|-----|-----|-----|-----|
|     |     |     |     | 485 |     |     |     | 490 |     |     |     |     | 495 |     |     |

| Lys | Val | Val | Lys | Ile | Glu | Pro | Leu | Gly | Val | Ala | Pro | Thr | Lys | Ala | Lys |
|-----|-----|-----|-----|-----|-----|-----|-----|-----|-----|-----|-----|-----|-----|-----|-----|
|     |     |     | 500 |     |     |     | 505 |     |     |     |     | 510 |     |     |     |

| Arg | Arg | Val | Val | Gln | Arg | Glu | Lys |
|-----|-----|-----|-----|-----|-----|-----|-----|
|     |     |     | 515 |     |     |     | 520 |

( 2 ) INFORMATION FOR SEQ ID NO:15:

( i ) SEQUENCE CHARACTERISTICS:
        ( A ) LENGTH: 1532 base pairs
        ( B ) TYPE: nucleic acid
        ( C ) STRANDEDNESS: single
        ( D ) TOPOLOGY: linear ( i i i ) MOLECULE TYPE: DNA (genomic)

( i x ) FEATURE:
        ( A ) NAME/KEY: CDS
        ( B ) LOCATION: 1..1522
        ( D ) OTHER INFORMATION:

( x i ) SEQUENCE DESCRIPTION: SEQ ID NO:15:

| ATG | GAT | GCA | ATG | AAG | AGA | GGG | CTC | TGC | TGT | GTG | CTG | CTG | CTG | TGT | GGA | 48 |
|-----|-----|-----|-----|-----|-----|-----|-----|-----|-----|-----|-----|-----|-----|-----|-----|----|
| Met | Asp | Ala | Met | Lys | Arg | Gly | Leu | Cys | Cys | Val | Leu | Leu | Leu | Cys | Gly |    |
| 1   |     |     |     | 5   |     |     |     |     | 10  |     |     |     |     | 15  |     |    |

| GCA | GTC | TTC | GTT | TCG | CCC | AGC | CAG | GAA | ATC | CAT | GCC | CGA | TTC | AGA | AGA | 96 |
|-----|-----|-----|-----|-----|-----|-----|-----|-----|-----|-----|-----|-----|-----|-----|-----|----|
| Ala | Val | Phe | Val | Ser | Pro | Ser | Gln | Glu | Ile | His | Ala | Arg | Phe | Arg | Arg |    |
|     |     |     | 20  |     |     |     | 25  |     |     |     | 30  |     |     |     |     |    |

| GGC | GGC | AGA | GTA | GAA | AAG | TTG | TGG | GTC | ACA | GTC | TAT | TAT | GGG | GTA | CCT | 144 |
|-----|-----|-----|-----|-----|-----|-----|-----|-----|-----|-----|-----|-----|-----|-----|-----|-----|
| Gly | Gly | Arg | Val | Glu | Lys | Leu | Trp | Val | Thr | Val | Tyr | Tyr | Gly | Val | Pro |     |
|     |     | 35  |     |     |     | 40  |     |     |     | 45  |     |     |     |     |     |     |

| GTG | TGG | AAA | GAA | GCA | ACC | ACC | ACT | CTA | TTT | TGT | GCA | TCA | GAT | GCT | AAA | 192 |
|-----|-----|-----|-----|-----|-----|-----|-----|-----|-----|-----|-----|-----|-----|-----|-----|-----|
| Val | Trp | Lys | Glu | Ala | Thr | Thr | Thr | Leu | Phe | Cys | Ala | Ser | Asp | Ala | Lys |     |
|     | 50  |     |     |     | 55  |     |     |     | 60  |     |     |     |     |     |     |     |

| GCA | TAT | GAT | ACA | GAG | GTA | CAT | AAT | GTT | TGG | GCC | ACA | CAT | GCC | TGT | GTA | 240 |
|-----|-----|-----|-----|-----|-----|-----|-----|-----|-----|-----|-----|-----|-----|-----|-----|-----|
| Ala | Tyr | Asp | Thr | Glu | Val | His | Asn | Val | Trp | Ala | Thr | His | Ala | Cys | Val |     |
| 65  |     |     |     | 70  |     |     |     | 75  |     |     |     |     |     | 80  |     |     |

| CCC | ACA | GAC | CCC | AAC | CCA | CAA | GAA | GTA | GTA | TTG | GAA | AAT | GTA | ACA | GAA | 288 |
|-----|-----|-----|-----|-----|-----|-----|-----|-----|-----|-----|-----|-----|-----|-----|-----|-----|
| Pro | Thr | Asp | Pro | Asn | Pro | Gln | Glu | Val | Val | Leu | Glu | Asn | Val | Thr | Glu |     |
|     |     |     |     | 85  |     |     |     | 90  |     |     |     |     | 95  |     |     |     |

| CAT | TTT | AAC | ATG | TGG | AAA | AAT | AAC | ATG | GTA | GAA | CAG | ATG | CAG | GAG | GAT | 336 |
|-----|-----|-----|-----|-----|-----|-----|-----|-----|-----|-----|-----|-----|-----|-----|-----|-----|
| His | Phe | Asn | Met | Trp | Lys | Asn | Asn | Met | Val | Glu | Gln | Met | Gln | Glu | Asp |     |
|     |     |     | 100 |     |     |     | 105 |     |     |     | 110 |     |     |     |     |     |

| ATA | ATC | AGT | TTA | TGG | GAT | CAA | AGC | CTA | AAG | CCA | TGT | GTA | AAA | TTA | ACC | 384 |
|-----|-----|-----|-----|-----|-----|-----|-----|-----|-----|-----|-----|-----|-----|-----|-----|-----|
| Ile | Ile | Ser | Leu | Trp | Asp | Gln | Ser | Leu | Lys | Pro | Cys | Val | Lys | Leu | Thr |     |
|     |     | 115 |     |     |     | 120 |     |     |     | 125 |     |     |     |     |     |     |

| CCA | CTC | TGT | GTT | ACT | TTA | AAT | TGC | AAG | GAT | GTG | AAT | GCT | ACT | AAT | ACC | 432 |
|-----|-----|-----|-----|-----|-----|-----|-----|-----|-----|-----|-----|-----|-----|-----|-----|-----|
| Pro | Leu | Cys | Val | Thr | Leu | Asn | Cys | Lys | Asp | Val | Asn | Ala | Thr | Asn | Thr |     |
|     | 130 |     |     |     | 135 |     |     |     | 140 |     |     |     |     |     |     |     |

| ACT | AAT | GAT | AGC | GAG | GGA | ACG | ATG | GAG | AGA | GGA | GAA | ATA | AAA | AAC | TGC | 480 |
|-----|-----|-----|-----|-----|-----|-----|-----|-----|-----|-----|-----|-----|-----|-----|-----|-----|
| Thr | Asn | Asp | Ser | Glu | Gly | Thr | Met | Glu | Arg | Gly | Glu | Ile | Lys | Asn | Cys |     |
| 145 |     |     |     | 150 |     |     |     | 155 |     |     |     |     |     | 160 |     |     |

| TCT | TTC | AAT | ATC | ACC | ACA | AGC | ATA | AGA | GAT | GAG | GTG | CAG | AAA | GAA | TAT | 528 |
|-----|-----|-----|-----|-----|-----|-----|-----|-----|-----|-----|-----|-----|-----|-----|-----|-----|
| Ser | Phe | Asn | Ile | Thr | Thr | Ser | Ile | Arg | Asp | Glu | Val | Gln | Lys | Glu | Tyr |     |
|     |     |     | 165 |     |     |     | 170 |     |     |     | 175 |     |     |     |     |     |

| GCT | CTT | TTT | TAT | AAA | CTT | GAT | GTA | GTA | CCA | ATA | GAT | AAT | AAT | AAT | ACC | 576 |
|-----|-----|-----|-----|-----|-----|-----|-----|-----|-----|-----|-----|-----|-----|-----|-----|-----|
| Ala | Leu | Phe | Tyr | Lys | Leu | Asp | Val | Val | Pro | Ile | Asp | Asn | Asn | Asn | Thr |     |
|     |     |     | 180 |     |     |     | 185 |     |     |     | 190 |     |     |     |     |     |

| | | | | | | | | | | | | | | | | |
|---|---|---|---|---|---|---|---|---|---|---|---|---|---|---|---|---|
| AGC | TAT | AGG | TTG | ATA | AGT | TGT | GAC | ACC | TCA | GTC | ATT | ACA | CAG | GCC | TGT | 624 |
| Ser | Tyr | Arg | Leu | Ile | Ser | Cys | Asp | Thr | Ser | Val | Ile | Thr | Gln | Ala | Cys | |
| | | 195 | | | | | 200 | | | | | 205 | | | | |
| CCA | AAG | ATA | TCC | TTT | GAG | CCA | ATT | CCC | ATA | CAT | TAT | TGT | GCC | CCG | GCT | 672 |
| Pro | Lys | Ile | Ser | Phe | Glu | Pro | Ile | Pro | Ile | His | Tyr | Cys | Ala | Pro | Ala | |
| | 210 | | | | | 215 | | | | | 220 | | | | | |
| GGT | TTT | GCG | ATT | CTA | AAG | TGT | AAT | GAT | AAG | ACG | TTC | AAT | GGA | AAA | GGA | 720 |
| Gly | Phe | Ala | Ile | Leu | Lys | Cys | Asn | Asp | Lys | Thr | Phe | Asn | Gly | Lys | Gly | |
| 225 | | | | | 230 | | | | | 235 | | | | | 240 | |
| CCA | TGT | AAA | AAT | GTC | AGC | ACA | GTA | CAA | TGT | ACA | CAT | GGA | ATT | AGG | CCA | 768 |
| Pro | Cys | Lys | Asn | Val | Ser | Thr | Val | Gln | Cys | Thr | His | Gly | Ile | Arg | Pro | |
| | | | | 245 | | | | | 250 | | | | | 255 | | |
| GTA | GTA | TCA | ACT | CAA | CTG | CTG | CTA | AAT | GGC | AGT | CTA | GCA | GAA | GAA | GAG | 816 |
| Val | Val | Ser | Thr | Gln | Leu | Leu | Leu | Asn | Gly | Ser | Leu | Ala | Glu | Glu | Glu | |
| | | | 260 | | | | | 265 | | | | | 270 | | | |
| GTA | GTA | ATT | AGA | TCT | GAC | AAT | TTC | ACG | AAC | AAT | GCT | AAA | ACC | ATA | ATA | 864 |
| Val | Val | Ile | Arg | Ser | Asp | Asn | Phe | Thr | Asn | Asn | Ala | Lys | Thr | Ile | Ile | |
| | | 275 | | | | | 280 | | | | | 285 | | | | |
| GTA | CAG | CTG | AAA | GAA | TCT | GTA | GAA | ATT | AAT | TGT | ACA | AGA | CCC | AAC | AAC | 912 |
| Val | Gln | Leu | Lys | Glu | Ser | Val | Glu | Ile | Asn | Cys | Thr | Arg | Pro | Asn | Asn | |
| | 290 | | | | | 295 | | | | | 300 | | | | | |
| AAT | ACA | AGA | AAA | AGT | ATA | CAT | ATA | GGA | CCA | GGG | AGA | GCA | TTT | TAT | ACT | 960 |
| Asn | Thr | Arg | Lys | Ser | Ile | His | Ile | Gly | Pro | Gly | Arg | Ala | Phe | Tyr | Thr | |
| 305 | | | | | 310 | | | | | 315 | | | | | 320 | |
| ACA | GGA | GAA | ATA | ATA | GGA | GAT | ATA | AGA | CAA | GCA | CAT | TGT | AAC | ATT | AGT | 1008 |
| Thr | Gly | Glu | Ile | Ile | Gly | Asp | Ile | Arg | Gln | Ala | His | Cys | Asn | Ile | Ser | |
| | | | | 325 | | | | | 330 | | | | | 335 | | |
| AGA | GCA | AAA | TGG | AAT | GAC | ACT | TTA | AAA | CAG | ATA | GTT | ATA | AAA | TTA | AGA | 1056 |
| Arg | Ala | Lys | Trp | Asn | Asp | Thr | Leu | Lys | Gln | Ile | Val | Ile | Lys | Leu | Arg | |
| | | | 340 | | | | | 345 | | | | | 350 | | | |
| GAA | CAA | TTT | GAG | AAT | AAA | ACA | ATA | GTC | TTT | AAT | CAC | TCC | TCA | GGA | GGG | 1104 |
| Glu | Gln | Phe | Glu | Asn | Lys | Thr | Ile | Val | Phe | Asn | His | Ser | Ser | Gly | Gly | |
| | | 355 | | | | | 360 | | | | | 365 | | | | |
| GAC | CCA | GAA | ATT | GTA | ATG | CAC | AGT | TTT | AAT | TGT | GGA | GGA | GAA | TTT | TTC | 1152 |
| Asp | Pro | Glu | Ile | Val | Met | His | Ser | Phe | Asn | Cys | Gly | Gly | Glu | Phe | Phe | |
| | 370 | | | | | 375 | | | | | 380 | | | | | |
| TAC | TGT | AAT | TCA | ACA | CAA | CTG | TTT | AAT | AGT | ACT | TGG | AAT | AAT | AAT | ACT | 1200 |
| Tyr | Cys | Asn | Ser | Thr | Gln | Leu | Phe | Asn | Ser | Thr | Trp | Asn | Asn | Asn | Thr | |
| 385 | | | | | 390 | | | | | 395 | | | | | 400 | |
| GAA | GGG | TCA | AAT | AAC | ACT | GAA | GGA | AAT | ACT | ATC | ACA | CTC | CCA | TGC | AGA | 1248 |
| Glu | Gly | Ser | Asn | Asn | Thr | Glu | Gly | Asn | Thr | Ile | Thr | Leu | Pro | Cys | Arg | |
| | | | | 405 | | | | | 410 | | | | | 415 | | |
| ATA | AAA | CAA | ATT | ATA | AAC | ATG | TGG | CAG | GAA | GTA | GGA | AAA | GCA | ATG | TAT | 1296 |
| Ile | Lys | Gln | Ile | Ile | Asn | Met | Trp | Gln | Glu | Val | Gly | Lys | Ala | Met | Tyr | |
| | | | 420 | | | | | 425 | | | | | 430 | | | |
| GCC | CCT | CCC | ATC | AGA | GGA | CAA | ATT | AGA | TGT | TCA | TCA | AAT | ATT | ACA | GGG | 1344 |
| Ala | Pro | Pro | Ile | Arg | Gly | Gln | Ile | Arg | Cys | Ser | Ser | Asn | Ile | Thr | Gly | |
| | | 435 | | | | | 440 | | | | | 445 | | | | |
| CTG | CTA | TTA | ACA | AGA | GAT | GGT | GGT | ATT | AAT | GAG | AAT | GGG | ACC | GAG | ATC | 1392 |
| Leu | Leu | Leu | Thr | Arg | Asp | Gly | Gly | Ile | Asn | Glu | Asn | Gly | Thr | Glu | Ile | |
| | | 450 | | | | | 455 | | | | | 460 | | | | |
| TTC | AGA | CCT | GGA | GGA | GGA | GAT | ATG | AGG | GAC | AAT | TGG | AGA | AGT | GAA | TTA | 1440 |
| Phe | Arg | Pro | Gly | Gly | Gly | Asp | Met | Arg | Asp | Asn | Trp | Arg | Ser | Glu | Leu | |
| 465 | | | | | 470 | | | | | 475 | | | | | 480 | |
| TAT | AAA | TAT | AAA | GTA | GTA | AAA | ATT | GAA | CCA | TTA | GGA | GTA | GCA | CCC | ACC | 1488 |
| Tyr | Lys | Tyr | Lys | Val | Val | Lys | Ile | Glu | Pro | Leu | Gly | Val | Ala | Pro | Thr | |
| | | | | 485 | | | | | 490 | | | | | 495 | | |
| AAG | GCA | AAG | AGA | AGA | GTG | GTG | CAA | AGA | GAA | AAA | T | GAGCGGCCGC | | | | 1532 |
| Lys | Ala | Lys | Arg | Arg | Val | Val | Gln | Arg | Glu | Lys | | | | | | |
| | | | 500 | | | | | 505 | | | | | | | | |

( 2 ) INFORMATION FOR SEQ ID NO:16:

( i ) SEQUENCE CHARACTERISTICS:
        ( A ) LENGTH: 507 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

```
Met Asp Ala Met Lys Arg Gly Leu Cys Cys Val Leu Leu Leu Cys Gly
 1               5                  10                  15
Ala Val Phe Val Ser Pro Ser Gln Glu Ile His Ala Arg Phe Arg Arg
                20                  25                  30
Gly Gly Arg Val Glu Lys Leu Trp Val Thr Val Tyr Tyr Gly Val Pro
            35                  40                  45
Val Trp Lys Glu Ala Thr Thr Thr Leu Phe Cys Ala Ser Asp Ala Lys
        50                  55                  60
Ala Tyr Asp Thr Glu Val His Asn Val Trp Ala Thr His Ala Cys Val
65                  70                  75                  80
Pro Thr Asp Pro Asn Pro Gln Glu Val Val Leu Glu Asn Val Thr Glu
                85                  90                  95
His Phe Asn Met Trp Lys Asn Asn Met Val Glu Gln Met Gln Glu Asp
                100                 105                 110
Ile Ile Ser Leu Trp Asp Gln Ser Leu Lys Pro Cys Val Lys Leu Thr
            115                 120                 125
Pro Leu Cys Val Thr Leu Asn Cys Lys Asp Val Asn Ala Thr Asn Thr
        130                 135                 140
Thr Asn Asp Ser Glu Gly Thr Met Glu Arg Gly Glu Ile Lys Asn Cys
145                 150                 155                 160
Ser Phe Asn Ile Thr Thr Ser Ile Arg Asp Glu Val Gln Lys Glu Tyr
                165                 170                 175
Ala Leu Phe Tyr Lys Leu Asp Val Val Pro Ile Asp Asn Asn Asn Thr
            180                 185                 190
Ser Tyr Arg Leu Ile Ser Cys Asp Thr Ser Val Ile Thr Gln Ala Cys
        195                 200                 205
Pro Lys Ile Ser Phe Glu Pro Ile Pro Ile His Tyr Cys Ala Pro Ala
        210                 215                 220
Gly Phe Ala Ile Leu Lys Cys Asn Asp Lys Thr Phe Asn Gly Lys Gly
225                 230                 235                 240
Pro Cys Lys Asn Val Ser Thr Val Gln Cys Thr His Gly Ile Arg Pro
                245                 250                 255
Val Val Ser Thr Gln Leu Leu Leu Asn Gly Ser Leu Ala Glu Glu Glu
            260                 265                 270
Val Val Ile Arg Ser Asp Asn Phe Thr Asn Asn Ala Lys Thr Ile Ile
        275                 280                 285
Val Gln Leu Lys Glu Ser Val Glu Ile Asn Cys Thr Arg Pro Asn Asn
    290                 295                 300
Asn Thr Arg Lys Ser Ile His Ile Gly Pro Gly Arg Ala Phe Tyr Thr
305                 310                 315                 320
Thr Gly Glu Ile Ile Gly Asp Ile Arg Gln Ala His Cys Asn Ile Ser
                325                 330                 335
Arg Ala Lys Trp Asn Asp Thr Leu Lys Gln Ile Val Ile Lys Leu Arg
            340                 345                 350
Glu Gln Phe Glu Asn Lys Thr Ile Val Phe Asn His Ser Ser Gly Gly
        355                 360                 365
```

| | | | | | | | | | | | | | | |
|---|---|---|---|---|---|---|---|---|---|---|---|---|---|---|
| Asp | Pro | Glu | Ile | Val | Met | His | Ser | Phe | Asn | Cys | Gly | Gly | Glu | Phe | Phe |
| | 370 | | | | | 375 | | | | | 380 | | | | |
| Tyr | Cys | Asn | Ser | Thr | Gln | Leu | Phe | Asn | Ser | Thr | Trp | Asn | Asn | Asn | Thr |
| 385 | | | | | 390 | | | | | 395 | | | | | 400 |
| Glu | Gly | Ser | Asn | Asn | Thr | Glu | Gly | Asn | Thr | Ile | Thr | Leu | Pro | Cys | Arg |
| | | | | 405 | | | | | 410 | | | | | 415 | |
| Ile | Lys | Gln | Ile | Ile | Asn | Met | Trp | Gln | Glu | Val | Gly | Lys | Ala | Met | Tyr |
| | | | 420 | | | | | 425 | | | | | 430 | | |
| Ala | Pro | Pro | Ile | Arg | Gly | Gln | Ile | Arg | Cys | Ser | Ser | Asn | Ile | Thr | Gly |
| | | 435 | | | | | 440 | | | | | 445 | | | |
| Leu | Leu | Leu | Thr | Arg | Asp | Gly | Gly | Ile | Asn | Glu | Asn | Gly | Thr | Glu | Ile |
| | 450 | | | | | 455 | | | | | 460 | | | | |
| Phe | Arg | Pro | Gly | Gly | Gly | Asp | Met | Arg | Asp | Asn | Trp | Arg | Ser | Glu | Leu |
| 465 | | | | | 470 | | | | | 475 | | | | | 480 |
| Tyr | Lys | Tyr | Lys | Val | Val | Lys | Ile | Glu | Pro | Leu | Gly | Val | Ala | Pro | Thr |
| | | | | 485 | | | | | 490 | | | | | 495 | |
| Lys | Ala | Lys | Arg | Arg | Val | Val | Gln | Arg | Glu | Lys | | | | | |
| | | | 500 | | | | | 505 | | | | | | | |

( 2 ) INFORMATION FOR SEQ ID NO:17:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1474
        ( D ) OTHER INFORMATION:

( x i ) SEQUENCE DESCRIPTION: SEQ ID NO:17:

| | | | | | | | | | | | | | | | |
|---|---|---|---|---|---|---|---|---|---|---|---|---|---|---|---|
| ATG | GAT | GCA | ATG | AAG | AGA | GGG | CTC | TGC | TGT | GTG | CTG | CTG | CTG | TGT | GGA | 48 |
| Met | Asp | Ala | Met | Lys | Arg | Gly | Leu | Cys | Cys | Val | Leu | Leu | Leu | Cys | Gly |
| 1 | | | | 5 | | | | | 10 | | | | | 15 | |
| GCA | GTC | TTC | GTT | TCG | CCC | AGC | CAG | GAA | ATC | CAT | GCC | CGA | TTC | AGA | AGA | 96 |
| Ala | Val | Phe | Val | Ser | Pro | Ser | Gln | Glu | Ile | His | Ala | Arg | Phe | Arg | Arg |
| | | | 20 | | | | | 25 | | | | | 30 | | |
| GGC | GCC | AGA | ACA | GAA | AAA | TTG | TGG | GTC | ACA | GTC | TAT | TAT | GGG | GTA | CCT | 144 |
| Gly | Ala | Arg | Thr | Glu | Lys | Leu | Trp | Val | Thr | Val | Tyr | Tyr | Gly | Val | Pro |
| | | 35 | | | | | 40 | | | | | 45 | | | |
| GTG | TGG | AAG | GAA | GCA | ACC | ACC | ACT | CTA | TTT | TGT | GCA | TCA | GAT | GCT | AAA | 192 |
| Val | Trp | Lys | Glu | Ala | Thr | Thr | Thr | Leu | Phe | Cys | Ala | Ser | Asp | Ala | Lys |
| | 50 | | | | | 55 | | | | | 60 | | | | |
| GCA | TAT | GAT | ACA | GAG | GTA | CAT | AAT | GTT | TGG | GCC | ACA | CAT | GCC | TGT | GTA | 240 |
| Ala | Tyr | Asp | Thr | Glu | Val | His | Asn | Val | Trp | Ala | Thr | His | Ala | Cys | Val |
| 65 | | | | | 70 | | | | | 75 | | | | | 80 |
| CCC | ACA | GAC | CCC | AAC | CCA | CAA | GAA | GTA | GTA | TTG | GTA | AAT | GTG | ACA | GAA | 288 |
| Pro | Thr | Asp | Pro | Asn | Pro | Gln | Glu | Val | Val | Leu | Val | Asn | Val | Thr | Glu |
| | | | | 85 | | | | | 90 | | | | | 95 | |
| AAT | TTT | AAC | ATG | TGG | AAA | AAT | GAC | ATG | GTA | GAA | CAG | ATG | CAT | GAG | GAT | 336 |
| Asn | Phe | Asn | Met | Trp | Lys | Asn | Asp | Met | Val | Glu | Gln | Met | His | Glu | Asp |
| | | | 100 | | | | | 105 | | | | | 110 | | |
| ATA | ATC | AGT | TTA | TGG | GAT | CAA | AGC | CTA | AAG | CCA | TGT | GTA | AAA | TTA | ACC | 384 |
| Ile | Ile | Ser | Leu | Trp | Asp | Gln | Ser | Leu | Lys | Pro | Cys | Val | Lys | Leu | Thr |
| | | 115 | | | | | 120 | | | | | 125 | | | |
| CCA | CTC | TGT | GTT | AGT | TTA | AAG | TGC | ACT | GAT | TTG | GGG | AAT | GCT | ACT | AAT | 432 |
| Pro | Leu | Cys | Val | Ser | Leu | Lys | Cys | Thr | Asp | Leu | Gly | Asn | Ala | Thr | Asn |

-continued

|  |  |  | 130 |  |  |  |  | 135 |  |  |  |  | 140 |  |  |  |
|---|---|---|---|---|---|---|---|---|---|---|---|---|---|---|---|---|
| ACC | AAT | AGT | AGT | AAT | ACC | AAT | AGT | AGT | AGC | GGG | GAA | ATG | ATG | ATG | GAG | 480 |
| Thr | Asn | Ser | Ser | Asn | Thr | Asn | Ser | Ser | Ser | Gly | Glu | Met | Met | Met | Glu |  |
| 145 |  |  |  |  | 150 |  |  |  |  | 155 |  |  |  |  | 160 |  |
| AAA | GGA | GAG | ATA | AAA | AAC | TGC | TCT | TTC | AAT | ATC | AGC | ACA | AGC | ATA | AGA | 528 |
| Lys | Gly | Glu | Ile | Lys | Asn | Cys | Ser | Phe | Asn | Ile | Ser | Thr | Ser | Ile | Arg |  |
|  |  |  |  | 165 |  |  |  |  | 170 |  |  |  |  | 175 |  |  |
| GGT | AAG | GTG | CAG | AAA | GAA | TAT | GCA | TTT | TTT | TAT | AAA | CTT | GAT | ATA | ATA | 576 |
| Gly | Lys | Val | Gln | Lys | Glu | Tyr | Ala | Phe | Phe | Tyr | Lys | Leu | Asp | Ile | Ile |  |
|  |  |  | 180 |  |  |  |  | 185 |  |  |  |  | 190 |  |  |  |
| CCA | ATA | GAT | AAT | GAT | ACT | ACC | AGC | TAT | ACG | TTG | ACA | AGT | TGT | AAC | ACC | 624 |
| Pro | Ile | Asp | Asn | Asp | Thr | Thr | Ser | Tyr | Thr | Leu | Thr | Ser | Cys | Asn | Thr |  |
|  |  | 195 |  |  |  |  | 200 |  |  |  |  | 205 |  |  |  |  |
| TCA | GTC | ATT | ACA | CAG | GCC | TGT | CCA | AAG | GTA | TCC | TTT | GAG | CCA | ATT | CCC | 672 |
| Ser | Val | Ile | Thr | Gln | Ala | Cys | Pro | Lys | Val | Ser | Phe | Glu | Pro | Ile | Pro |  |
| 210 |  |  |  |  | 215 |  |  |  |  | 220 |  |  |  |  |  |  |
| ATA | CAT | TAT | TGT | GCC | CCG | GCT | GGT | TTT | GCG | ATT | CTA | AAA | TGT | AAT | AAT | 720 |
| Ile | His | Tyr | Cys | Ala | Pro | Ala | Gly | Phe | Ala | Ile | Leu | Lys | Cys | Asn | Asn |  |
| 225 |  |  |  |  | 230 |  |  |  |  | 235 |  |  |  |  | 240 |  |
| AAG | ACG | TTC | AAT | GGA | ACA | GGA | CCA | TGT | ACA | AAT | GTC | AGC | ACA | GTA | CAA | 768 |
| Lys | Thr | Phe | Asn | Gly | Thr | Gly | Pro | Cys | Thr | Asn | Val | Ser | Thr | Val | Gln |  |
|  |  |  |  | 245 |  |  |  |  | 250 |  |  |  |  | 255 |  |  |
| TGT | ACA | CAT | GGA | ATT | AGG | CCA | GTA | GTA | TCA | ACT | CAA | CTG | CTG | TTG | AAT | 816 |
| Cys | Thr | His | Gly | Ile | Arg | Pro | Val | Val | Ser | Thr | Gln | Leu | Leu | Leu | Asn |  |
|  |  |  | 260 |  |  |  |  | 265 |  |  |  |  | 270 |  |  |  |
| GGC | AGT | CTA | GCA | GAA | GAA | GAG | GTA | GTA | ATT | AGA | TCT | GCC | AAT | TTC | ACA | 864 |
| Gly | Ser | Leu | Ala | Glu | Glu | Glu | Val | Val | Ile | Arg | Ser | Ala | Asn | Phe | Thr |  |
|  |  | 275 |  |  |  |  | 280 |  |  |  |  | 285 |  |  |  |  |
| GAC | AAT | GCT | AAA | ACC | ATA | ATA | GTA | CAG | CTG | AAC | CAA | TCT | GTA | GAA | ATT | 912 |
| Asp | Asn | Ala | Lys | Thr | Ile | Ile | Val | Gln | Leu | Asn | Gln | Ser | Val | Glu | Ile |  |
|  | 290 |  |  |  |  | 295 |  |  |  |  | 300 |  |  |  |  |  |
| AAT | TGT | ACA | GGT | GCT | GGA | CAT | TGT | AAC | ATT | AGT | AGA | GCA | AAA | TGG | AAT | 960 |
| Asn | Cys | Thr | Gly | Ala | Gly | His | Cys | Asn | Ile | Ser | Arg | Ala | Lys | Trp | Asn |  |
| 305 |  |  |  |  | 310 |  |  |  |  | 315 |  |  |  |  | 320 |  |
| GCC | ACT | TTA | AAA | CAG | ATA | GCT | AGC | AAA | TTA | AGA | GAA | CAA | TTT | GGA | AAT | 1008 |
| Ala | Thr | Leu | Lys | Gln | Ile | Ala | Ser | Lys | Leu | Arg | Glu | Gln | Phe | Gly | Asn |  |
|  |  |  |  | 325 |  |  |  |  | 330 |  |  |  |  | 335 |  |  |
| AAT | AAA | ACA | ATA | ATC | TTT | AAG | CAA | TCC | TCA | GGA | GGG | GAC | CCA | GAA | ATT | 1056 |
| Asn | Lys | Thr | Ile | Ile | Phe | Lys | Gln | Ser | Ser | Gly | Gly | Asp | Pro | Glu | Ile |  |
|  |  |  | 340 |  |  |  |  | 345 |  |  |  |  | 350 |  |  |  |
| GTA | ACG | CAC | AGT | TTT | AAT | TGT | GGA | GGG | GAA | TTT | TTC | TAC | TGT | AAT | TCA | 1104 |
| Val | Thr | His | Ser | Phe | Asn | Cys | Gly | Gly | Glu | Phe | Phe | Tyr | Cys | Asn | Ser |  |
|  |  | 355 |  |  |  |  | 360 |  |  |  |  | 365 |  |  |  |  |
| ACA | CAA | CTG | TTT | AAT | AGT | ACT | TGG | TTT | AAT | AGT | ACT | TGG | AGT | ACT | GAA | 1152 |
| Thr | Gln | Leu | Phe | Asn | Ser | Thr | Trp | Phe | Asn | Ser | Thr | Trp | Ser | Thr | Glu |  |
|  | 370 |  |  |  |  | 375 |  |  |  |  | 380 |  |  |  |  |  |
| GGG | TCA | AAT | AAC | ACT | GAA | GGA | AGT | GAC | ACA | ATC | ACA | CTC | CCA | TGC | AGA | 1200 |
| Gly | Ser | Asn | Asn | Thr | Glu | Gly | Ser | Asp | Thr | Ile | Thr | Leu | Pro | Cys | Arg |  |
| 385 |  |  |  |  | 390 |  |  |  |  | 395 |  |  |  |  | 400 |  |
| ATA | AAA | CAA | TTT | ATA | AAC | ATG | TGG | CAG | GAA | GTA | GGA | AAA | GCA | ATG | TAT | 1248 |
| Ile | Lys | Gln | Phe | Ile | Asn | Met | Trp | Gln | Glu | Val | Gly | Lys | Ala | Met | Tyr |  |
|  |  |  |  | 405 |  |  |  |  | 410 |  |  |  |  | 415 |  |  |
| GCC | CCT | CCC | ATC | AGC | GGA | CAA | ATT | AGA | TGT | TCA | TCA | AAT | ATT | ACA | GGG | 1296 |
| Ala | Pro | Pro | Ile | Ser | Gly | Gln | Ile | Arg | Cys | Ser | Ser | Asn | Ile | Thr | Gly |  |
|  |  |  | 420 |  |  |  |  | 425 |  |  |  |  | 430 |  |  |  |
| CTG | CTA | TTA | ACA | AGA | GAT | GGT | GGT | AAT | AAC | AAC | AAT | GGG | TCC | GAG | ATC | 1344 |
| Leu | Leu | Leu | Thr | Arg | Asp | Gly | Gly | Asn | Asn | Asn | Asn | Gly | Ser | Glu | Ile |  |
|  |  | 435 |  |  |  |  | 440 |  |  |  |  | 445 |  |  |  |  |
| TTC | AGA | CCT | GGA | GGA | GGA | GAT | ATG | AGG | GAC | AAT | TGG | AGA | AGT | GAA | TTA | 1392 |
| Phe | Arg | Pro | Gly | Gly | Gly | Asp | Met | Arg | Asp | Asn | Trp | Arg | Ser | Glu | Leu |  |

```
                   450                          455                          460
TAT  AAA  TAT  AAA  GTA  GTA  AAA  ATT  GAA  CCA  TTA  GGA  GTA  GCA  CCC  ACC              1440
Tyr  Lys  Tyr  Lys  Val  Val  Lys  Ile  Glu  Pro  Leu  Gly  Val  Ala  Pro  Thr
465                      470                          475                      480

AAG  GCA  AAG  AGA  AGA  GTG  GTG  CAG  AGA  GAA  AAA  T  GAGCGGCCGC                         1484
Lys  Ala  Lys  Arg  Arg  Val  Val  Gln  Arg  Glu  Lys
                    485                          490
```

( 2 ) INFORMATION FOR SEQ ID NO:18:

( i ) SEQUENCE CHARACTERISTICS:
        ( A ) LENGTH: 491 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Asp  Ala  Met  Lys  Arg  Gly  Leu  Cys  Cys  Val  Leu  Leu  Leu  Cys  Gly
 1                    5                        10                         15

Ala  Val  Phe  Val  Ser  Pro  Ser  Gln  Glu  Ile  His  Ala  Arg  Phe  Arg  Arg
               20                        25                        30

Gly  Ala  Arg  Thr  Glu  Lys  Leu  Trp  Val  Thr  Val  Tyr  Tyr  Gly  Val  Pro
                35                        40                        45

Val  Trp  Lys  Glu  Ala  Thr  Thr  Thr  Leu  Phe  Cys  Ala  Ser  Asp  Ala  Lys
          50                        55                        60

Ala  Tyr  Asp  Thr  Glu  Val  His  Asn  Val  Trp  Ala  Thr  His  Ala  Cys  Val
65                        70                        75                        80

Pro  Thr  Asp  Pro  Asn  Pro  Gln  Glu  Val  Val  Leu  Val  Asn  Val  Thr  Glu
                    85                        90                        95

Asn  Phe  Asn  Met  Trp  Lys  Asn  Asp  Met  Val  Glu  Gln  Met  His  Glu  Asp
               100                       105                       110

Ile  Ile  Ser  Leu  Trp  Asp  Gln  Ser  Leu  Lys  Pro  Cys  Val  Lys  Leu  Thr
               115                       120                       125

Pro  Leu  Cys  Val  Ser  Leu  Lys  Cys  Thr  Asp  Leu  Gly  Asn  Ala  Thr  Asn
     130                       135                       140

Thr  Asn  Ser  Ser  Asn  Thr  Asn  Ser  Ser  Ser  Gly  Glu  Met  Met  Met  Glu
145                       150                       155                       160

Lys  Gly  Glu  Ile  Lys  Asn  Cys  Ser  Phe  Asn  Ile  Ser  Thr  Ser  Ile  Arg
                    165                       170                       175

Gly  Lys  Val  Gln  Lys  Glu  Tyr  Ala  Phe  Phe  Tyr  Lys  Leu  Asp  Ile  Ile
               180                       185                       190

Pro  Ile  Asp  Asn  Asp  Thr  Thr  Ser  Tyr  Thr  Leu  Thr  Ser  Cys  Asn  Thr
               195                       200                       205

Ser  Val  Ile  Thr  Gln  Ala  Cys  Pro  Lys  Val  Ser  Phe  Glu  Pro  Ile  Pro
     210                       215                       220

Ile  His  Tyr  Cys  Ala  Pro  Ala  Gly  Phe  Ala  Ile  Leu  Lys  Cys  Asn  Asn
225                       230                       235                       240

Lys  Thr  Phe  Asn  Gly  Thr  Gly  Pro  Cys  Thr  Asn  Val  Ser  Thr  Val  Gln
                    245                       250                       255

Cys  Thr  His  Gly  Ile  Arg  Pro  Val  Val  Ser  Thr  Gln  Leu  Leu  Leu  Asn
               260                       265                       270

Gly  Ser  Leu  Ala  Glu  Glu  Glu  Val  Val  Ile  Arg  Ser  Ala  Asn  Phe  Thr
               275                       280                       285

Asp  Asn  Ala  Lys  Thr  Ile  Ile  Val  Gln  Leu  Asn  Gln  Ser  Val  Glu  Ile
     290                       295                       300

Asn  Cys  Thr  Gly  Ala  Gly  His  Cys  Asn  Ile  Ser  Arg  Ala  Lys  Trp  Asn
```

```
305                      310                      315                      320
Ala Thr Leu Lys Gln Ile Ala Ser Lys Leu Arg Glu Gln Phe Gly Asn
                325                      330                      335

Asn Lys Thr Ile Ile Phe Lys Gln Ser Ser Gly Gly Asp Pro Glu Ile
            340                      345                      350

Val Thr His Ser Phe Asn Cys Gly Gly Glu Phe Phe Tyr Cys Asn Ser
            355                      360                      365

Thr Gln Leu Phe Asn Ser Thr Trp Phe Asn Ser Thr Trp Ser Thr Glu
        370                      375                      380

Gly Ser Asn Asn Thr Glu Gly Ser Asp Thr Ile Thr Leu Pro Cys Arg
385                      390                      395                      400

Ile Lys Gln Phe Ile Asn Met Trp Gln Glu Val Gly Lys Ala Met Tyr
                405                      410                      415

Ala Pro Pro Ile Ser Gly Gln Ile Arg Cys Ser Ser Asn Ile Thr Gly
                420                      425                      430

Leu Leu Leu Thr Arg Asp Gly Gly Asn Asn Asn Asn Gly Ser Glu Ile
            435                      440                      445

Phe Arg Pro Gly Gly Gly Asp Met Arg Asp Asn Trp Arg Ser Glu Leu
        450                      455                      460

Tyr Lys Tyr Lys Val Val Lys Ile Glu Pro Leu Gly Val Ala Pro Thr
465                      470                      475                      480

Lys Ala Lys Arg Arg Val Val Gln Arg Glu Lys
                485                      490
```

( 2 ) INFORMATION FOR SEQ ID NO:19:

( i ) SEQUENCE CHARACTERISTICS:
        ( A ) LENGTH: 1448 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1439
        ( D ) OTHER INFORMATION:

( x i ) SEQUENCE DESCRIPTION: SEQ ID NO:19:

```
ATG GAT GCA ATG AAG AGA GGG CTC TGC TGT GTG CTG CTG CTG TGT GGA        48
Met Asp Ala Met Lys Arg Gly Leu Cys Cys Val Leu Leu Leu Cys Gly
 1               5                      10                      15

GCA GTC TTC GTT TCG CCC AGC CAG GAA ATC CAT GCC CGA TTC AGA AGA        96
Ala Val Phe Val Ser Pro Ser Gln Glu Ile His Ala Arg Phe Arg Arg
                20                      25                      30

GGC GGC AGA GTA GAA AAG TTG TGG GTC ACA GTC TAT TAT GGG GTA CCT       144
Gly Gly Arg Val Glu Lys Leu Trp Val Thr Val Tyr Tyr Gly Val Pro
            35                      40                      45

GTG TGG AAA GAA GCA ACC ACC ACT CTA TTT TGT GCA TCA GAT GCT AAA       192
Val Trp Lys Glu Ala Thr Thr Thr Leu Phe Cys Ala Ser Asp Ala Lys
        50                      55                      60

GCA TAT GAT ACA GAG GTA CAT AAT GTT TGG GCC ACA CAT GCC TGT GTA       240
Ala Tyr Asp Thr Glu Val His Asn Val Trp Ala Thr His Ala Cys Val
65                      70                      75                      80

CCC ACA GAC CCC AAC CCA CAA GAA GTA GTA TTG GAA AAT GTA ACA GAA       288
Pro Thr Asp Pro Asn Pro Gln Glu Val Val Leu Glu Asn Val Thr Glu
                85                      90                      95

CAT TTT AAC ATG TGG AAA AAT AAC ATG GTA GAA CAG ATG CAG GAG GAT       336
His Phe Asn Met Trp Lys Asn Asn Met Val Glu Gln Met Gln Glu Asp
                100                     105                     110
```

| | | | | | | | | | | | | | | | | |
|---|---|---|---|---|---|---|---|---|---|---|---|---|---|---|---|---|
|ATA|ATC|AGT|TTA|TGG|GAT|CAA|AGC|CTA|AAG|CCA|TGT|GTA|AAA|TTA|ACC|384|
|Ile|Ile|Ser|Leu|Trp|Asp|Gln|Ser|Leu|Lys|Pro|Cys|Val|Lys|Leu|Thr||
| | |115| | | |120| | | |125| | | | | | |
|CCA|CTC|TGT|GTT|ACT|TTA|AAT|TGC|AAG|GAT|GTG|AAT|GCT|ACT|AAT|ACC|432|
|Pro|Leu|Cys|Val|Thr|Leu|Asn|Cys|Lys|Asp|Val|Asn|Ala|Thr|Asn|Thr||
| |130| | | | |135| | | | |140| | | | | |
|ACT|AAT|GAT|AGC|GAG|GGA|ACG|ATG|GAG|AGA|GGA|GAA|ATA|AAA|AAC|TGC|480|
|Thr|Asn|Asp|Ser|Glu|Gly|Thr|Met|Glu|Arg|Gly|Glu|Ile|Lys|Asn|Cys||
|145| | | | |150| | | | |155| | | | |160| |
|TCT|TTC|AAT|ATC|ACC|ACA|AGC|ATA|AGA|GAT|GAG|GTG|CAG|AAA|GAA|TAT|528|
|Ser|Phe|Asn|Ile|Thr|Thr|Ser|Ile|Arg|Asp|Glu|Val|Gln|Lys|Glu|Tyr||
| | | | |165| | | | |170| | | | |175| | |
|GCT|CTT|TTT|TAT|AAA|CTT|GAT|GTA|GTA|CCA|ATA|GAT|AAT|AAT|AAT|ACC|576|
|Ala|Leu|Phe|Tyr|Lys|Leu|Asp|Val|Val|Pro|Ile|Asp|Asn|Asn|Asn|Thr||
| | | |180| | | | |185| | | | |190| | | |
|AGC|TAT|AGG|TTG|ATA|AGT|TGT|GAC|ACC|TCA|GTC|ATT|ACA|CAG|GCC|TGT|624|
|Ser|Tyr|Arg|Leu|Ile|Ser|Cys|Asp|Thr|Ser|Val|Ile|Thr|Gln|Ala|Cys||
| | | | |195| | | | |200| | | | |205| | |
|CCA|AAG|ATA|TCC|TTT|GAG|CCA|ATT|CCC|ATA|CAT|TAT|TGT|GCC|CCG|GCT|672|
|Pro|Lys|Ile|Ser|Phe|Glu|Pro|Ile|Pro|Ile|His|Tyr|Cys|Ala|Pro|Ala||
| |210| | | | |215| | | | |220| | | | | |
|GGT|TTT|GCG|ATT|CTA|AAG|TGT|AAT|GAT|AAG|ACG|TTC|AAT|GGA|AAA|GGA|720|
|Gly|Phe|Ala|Ile|Leu|Lys|Cys|Asn|Asp|Lys|Thr|Phe|Asn|Gly|Lys|Gly||
|225| | | | |230| | | | |235| | | | |240| |
|CCA|TGT|AAA|AAT|GTC|AGC|ACA|GTA|CAA|TGT|ACA|CAT|GGA|ATT|AGG|CCA|768|
|Pro|Cys|Lys|Asn|Val|Ser|Thr|Val|Gln|Cys|Thr|His|Gly|Ile|Arg|Pro||
| | | | |245| | | | |250| | | | |255| | |
|GTA|GTA|TCA|ACT|CAA|CTG|CTG|CTA|AAT|GGC|AGT|CTA|GCA|GAA|GAA|GAG|816|
|Val|Val|Ser|Thr|Gln|Leu|Leu|Leu|Asn|Gly|Ser|Leu|Ala|Glu|Glu|Glu||
| | | |260| | | | |265| | | | |270| | | |
|GTA|GTA|ATT|AGA|TCT|GAC|AAT|TTC|ACG|AAC|AAT|GCT|AAA|ACC|ATA|ATA|864|
|Val|Val|Ile|Arg|Ser|Asp|Asn|Phe|Thr|Asn|Asn|Ala|Lys|Thr|Ile|Ile||
| | |275| | | | |280| | | | |285| | | | |
|GTA|CAG|CTG|AAA|GAA|TCT|GTA|GAA|ATT|AAT|TGT|ACA|GGT|GCT|GGA|CAT|912|
|Val|Gln|Leu|Lys|Glu|Ser|Val|Glu|Ile|Asn|Cys|Thr|Gly|Ala|Gly|His||
| |290| | | | |295| | | | |300| | | | | |
|TGT|AAC|ATT|AGT|AGA|GCA|AAA|TGG|AAT|GAC|ACT|TTA|AAA|CAG|ATA|GTT|960|
|Cys|Asn|Ile|Ser|Arg|Ala|Lys|Trp|Asn|Asp|Thr|Leu|Lys|Gln|Ile|Val||
|305| | | | |310| | | | |315| | | | |320| |
|ATA|AAA|TTA|AGA|GAA|CAA|TTT|GAG|AAT|AAA|ACA|ATA|GTC|TTT|AAT|CAC|1008|
|Ile|Lys|Leu|Arg|Glu|Gln|Phe|Glu|Asn|Lys|Thr|Ile|Val|Phe|Asn|His||
| | | | |325| | | | |330| | | | |335| | |
|TCC|TCA|GGA|GGG|GAC|CCA|GAA|ATT|GTA|ATG|CAC|AGT|TTT|AAT|TGT|GGA|1056|
|Ser|Ser|Gly|Gly|Asp|Pro|Glu|Ile|Val|Met|His|Ser|Phe|Asn|Cys|Gly||
| | | |340| | | | |345| | | | |350| | | |
|GGA|GAA|TTT|TTC|TAC|TGT|AAT|TCA|ACA|CAA|CTG|TTT|AAT|AGT|ACT|TGG|1104|
|Gly|Glu|Phe|Phe|Tyr|Cys|Asn|Ser|Thr|Gln|Leu|Phe|Asn|Ser|Thr|Trp||
| | |355| | | | |360| | | | |365| | | | |
|AAT|AAT|AAT|ACT|GAA|GGG|TCA|AAT|AAC|ACT|GAA|GGA|AAT|ACT|ATC|ACA|1152|
|Asn|Asn|Asn|Thr|Glu|Gly|Ser|Asn|Asn|Thr|Glu|Gly|Asn|Thr|Ile|Thr||
| |370| | | | |375| | | | |380| | | | | |
|CTC|CCA|TGC|AGA|ATA|AAA|CAA|ATT|ATA|AAC|ATG|TGG|CAG|GAA|GTA|GGA|1200|
|Leu|Pro|Cys|Arg|Ile|Lys|Gln|Ile|Ile|Asn|Met|Trp|Gln|Glu|Val|Gly||
|385| | | | |390| | | | |395| | | | |400| |
|AAA|GCA|ATG|TAT|GCC|CCT|CCC|ATC|AGA|GGA|CAA|ATT|AGA|TGT|TCA|TCA|1248|
|Lys|Ala|Met|Tyr|Ala|Pro|Pro|Ile|Arg|Gly|Gln|Ile|Arg|Cys|Ser|Ser||
| | | | |405| | | | |410| | | | |415| | |
|AAT|ATT|ACA|GGG|CTG|CTA|TTA|ACA|AGA|GAT|GGT|GGT|ATT|AAT|GAG|AAT|1296|
|Asn|Ile|Thr|Gly|Leu|Leu|Leu|Thr|Arg|Asp|Gly|Gly|Ile|Asn|Glu|Asn||
| | | |420| | | | |425| | | | |430| | | |

```
GGG  ACC  GAG  ATC  TTC  AGA  CCT  GGA  GGA  GGA  GAT  ATG  AGG  GAC  AAT  TGG         1344
Gly  Thr  Glu  Ile  Phe  Arg  Pro  Gly  Gly  Gly  Asp  Met  Arg  Asp  Asn  Trp
          435                      440                      445

AGA  AGT  GAA  TTA  TAT  AAA  TAT  AAA  GTA  GTA  AAA  ATT  GAA  CCA  TTA  GGA         1392
Arg  Ser  Glu  Leu  Tyr  Lys  Tyr  Lys  Val  Val  Lys  Ile  Glu  Pro  Leu  Gly
     450                      455                           460

GTA  GCA  CCC  ACC  AAG  GCA  AAG  AGA  AGA  GTG  GTG  CAA  AGA  GAA  AAA  TG          1439
Val  Ala  Pro  Thr  Lys  Ala  Lys  Arg  Arg  Val  Val  Gln  Arg  Glu  Lys
465                      470                      475

AGCGGCCGC                                                                                1448
```

( 2 ) INFORMATION FOR SEQ ID NO:20:

( i ) SEQUENCE CHARACTERISTICS:
        ( A ) LENGTH: 479 amino acids
        ( B ) TYPE: amino acid
        ( D ) TOPOLOGY: linear ( i i ) MOLECULE TYPE: protein ( x i ) SEQUENCE DESCRIPTION: SEQ ID NO:20:

```
Met  Asp  Ala  Met  Lys  Arg  Gly  Leu  Cys  Cys  Val  Leu  Leu  Leu  Cys  Gly
 1              5                        10                       15

Ala  Val  Phe  Val  Ser  Pro  Ser  Gln  Glu  Ile  His  Ala  Arg  Phe  Arg  Arg
               20                       25                       30

Gly  Gly  Arg  Val  Glu  Lys  Leu  Trp  Val  Thr  Val  Tyr  Tyr  Gly  Val  Pro
          35                       40                       45

Val  Trp  Lys  Glu  Ala  Thr  Thr  Thr  Leu  Phe  Cys  Ala  Ser  Asp  Ala  Lys
     50                       55                       60

Ala  Tyr  Asp  Thr  Glu  Val  His  Asn  Val  Trp  Ala  Thr  His  Ala  Cys  Val
65                       70                       75                       80

Pro  Thr  Asp  Pro  Asn  Pro  Gln  Glu  Val  Val  Leu  Glu  Asn  Val  Thr  Glu
                    85                       90                       95

His  Phe  Asn  Met  Trp  Lys  Asn  Asn  Met  Val  Glu  Gln  Met  Gln  Glu  Asp
               100                      105                      110

Ile  Ile  Ser  Leu  Trp  Asp  Gln  Ser  Leu  Lys  Pro  Cys  Val  Lys  Leu  Thr
          115                      120                      125

Pro  Leu  Cys  Val  Thr  Leu  Asn  Cys  Lys  Asp  Val  Asn  Ala  Thr  Asn  Thr
     130                      135                      140

Thr  Asn  Asp  Ser  Glu  Gly  Thr  Met  Glu  Arg  Gly  Glu  Ile  Lys  Asn  Cys
145                      150                      155                      160

Ser  Phe  Asn  Ile  Thr  Thr  Ser  Ile  Arg  Asp  Glu  Val  Gln  Lys  Glu  Tyr
                    165                      170                      175

Ala  Leu  Phe  Tyr  Lys  Leu  Asp  Val  Val  Pro  Ile  Asp  Asn  Asn  Asn  Thr
               180                      185                      190

Ser  Tyr  Arg  Leu  Ile  Ser  Cys  Asp  Thr  Ser  Val  Ile  Thr  Gln  Ala  Cys
          195                      200                      205

Pro  Lys  Ile  Ser  Phe  Glu  Pro  Ile  Pro  Ile  His  Tyr  Cys  Ala  Pro  Ala
     210                      215                      220

Gly  Phe  Ala  Ile  Leu  Lys  Cys  Asn  Asp  Lys  Thr  Phe  Asn  Gly  Lys  Gly
225                      230                      235                      240

Pro  Cys  Lys  Asn  Val  Ser  Thr  Val  Gln  Cys  Thr  His  Gly  Ile  Arg  Pro
                    245                      250                      255

Val  Val  Ser  Thr  Gln  Leu  Leu  Leu  Asn  Gly  Ser  Leu  Ala  Glu  Glu  Glu
               260                      265                      270

Val  Val  Ile  Arg  Ser  Asp  Asn  Phe  Thr  Asn  Asn  Ala  Lys  Thr  Ile  Ile
          275                      280                      285
```

| | | | | | | | | | | | | | | |
|---|---|---|---|---|---|---|---|---|---|---|---|---|---|---|
| Val | Gln | Leu | Lys | Glu | Ser | Val | Glu | Ile | Asn | Cys | Thr | Gly | Ala | Gly | His |
| | 290 | | | | | 295 | | | | | 300 | | | | |
| Cys | Asn | Ile | Ser | Arg | Ala | Lys | Trp | Asn | Asp | Thr | Leu | Lys | Gln | Ile | Val |
| 305 | | | | | 310 | | | | | 315 | | | | | 320 |
| Ile | Lys | Leu | Arg | Glu | Gln | Phe | Glu | Asn | Lys | Thr | Ile | Val | Phe | Asn | His |
| | | | | 325 | | | | | 330 | | | | | 335 | |
| Ser | Ser | Gly | Gly | Asp | Pro | Glu | Ile | Val | Met | His | Ser | Phe | Asn | Cys | Gly |
| | | | 340 | | | | | 345 | | | | | 350 | | |
| Gly | Glu | Phe | Phe | Tyr | Cys | Asn | Ser | Thr | Gln | Leu | Phe | Asn | Ser | Thr | Trp |
| | | 355 | | | | | 360 | | | | | 365 | | | |
| Asn | Asn | Asn | Thr | Glu | Gly | Ser | Asn | Asn | Thr | Glu | Gly | Asn | Thr | Ile | Thr |
| | 370 | | | | | 375 | | | | | 380 | | | | |
| Leu | Pro | Cys | Arg | Ile | Lys | Gln | Ile | Ile | Asn | Met | Trp | Gln | Glu | Val | Gly |
| 385 | | | | | 390 | | | | | 395 | | | | | 400 |
| Lys | Ala | Met | Tyr | Ala | Pro | Pro | Ile | Arg | Gly | Gln | Ile | Arg | Cys | Ser | Ser |
| | | | | 405 | | | | | 410 | | | | | 415 | |
| Asn | Ile | Thr | Gly | Leu | Leu | Leu | Thr | Arg | Asp | Gly | Gly | Ile | Asn | Glu | Asn |
| | | | 420 | | | | | 425 | | | | | 430 | | |
| Gly | Thr | Glu | Ile | Phe | Arg | Pro | Gly | Gly | Gly | Asp | Met | Arg | Asp | Asn | Trp |
| | | 435 | | | | | 440 | | | | | 445 | | | |
| Arg | Ser | Glu | Leu | Tyr | Lys | Tyr | Lys | Val | Val | Lys | Ile | Glu | Pro | Leu | Gly |
| | 450 | | | | | 455 | | | | | 460 | | | | |
| Val | Ala | Pro | Thr | Lys | Ala | Lys | Arg | Arg | Val | Val | Gln | Arg | Glu | Lys | |
| 465 | | | | | 470 | | | | | 475 | | | | | |

( 2 ) INFORMATION FOR SEQ ID NO:21:

( i ) SEQUENCE CHARACTERISTICS:
        ( A ) LENGTH: 1484 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1454
        ( D ) OTHER INFORMATION:

( x i ) SEQUENCE DESCRIPTION: SEQ ID NO:21:

| | | | | | | | | | | | | | | | |
|---|---|---|---|---|---|---|---|---|---|---|---|---|---|---|---|
| ATG | GAT | GCA | ATG | AAG | AGA | GGG | CTC | TGC | TGT | GTG | CTG | CTG | CTG | TGT | GGA | 48 |
| Met | Asp | Ala | Met | Lys | Arg | Gly | Leu | Cys | Cys | Val | Leu | Leu | Leu | Cys | Gly | |
| 1 | | | | 5 | | | | | 10 | | | | | 15 | | |
| GCA | GTC | TTC | GTT | TCG | CCC | AGC | CAG | GAA | ATC | CAT | GCC | CGA | TTC | AGA | AGA | 96 |
| Ala | Val | Phe | Val | Ser | Pro | Ser | Gln | Glu | Ile | His | Ala | Arg | Phe | Arg | Arg | |
| | | | 20 | | | | | 25 | | | | | 30 | | | |
| GGC | GCC | AGA | ACA | GAA | AAA | TTG | TGG | GTC | ACA | GTC | TAT | TAT | GGG | GTA | CCT | 144 |
| Gly | Ala | Arg | Thr | Glu | Lys | Leu | Trp | Val | Thr | Val | Tyr | Tyr | Gly | Val | Pro | |
| | | 35 | | | | | 40 | | | | | 45 | | | | |
| GTG | TGG | AAG | GAA | GCA | ACC | ACC | ACT | CTA | TTT | TGT | GCA | TCA | GAT | GCT | AAA | 192 |
| Val | Trp | Lys | Glu | Ala | Thr | Thr | Thr | Leu | Phe | Cys | Ala | Ser | Asp | Ala | Lys | |
| | 50 | | | | | 55 | | | | | 60 | | | | | |
| GCA | TAT | GAT | ACA | GAG | GTA | CAT | AAT | GTT | TGG | GCC | ACA | CAT | GCC | TGT | GTA | 240 |
| Ala | Tyr | Asp | Thr | Glu | Val | His | Asn | Val | Trp | Ala | Thr | His | Ala | Cys | Val | |
| 65 | | | | | 70 | | | | | 75 | | | | | 80 | |
| CCC | ACA | GAC | CCC | AAC | CCA | CAA | GAA | GTA | GTA | TTG | GTA | AAT | GTG | ACA | GAA | 288 |
| Pro | Thr | Asp | Pro | Asn | Pro | Gln | Glu | Val | Val | Leu | Val | Asn | Val | Thr | Glu | |
| | | | | 85 | | | | | 90 | | | | | 95 | | |
| AAT | TTT | AAC | ATG | TGG | AAA | AAT | GAC | ATG | GTA | GAA | CAG | ATG | CAT | GAG | GAT | 336 |

```
            Asn  Phe  Asn  Met  Trp  Lys  Asn  Asp  Met  Val  Glu  Gln  Met  His  Glu  Asp
                           100                 105                           110

ATA  ATC  AGT  TTA  TGG  GAT  CAA  AGC  CTA  AAG  CCA  TGT  GTA  AAA  TTA  ACC                    384
Ile  Ile  Ser  Leu  Trp  Asp  Gln  Ser  Leu  Lys  Pro  Cys  Val  Lys  Leu  Thr
               115                      120                      125

CCA  CTC  TGT  GTT  AGT  TTA  AAG  TGC  ACT  GAT  TTG  GGG  AAT  GCT  ACT  AAT                    432
Pro  Leu  Cys  Val  Ser  Leu  Lys  Cys  Thr  Asp  Leu  Gly  Asn  Ala  Thr  Asn
          130                      135                      140

ACC  AAT  AGT  AGT  AAT  ACC  AAT  AGT  AGT  AGC  GGG  GAA  ATG  ATG  ATG  GAG                    480
Thr  Asn  Ser  Ser  Asn  Thr  Asn  Ser  Ser  Ser  Gly  Glu  Met  Met  Met  Glu
145                      150                      155                      160

AAA  GGA  GAG  ATA  AAA  AAC  TGC  TCT  TTC  AAT  ATC  AGC  ACA  AGC  ATA  AGA                    528
Lys  Gly  Glu  Ile  Lys  Asn  Cys  Ser  Phe  Asn  Ile  Ser  Thr  Ser  Ile  Arg
               165                      170                      175

GGT  AAG  GTG  CAG  AAA  GAA  TAT  GCA  TTT  TTT  TAT  AAA  CTT  GAT  ATA  ATA                    576
Gly  Lys  Val  Gln  Lys  Glu  Tyr  Ala  Phe  Phe  Tyr  Lys  Leu  Asp  Ile  Ile
                    180                      185                      190

CCA  ATA  GAT  AAT  GAT  ACT  ACC  AGC  TAT  ACG  TTG  ACA  AGT  TGT  AAC  ACC                    624
Pro  Ile  Asp  Asn  Asp  Thr  Thr  Ser  Tyr  Thr  Leu  Thr  Ser  Cys  Asn  Thr
               195                      200                      205

TCA  GTC  ATT  ACA  CAG  GCC  TGT  CCA  AAG  GTA  TCC  TTT  GAG  CCA  ATT  CCC                    672
Ser  Val  Ile  Thr  Gln  Ala  Cys  Pro  Lys  Val  Ser  Phe  Glu  Pro  Ile  Pro
          210                      215                      220

ATA  CAT  TAT  TGT  GCC  CCG  GCT  GGT  TTT  GCG  ATT  CTA  AAA  TGT  AAT  AAT                    720
Ile  His  Tyr  Cys  Ala  Pro  Ala  Gly  Phe  Ala  Ile  Leu  Lys  Cys  Asn  Asn
225                      230                      235                      240

AAG  ACG  TTC  AAT  GGA  ACA  GGA  CCA  TGT  ACA  AAT  GTC  AGC  ACA  GTA  CAA                    768
Lys  Thr  Phe  Asn  Gly  Thr  Gly  Pro  Cys  Thr  Asn  Val  Ser  Thr  Val  Gln
               245                      250                      255

TGT  ACA  CAT  GGA  ATT  AGG  CCA  GTA  GTA  TCA  ACT  CAA  CTG  CTG  TTG  AAT                    816
Cys  Thr  His  Gly  Ile  Arg  Pro  Val  Val  Ser  Thr  Gln  Leu  Leu  Leu  Asn
                    260                      265                      270

GGC  AGT  CTA  GCA  GAA  GAA  GAG  GTA  GTA  ATT  AGA  TCT  GCC  AAT  TTC  ACA                    864
Gly  Ser  Leu  Ala  Glu  Glu  Glu  Val  Val  Ile  Arg  Ser  Ala  Asn  Phe  Thr
               275                      280                      285

GAC  AAT  GCT  AAA  ACC  ATA  ATA  GTA  CAG  CTG  AAC  CAA  TCT  GTA  GAA  ATT                    912
Asp  Asn  Ala  Lys  Thr  Ile  Ile  Val  Gln  Leu  Asn  Gln  Ser  Val  Glu  Ile
290                      295                      300

AAT  TGT  ACA  GGT  GCT  GGA  CAT  TGT  AAC  ATT  AGT  AGA  GCA  AAA  TGG  AAT                    960
Asn  Cys  Thr  Gly  Ala  Gly  His  Cys  Asn  Ile  Ser  Arg  Ala  Lys  Trp  Asn
305                      310                      315                      320

GCC  ACT  TTA  AAA  CAG  ATA  GCT  AGC  AAA  TTA  AGA  GAA  CAA  TTT  GGA  AAT                   1008
Ala  Thr  Leu  Lys  Gln  Ile  Ala  Ser  Lys  Leu  Arg  Glu  Gln  Phe  Gly  Asn
                    325                      330                      335

AAT  AAA  ACA  ATA  ATC  TTT  AAG  CAA  TCC  TCA  GGA  GGG  GAC  CCA  GAA  ATT                   1056
Asn  Lys  Thr  Ile  Ile  Phe  Lys  Gln  Ser  Ser  Gly  Gly  Asp  Pro  Glu  Ile
               340                      345                      350

GTA  ACG  CAC  AGT  TTT  AAT  TGT  GGA  GGG  GAA  TTT  TTC  TAC  TGT  AAT  TCA                   1104
Val  Thr  His  Ser  Phe  Asn  Cys  Gly  Gly  Glu  Phe  Phe  Tyr  Cys  Asn  Ser
          355                      360                      365

ACA  CAA  CTG  TTT  AAT  AGT  ACT  TGG  TTT  AAT  AGT  ACT  TGG  AGT  ACT  GAA                   1152
Thr  Gln  Leu  Phe  Asn  Ser  Thr  Trp  Phe  Asn  Ser  Thr  Trp  Ser  Thr  Glu
     370                      375                      380

GGG  TCA  AAT  AAC  ACT  GAA  GGA  AGT  GAC  ACA  ATC  ACA  CTC  CCA  TGC  AGA                   1200
Gly  Ser  Asn  Asn  Thr  Glu  Gly  Ser  Asp  Thr  Ile  Thr  Leu  Pro  Cys  Arg
385                      390                      395                      400

ATA  AAA  CAA  TTT  ATA  AAC  ATG  GTG  CAG  GAA  GTA  GGA  AAA  GCA  ATG  TAT                   1248
Ile  Lys  Gln  Phe  Ile  Asn  Met  Val  Gln  Glu  Val  Gly  Lys  Ala  Met  Tyr
               405                      410                      415

GCC  CCT  CCC  ATC  AGC  GGA  CAA  ATT  AGA  TGT  TCA  TCA  AAT  ATT  ACA  GGG                   1296
```

| | | | | | | | | | | | | | | | | |
|---|---|---|---|---|---|---|---|---|---|---|---|---|---|---|---|---|
| Ala | Pro | Pro | Ile | Ser | Gly | Gln | Ile | Arg | Cys | Ser | Ser | Asn | Ile | Thr | Gly | |
| | | 420 | | | | | 425 | | | | | 430 | | | | |
| CTG | CTA | TTA | ACA | AGA | GAT | GGT | GGT | AAT | AAC | AAC | AAT | GGG | TCC | GAG | ATC | 1344 |
| Leu | Leu | Leu | Thr | Arg | Asp | Gly | Gly | Asn | Asn | Asn | Asn | Gly | Ser | Glu | Ile | |
| | | 435 | | | | | 440 | | | | | 445 | | | | |
| TTC | AGA | CCT | GGA | GGA | GGA | GAT | ATG | AGG | GAC | AAT | TGG | AGA | AGT | GAA | TTA | 1392 |
| Phe | Arg | Pro | Gly | Gly | Gly | Asp | Met | Arg | Asp | Asn | Trp | Arg | Ser | Glu | Leu | |
| | | 450 | | | | | 455 | | | | | 460 | | | | |
| TAT | AAA | TAT | AAA | GTA | GTA | AAA | ATT | GAA | CCA | TTA | GGA | GTA | GCA | CCC | ACC | 1440 |
| Tyr | Lys | Tyr | Lys | Val | Val | Lys | Ile | Glu | Pro | Leu | Gly | Val | Ala | Pro | Thr | |
| 465 | | | | 470 | | | | | 475 | | | | | 480 | | |
| AAG | GCA | AAG | AGA | AG | AGTGGTGCAG | AGAGAAAAAT | GAGCGGCCGC | | | | | | | | | 1484 |
| Lys | Ala | Lys | Arg | | | | | | | | | | | | | |

( 2 ) INFORMATION FOR SEQ ID NO:22:

( i ) SEQUENCE CHARACTERISTICS:
        ( A ) LENGTH: 484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

| | | | | | | | | | | | | | | |
|---|---|---|---|---|---|---|---|---|---|---|---|---|---|---|
| Met | Asp | Ala | Met | Lys | Arg | Gly | Leu | Cys | Cys | Val | Leu | Leu | Leu | Cys | Gly |
| 1 | | | | 5 | | | | | 10 | | | | | 15 | |
| Ala | Val | Phe | Val | Ser | Pro | Ser | Gln | Glu | Ile | His | Ala | Arg | Phe | Arg | Arg |
| | | | 20 | | | | | 25 | | | | | 30 | | |
| Gly | Ala | Arg | Thr | Glu | Lys | Leu | Trp | Val | Thr | Val | Tyr | Tyr | Gly | Val | Pro |
| | | | 35 | | | | | 40 | | | | | 45 | | |
| Val | Trp | Lys | Glu | Ala | Thr | Thr | Thr | Leu | Phe | Cys | Ala | Ser | Asp | Ala | Lys |
| | 50 | | | | | 55 | | | | | 60 | | | | |
| Ala | Tyr | Asp | Thr | Glu | Val | His | Asn | Val | Trp | Ala | Thr | His | Ala | Cys | Val |
| 65 | | | | | 70 | | | | | 75 | | | | | 80 |
| Pro | Thr | Asp | Pro | Asn | Pro | Gln | Glu | Val | Val | Leu | Val | Asn | Val | Thr | Glu |
| | | | | 85 | | | | | 90 | | | | | 95 | |
| Asn | Phe | Asn | Met | Trp | Lys | Asn | Asp | Met | Val | Glu | Gln | Met | His | Glu | Asp |
| | | | 100 | | | | | 105 | | | | | 110 | | |
| Ile | Ile | Ser | Leu | Trp | Asp | Gln | Ser | Leu | Lys | Pro | Cys | Val | Lys | Leu | Thr |
| | | | 115 | | | | | 120 | | | | | 125 | | |
| Pro | Leu | Cys | Val | Ser | Leu | Lys | Cys | Thr | Asp | Leu | Gly | Asn | Ala | Thr | Asn |
| | 130 | | | | | 135 | | | | | 140 | | | | |
| Thr | Asn | Ser | Ser | Asn | Thr | Asn | Ser | Ser | Ser | Gly | Glu | Met | Met | Met | Glu |
| 145 | | | | | 150 | | | | | 155 | | | | | 160 |
| Lys | Gly | Glu | Ile | Lys | Asn | Cys | Ser | Phe | Asn | Ile | Ser | Thr | Ser | Ile | Arg |
| | | | | 165 | | | | | 170 | | | | | 175 | |
| Gly | Lys | Val | Gln | Lys | Glu | Tyr | Ala | Phe | Phe | Tyr | Lys | Leu | Asp | Ile | Ile |
| | | | 180 | | | | | 185 | | | | | 190 | | |
| Pro | Ile | Asp | Asn | Asp | Thr | Thr | Ser | Tyr | Thr | Leu | Thr | Ser | Cys | Asn | Thr |
| | | | 195 | | | | | 200 | | | | | 205 | | |
| Ser | Val | Ile | Thr | Gln | Ala | Cys | Pro | Lys | Val | Ser | Phe | Glu | Pro | Ile | Pro |
| | 210 | | | | | 215 | | | | | 220 | | | | |
| Ile | His | Tyr | Cys | Ala | Pro | Ala | Gly | Phe | Ala | Ile | Leu | Lys | Cys | Asn | Asn |
| 225 | | | | | 230 | | | | | 235 | | | | | 240 |
| Lys | Thr | Phe | Asn | Gly | Thr | Gly | Pro | Cys | Thr | Asn | Val | Ser | Thr | Val | Gln |
| | | | | 245 | | | | | 250 | | | | | 255 | |
| Cys | Thr | His | Gly | Ile | Arg | Pro | Val | Val | Ser | Thr | Gln | Leu | Leu | Leu | Asn |
| | | | 260 | | | | | 265 | | | | | 270 | | |

```
Gly Ser Leu Ala Glu Glu Glu Val Val Ile Arg Ser Ala Asn Phe Thr
        275                 280                 285

Asp Asn Ala Lys Thr Ile Ile Val Gln Leu Asn Gln Ser Val Glu Ile
    290                 295                 300

Asn Cys Thr Gly Ala Gly His Cys Asn Ile Ser Arg Ala Lys Trp Asn
305                 310                 315                 320

Ala Thr Leu Lys Gln Ile Ala Ser Lys Leu Arg Glu Gln Phe Gly Asn
                325                 330                 335

Asn Lys Thr Ile Ile Phe Lys Gln Ser Ser Gly Gly Asp Pro Glu Ile
            340                 345                 350

Val Thr His Ser Phe Asn Cys Gly Gly Glu Phe Phe Tyr Cys Asn Ser
        355                 360                 365

Thr Gln Leu Phe Asn Ser Thr Trp Phe Asn Ser Thr Trp Ser Thr Glu
    370                 375                 380

Gly Ser Asn Asn Thr Glu Gly Ser Asp Thr Ile Thr Leu Pro Cys Arg
385                 390                 395                 400

Ile Lys Gln Phe Ile Asn Met Val Gln Glu Val Gly Lys Ala Met Tyr
                405                 410                 415

Ala Pro Pro Ile Ser Gly Gln Ile Arg Cys Ser Ser Asn Ile Thr Gly
            420                 425                 430

Leu Leu Leu Thr Arg Asp Gly Gly Asn Asn Asn Asn Gly Ser Glu Ile
        435                 440                 445

Phe Arg Pro Gly Gly Gly Asp Met Arg Asp Asn Trp Arg Ser Glu Leu
    450                 455                 460

Tyr Lys Tyr Lys Val Val Lys Ile Glu Pro Leu Gly Val Ala Pro Thr
465                 470                 475                 480

Lys Ala Lys Arg
```

( 2 ) INFORMATION FOR SEQ ID NO:23:

( i ) SEQUENCE CHARACTERISTICS:
        ( A ) LENGTH: 1448 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1438
        ( D ) OTHER INFORMATION:

( x i ) SEQUENCE DESCRIPTION: SEQ ID NO:23:

```
ATG GAT GCA ATG AAG AGA GGG CTC TGC TGT GTG CTG CTG CTG TGT GGA      48
Met Asp Ala Met Lys Arg Gly Leu Cys Cys Val Leu Leu Leu Cys Gly
1               5                   10                  15

GCA GTC TTC GTT TCG CCC AGC CAG GAA ATC CAT GCC CGA TTC AGA AGA      96
Ala Val Phe Val Ser Pro Ser Gln Glu Ile His Ala Arg Phe Arg Arg
            20                  25                  30

GGC GGC AGA GTA GAA AAG TTG TGG GTC ACA GTC TAT TAT GGG GTA CCT     144
Gly Gly Arg Val Glu Lys Leu Trp Val Thr Val Tyr Tyr Gly Val Pro
        35                  40                  45

GTG TGG AAA GAA GCA ACC ACC ACT CTA TTT TGT GCA TCA GAT GCT AAA     192
Val Trp Lys Glu Ala Thr Thr Thr Leu Phe Cys Ala Ser Asp Ala Lys
    50                  55                  60

GCA TAT GAT ACA GAG GTA CAT AAT GTT TGG GCC ACA CAT GCC TGT GTA     240
Ala Tyr Asp Thr Glu Val His Asn Val Trp Ala Thr His Ala Cys Val
65                  70                  75                  80
```

| | | | | | | | | | | | | | | | | |
|---|---|---|---|---|---|---|---|---|---|---|---|---|---|---|---|---|
| CCC | ACA | GAC | CCC | AAC | CCA | CAA | GAA | GTA | GTA | TTG | GAA | AAT | GTA | ACA | GAA | 288 |
| Pro | Thr | Asp | Pro | Asn 85 | Pro | Gln | Glu | Val | Val 90 | Leu | Glu | Asn | Val | Thr 95 | Glu | |
| CAT | TTT | AAC | ATG | TGG | AAA | AAT | AAC | ATG | GTA | GAA | CAG | ATG | CAG | GAG | GAT | 336 |
| His | Phe | Asn | Met 100 | Trp | Lys | Asn | Asn | Met 105 | Val | Glu | Gln | Met | Gln 110 | Glu | Asp | |
| ATA | ATC | AGT | TTA | TGG | GAT | CAA | AGC | CTA | AAG | CCA | TGT | GTA | AAA | TTA | ACC | 384 |
| Ile | Ile | Ser 115 | Leu | Trp | Asp | Gln | Ser 120 | Leu | Lys | Pro | Cys | Val 125 | Lys | Leu | Thr | |
| CCA | CTC | TGT | GTT | ACT | TTA | AAT | TGC | AAG | GAT | GTG | AAT | GCT | ACT | AAT | ACC | 432 |
| Pro | Leu 130 | Cys | Val | Thr | Leu | Asn 135 | Cys | Lys | Asp | Val | Asn 140 | Ala | Thr | Asn | Thr | |
| ACT | AAT | GAT | AGC | GAG | GGA | ACG | ATG | GAG | AGA | GGA | GAA | ATA | AAA | AAC | TGC | 480 |
| Thr 145 | Asn | Asp | Ser | Glu | Gly 150 | Thr | Met | Glu | Arg | Gly 155 | Glu | Ile | Lys | Asn | Cys 160 | |
| TCT | TTC | AAT | ATC | ACC | ACA | AGC | ATA | AGA | GAT | GAG | GTG | CAG | AAA | GAA | TAT | 528 |
| Ser | Phe | Asn | Ile | Thr 165 | Thr | Ser | Ile | Arg | Asp 170 | Glu | Val | Gln | Lys | Glu 175 | Tyr | |
| GCT | CTT | TTT | TAT | AAA | CTT | GAT | GTA | GTA | CCA | ATA | GAT | AAT | AAT | AAT | ACC | 576 |
| Ala | Leu | Phe | Tyr 180 | Lys | Leu | Asp | Val | Val 185 | Pro | Ile | Asp | Asn | Asn 190 | Asn | Thr | |
| AGC | TAT | AGG | TTG | ATA | AGT | TGT | GAC | ACC | TCA | GTC | ATT | ACA | CAG | GCC | TGT | 624 |
| Ser | Tyr | Arg 195 | Leu | Ile | Ser | Cys | Asp 200 | Thr | Ser | Val | Ile | Thr 205 | Gln | Ala | Cys | |
| CCA | AAG | ATA | TCC | TTT | GAG | CCA | ATT | CCC | ATA | CAT | TAT | TGT | GCC | CCG | GCT | 672 |
| Pro | Lys 210 | Ile | Ser | Phe | Glu | Pro 215 | Ile | Pro | Ile | His | Tyr 220 | Cys | Ala | Pro | Ala | |
| GGT | TTT | GCG | ATT | CTA | AAG | TGT | AAT | GAT | AAG | ACG | TTC | AAT | GGA | AAA | GGA | 720 |
| Gly 225 | Phe | Ala | Ile | Leu | Lys 230 | Cys | Asn | Asp | Lys | Thr 235 | Phe | Asn | Gly | Lys | Gly 240 | |
| CCA | TGT | AAA | AAT | GTC | AGC | ACA | GTA | CAA | TGT | ACA | CAT | GGA | ATT | AGG | CCA | 768 |
| Pro | Cys | Lys | Asn | Val 245 | Ser | Thr | Val | Gln | Cys 250 | Thr | His | Gly | Ile | Arg 255 | Pro | |
| GTA | GTA | TCA | ACT | CAA | CTG | CTG | CTA | AAT | GGC | AGT | CTA | GCA | GAA | GAA | GAG | 816 |
| Val | Val | Ser | Thr 260 | Gln | Leu | Leu | Leu | Asn 265 | Gly | Ser | Leu | Ala | Glu 270 | Glu | Glu | |
| GTA | GTA | ATT | AGA | TCT | GAC | AAT | TTC | ACG | AAC | AAT | GCT | AAA | ACC | ATA | ATA | 864 |
| Val | Val | Ile 275 | Arg | Ser | Asp | Asn | Phe 280 | Thr | Asn | Asn | Ala | Lys 285 | Thr | Ile | Ile | |
| GTA | CAG | CTG | AAA | GAA | TCT | GTA | GAA | ATT | AAT | TGT | ACA | GGT | GCT | GGA | CAT | 912 |
| Val | Gln | Leu 290 | Lys | Glu | Ser | Val | Glu 295 | Ile | Asn | Cys | Thr | Gly 300 | Ala | Gly | His | |
| TGT | AAC | ATT | AGT | AGA | GCA | AAA | TGG | AAT | GAC | ACT | TTA | AAA | CAG | ATA | GTT | 960 |
| Cys 305 | Asn | Ile | Ser | Arg | Ala 310 | Lys | Trp | Asn | Asp | Thr 315 | Leu | Lys | Gln | Ile | Val 320 | |
| ATA | AAA | TTA | AGA | GAA | CAA | TTT | GAG | AAT | AAA | ACA | ATA | GTC | TTT | AAT | CAC | 1008 |
| Ile | Lys | Leu | Arg | Glu 325 | Gln | Phe | Glu | Asn | Lys 330 | Thr | Ile | Val | Phe | Asn 335 | His | |
| TCC | TCA | GGA | GGG | GAC | CCA | GAA | ATT | GTA | ATG | CAC | AGT | TTT | AAT | TGT | GGA | 1056 |
| Ser | Ser | Gly | Gly 340 | Asp | Pro | Glu | Ile | Val 345 | Met | His | Ser | Phe | Asn 350 | Cys | Gly | |
| GGA | GAA | TTT | TTC | TAC | TGT | AAT | TCA | ACA | CAA | CTG | TTT | AAT | AGT | ACT | TGG | 1104 |
| Gly | Glu | Phe 355 | Phe | Tyr | Cys | Asn | Ser 360 | Thr | Gln | Leu | Phe | Asn 365 | Ser | Thr | Trp | |
| AAT | AAT | AAT | ACT | GAA | GGG | TCA | AAT | AAC | ACT | GAA | GGA | AAT | ACT | ATC | ACA | 1152 |
| Asn | Asn | Asn 370 | Thr | Glu | Gly | Ser 375 | Asn | Asn | Thr | Glu | Gly 380 | Asn | Thr | Ile | Thr | |
| CTC | CCA | TGC | AGA | ATA | AAA | CAA | ATT | ATA | AAC | ATG | GTG | CAG | GAA | GTA | GGA | 1200 |
| Leu 385 | Pro | Cys | Arg | Ile | Lys 390 | Gln | Ile | Ile | Asn | Met 395 | Val | Gln | Glu | Val | Gly 400 | |

| | | | | | | | | | | | | | | | | |
|---|---|---|---|---|---|---|---|---|---|---|---|---|---|---|---|---|
| AAA | GCA | ATG | TAT | GCC | CCT | CCC | ATC | AGA | GGA | CAA | ATT | AGA | TGT | TCA | TCA | 1248 |
| Lys | Ala | Met | Tyr | Ala | Pro | Pro | Ile | Arg | Gly | Gln | Ile | Arg | Cys | Ser | Ser | |
| | | | | 405 | | | | 410 | | | | | | 415 | | |
| AAT | ATT | ACA | GGG | CTG | CTA | TTA | ACA | AGA | GAT | GGT | GGT | ATT | AAT | GAG | AAT | 1296 |
| Asn | Ile | Thr | Gly | Leu | Leu | Leu | Thr | Arg | Asp | Gly | Gly | Ile | Asn | Glu | Asn | |
| | | | 420 | | | | | 425 | | | | | 430 | | | |
| GGG | ACC | GAG | ATC | TTC | AGA | CCT | GGA | GGA | GGA | GAT | ATG | AGG | GAC | AAT | TGG | 1344 |
| Gly | Thr | Glu | Ile | Phe | Arg | Pro | Gly | Gly | Gly | Asp | Met | Arg | Asp | Asn | Trp | |
| | | 435 | | | | | 440 | | | | | 445 | | | | |
| AGA | AGT | GAA | TTA | TAT | AAA | TAT | AAA | GTA | GTA | AAA | ATT | GAA | CCA | TTA | GGA | 1392 |
| Arg | Ser | Glu | Leu | Tyr | Lys | Tyr | Lys | Val | Val | Lys | Ile | Glu | Pro | Leu | Gly | |
| | | 450 | | | | 455 | | | | | 460 | | | | | |
| GTA | GCA | CCC | ACC | AAG | GCA | AAG | AGA | AGA | GTG | GTG | CAA | AGA | GAA | AAA | T | 1438 |
| Val | Ala | Pro | Thr | Lys | Ala | Lys | Arg | Arg | Val | Val | Gln | Arg | Glu | Lys | | |
| 465 | | | | | 470 | | | | | 475 | | | | | | |
| GAGCGGCCGC | | | | | | | | | | | | | | | | 1448 |

( 2 ) INFORMATION FOR SEQ ID NO:24:

( i ) SEQUENCE CHARACTERISTICS:
        ( A ) LENGTH: 479 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

| | | | | | | | | | | | | | | | |
|---|---|---|---|---|---|---|---|---|---|---|---|---|---|---|---|
| Met | Asp | Ala | Met | Lys | Arg | Gly | Leu | Cys | Cys | Val | Leu | Leu | Leu | Cys | Gly |
| 1 | | | | 5 | | | | | 10 | | | | | 15 | |
| Ala | Val | Phe | Val | Ser | Pro | Ser | Gln | Glu | Ile | His | Ala | Arg | Phe | Arg | Arg |
| | | | 20 | | | | | 25 | | | | | 30 | | |
| Gly | Gly | Arg | Val | Glu | Lys | Leu | Trp | Val | Thr | Val | Tyr | Tyr | Gly | Val | Pro |
| | | 35 | | | | | 40 | | | | | 45 | | | |
| Val | Trp | Lys | Glu | Ala | Thr | Thr | Thr | Leu | Phe | Cys | Ala | Ser | Asp | Ala | Lys |
| | 50 | | | | | 55 | | | | | 60 | | | | |
| Ala | Tyr | Asp | Thr | Glu | Val | His | Asn | Val | Trp | Ala | Thr | His | Ala | Cys | Val |
| 65 | | | | | 70 | | | | | 75 | | | | | 80 |
| Pro | Thr | Asp | Pro | Asn | Pro | Gln | Glu | Val | Val | Leu | Glu | Asn | Val | Thr | Glu |
| | | | | 85 | | | | | 90 | | | | | 95 | |
| His | Phe | Asn | Met | Trp | Lys | Asn | Asn | Met | Val | Glu | Gln | Met | Gln | Glu | Asp |
| | | | 100 | | | | | 105 | | | | | 110 | | |
| Ile | Ile | Ser | Leu | Trp | Asp | Gln | Ser | Leu | Lys | Pro | Cys | Val | Lys | Leu | Thr |
| | | | 115 | | | | | 120 | | | | | 125 | | |
| Pro | Leu | Cys | Val | Thr | Leu | Asn | Cys | Lys | Asp | Val | Asn | Ala | Thr | Asn | Thr |
| | | 130 | | | | | 135 | | | | | 140 | | | |
| Thr | Asn | Asp | Ser | Glu | Gly | Thr | Met | Glu | Arg | Gly | Glu | Ile | Lys | Asn | Cys |
| 145 | | | | | 150 | | | | | 155 | | | | | 160 |
| Ser | Phe | Asn | Ile | Thr | Thr | Ser | Ile | Arg | Asp | Glu | Val | Gln | Lys | Glu | Tyr |
| | | | | 165 | | | | | 170 | | | | | 175 | |
| Ala | Leu | Phe | Tyr | Lys | Leu | Asp | Val | Val | Pro | Ile | Asp | Asn | Asn | Asn | Thr |
| | | | 180 | | | | | 185 | | | | | 190 | | |
| Ser | Tyr | Arg | Leu | Ile | Ser | Cys | Asp | Thr | Ser | Val | Ile | Thr | Gln | Ala | Cys |
| | | 195 | | | | | 200 | | | | | 205 | | | |
| Pro | Lys | Ile | Ser | Phe | Glu | Pro | Ile | Pro | Ile | His | Tyr | Cys | Ala | Pro | Ala |
| | 210 | | | | | 215 | | | | | 220 | | | | |
| Gly | Phe | Ala | Ile | Leu | Lys | Cys | Asn | Asp | Lys | Thr | Phe | Asn | Gly | Lys | Gly |
| 225 | | | | | 230 | | | | | 235 | | | | | 240 |
| Pro | Cys | Lys | Asn | Val | Ser | Thr | Val | Gln | Cys | Thr | His | Gly | Ile | Arg | Pro |

-continued

```
                 245                          250                          255
Val  Val  Ser  Thr  Gln  Leu  Leu  Leu  Asn  Gly  Ser  Leu  Ala  Glu  Glu
               260                          265                          270

Val  Val  Ile  Arg  Ser  Asp  Asn  Phe  Thr  Asn  Asn  Ala  Lys  Thr  Ile  Ile
               275                          280                          285

Val  Gln  Leu  Lys  Glu  Ser  Val  Glu  Ile  Asn  Cys  Thr  Gly  Ala  Gly  His
     290                          295                          300

Cys  Asn  Ile  Ser  Arg  Ala  Lys  Trp  Asn  Asp  Thr  Leu  Lys  Gln  Ile  Val
305                          310                          315                     320

Ile  Lys  Leu  Arg  Glu  Gln  Phe  Glu  Asn  Lys  Thr  Ile  Val  Phe  Asn  His
                    325                          330                          335

Ser  Ser  Gly  Gly  Asp  Pro  Glu  Ile  Val  Met  His  Ser  Phe  Asn  Cys  Gly
               340                          345                          350

Gly  Glu  Phe  Phe  Tyr  Cys  Asn  Ser  Thr  Gln  Leu  Phe  Asn  Ser  Thr  Trp
               355                          360                          365

Asn  Asn  Asn  Thr  Glu  Gly  Ser  Asn  Asn  Thr  Glu  Gly  Asn  Thr  Ile  Thr
          370                          375                          380

Leu  Pro  Cys  Arg  Ile  Lys  Gln  Ile  Ile  Asn  Met  Val  Gln  Glu  Val  Gly
385                          390                          395                     400

Lys  Ala  Met  Tyr  Ala  Pro  Pro  Ile  Arg  Gly  Gln  Ile  Arg  Cys  Ser  Ser
                    405                          410                          415

Asn  Ile  Thr  Gly  Leu  Leu  Leu  Thr  Arg  Asp  Gly  Gly  Ile  Asn  Glu  Asn
               420                          425                          430

Gly  Thr  Glu  Ile  Phe  Arg  Pro  Gly  Gly  Gly  Asp  Met  Arg  Asp  Asn  Trp
               435                          440                          445

Arg  Ser  Glu  Leu  Tyr  Lys  Tyr  Lys  Val  Val  Lys  Ile  Glu  Pro  Leu  Gly
     450                          455                          460

Val  Ala  Pro  Thr  Lys  Ala  Lys  Arg  Arg  Val  Val  Gln  Arg  Glu  Lys
465                          470                          475
```

( 2 ) INFORMATION FOR SEQ ID NO:25:

( i ) SEQUENCE CHARACTERISTICS:
        ( A ) LENGTH: 1571 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1567
        ( D ) OTHER INFORMATION:

( x i ) SEQUENCE DESCRIPTION: SEQ ID NO:25:

```
ATG  GAT  GCA  ATG  AAG  AGA  GGG  CTC  TGC  TGT  GTG  CTG  CTG  CTG  TGT  GGA      48
Met  Asp  Ala  Met  Lys  Arg  Gly  Leu  Cys  Cys  Val  Leu  Leu  Leu  Cys  Gly
 1                       5                            10                        15

GCA  GTC  TTC  GTT  TCG  CCC  AGC  CAG  GAA  ATC  CAT  GCC  CGA  TTC  AGA  AGA      96
Ala  Val  Phe  Val  Ser  Pro  Ser  Gln  Glu  Ile  His  Ala  Arg  Phe  Arg  Arg
                    20                           25                       30

GGC  GCC  AGA  ACA  GAA  AAA  TTG  TGG  GTC  ACA  GTC  TAT  TAT  GGG  GTA  CCT     144
Gly  Ala  Arg  Thr  Glu  Lys  Leu  Trp  Val  Thr  Val  Tyr  Tyr  Gly  Val  Pro
          35                           40                           45

GTG  TGG  AAG  GAA  GCA  ACC  ACC  ACT  CTA  TTT  TGT  GCA  TCA  GAT  GCT  AAA     192
Val  Trp  Lys  Glu  Ala  Thr  Thr  Thr  Leu  Phe  Cys  Ala  Ser  Asp  Ala  Lys
     50                            55                           60

GCA  TAT  GAT  ACA  GAG  GTA  CAT  AAT  GTT  TGG  GCC  ACA  CAT  GCC  TGT  GTA     240
Ala  Tyr  Asp  Thr  Glu  Val  His  Asn  Val  Trp  Ala  Thr  His  Ala  Cys  Val
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| 65  |     |     |     |     |     | 70  |     |     |     |     | 75  |     |     |     | 80  |      |
| CCC | ACA | GAC | CCC | AAC | CCA | CAA | GAA | GTA | GTA | TTG | GTA | AAT | GTG | ACA | GAA | 288  |
| Pro | Thr | Asp | Pro | Asn | Pro | Gln | Glu | Val | Val | Leu | Val | Asn | Val | Thr | Glu |      |
|     |     |     |     | 85  |     |     |     |     | 90  |     |     |     |     | 95  |     |      |
| AAT | TTT | AAC | ATG | TGG | AAA | AAT | GAC | ATG | GTA | GAA | CAG | ATG | CAT | GAG | GAT | 336  |
| Asn | Phe | Asn | Met | Trp | Lys | Asn | Asp | Met | Val | Glu | Gln | Met | His | Glu | Asp |      |
|     |     |     | 100 |     |     |     |     | 105 |     |     |     |     | 110 |     |     |      |
| ATA | ATC | AGT | TTA | TGG | GAT | CAA | AGC | CTA | AAG | CCA | TGT | GTA | AAA | TTA | ACC | 384  |
| Ile | Ile | Ser | Leu | Trp | Asp | Gln | Ser | Leu | Lys | Pro | Cys | Val | Lys | Leu | Thr |      |
|     |     | 115 |     |     |     |     | 120 |     |     |     |     | 125 |     |     |     |      |
| CCA | CTC | TGT | GTT | AGT | TTA | AAG | TGC | ACT | GAT | TTG | GGG | AAT | GCT | ACT | AAT | 432  |
| Pro | Leu | Cys | Val | Ser | Leu | Lys | Cys | Thr | Asp | Leu | Gly | Asn | Ala | Thr | Asn |      |
|     | 130 |     |     |     |     | 135 |     |     |     |     | 140 |     |     |     |     |      |
| ACC | AAT | AGT | AGT | AAT | ACC | AAT | AGT | AGT | AGC | GGG | GAA | ATG | ATG | ATG | GAG | 480  |
| Thr | Asn | Ser | Ser | Asn | Thr | Asn | Ser | Ser | Ser | Gly | Glu | Met | Met | Met | Glu |      |
| 145 |     |     |     |     | 150 |     |     |     |     | 155 |     |     |     |     | 160 |      |
| AAA | GGA | GAG | ATA | AAA | AAC | TGC | TCT | TTC | AAT | ATC | AGC | ACA | AGC | ATA | AGA | 528  |
| Lys | Gly | Glu | Ile | Lys | Asn | Cys | Ser | Phe | Asn | Ile | Ser | Thr | Ser | Ile | Arg |      |
|     |     |     |     | 165 |     |     |     |     | 170 |     |     |     |     | 175 |     |      |
| GGT | AAG | GTG | CAG | AAA | GAA | TAT | GCA | TTT | TTT | TAT | AAA | CTT | GAT | ATA | ATA | 576  |
| Gly | Lys | Val | Gln | Lys | Glu | Tyr | Ala | Phe | Phe | Tyr | Lys | Leu | Asp | Ile | Ile |      |
|     |     |     | 180 |     |     |     |     | 185 |     |     |     |     | 190 |     |     |      |
| CCA | ATA | GAT | AAT | GAT | ACT | ACC | AGC | TAT | ACG | TTG | ACA | AGT | TGT | AAC | ACC | 624  |
| Pro | Ile | Asp | Asn | Asp | Thr | Thr | Ser | Tyr | Thr | Leu | Thr | Ser | Cys | Asn | Thr |      |
|     |     | 195 |     |     |     |     | 200 |     |     |     |     | 205 |     |     |     |      |
| TCA | GTC | ATT | ACA | CAG | GCC | TGT | CCA | AAG | GTA | TCC | TTT | GAG | CCA | ATT | CCC | 672  |
| Ser | Val | Ile | Thr | Gln | Ala | Cys | Pro | Lys | Val | Ser | Phe | Glu | Pro | Ile | Pro |      |
|     | 210 |     |     |     |     | 215 |     |     |     |     | 220 |     |     |     |     |      |
| ATA | CAT | TAT | TGT | GCC | CCG | GCT | GGT | TTT | GCG | ATT | CTA | AAA | TGT | AAT | AAT | 720  |
| Ile | His | Tyr | Cys | Ala | Pro | Ala | Gly | Phe | Ala | Ile | Leu | Lys | Cys | Asn | Asn |      |
| 225 |     |     |     |     | 230 |     |     |     |     | 235 |     |     |     |     | 240 |      |
| AAG | ACG | TTC | AAT | GGA | ACA | GGA | CCA | TGT | ACA | AAT | GTC | AGC | ACA | GTA | CAA | 768  |
| Lys | Thr | Phe | Asn | Gly | Thr | Gly | Pro | Cys | Thr | Asn | Val | Ser | Thr | Val | Gln |      |
|     |     |     |     | 245 |     |     |     |     | 250 |     |     |     |     | 255 |     |      |
| TGT | ACA | CAT | GGA | ATT | AGG | CCA | GTA | GTA | TCA | ACT | CAA | CTG | CTG | TTG | AAT | 816  |
| Cys | Thr | His | Gly | Ile | Arg | Pro | Val | Val | Ser | Thr | Gln | Leu | Leu | Leu | Asn |      |
|     |     |     | 260 |     |     |     |     | 265 |     |     |     |     | 270 |     |     |      |
| GGC | AGT | CTA | GCA | GAA | GAA | GAG | GTA | GTA | ATT | AGA | TCT | GCC | AAT | TTC | ACA | 864  |
| Gly | Ser | Leu | Ala | Glu | Glu | Glu | Val | Val | Ile | Arg | Ser | Ala | Asn | Phe | Thr |      |
|     |     | 275 |     |     |     |     | 280 |     |     |     |     | 285 |     |     |     |      |
| GAC | AAT | GCT | AAA | ACC | ATA | ATA | GTA | CAG | CTG | AAC | CAA | TCT | GTA | GAA | ATT | 912  |
| Asp | Asn | Ala | Lys | Thr | Ile | Ile | Val | Gln | Leu | Asn | Gln | Ser | Val | Glu | Ile |      |
|     | 290 |     |     |     |     | 295 |     |     |     |     | 300 |     |     |     |     |      |
| AAT | TGT | ACA | AGA | CCC | AAC | AAC | AAT | ACA | AGA | AAA | AGT | ATC | CGT | ATC | CAG | 960  |
| Asn | Cys | Thr | Arg | Pro | Asn | Asn | Asn | Thr | Arg | Lys | Ser | Ile | Arg | Ile | Gln |      |
| 305 |     |     |     |     | 310 |     |     |     |     | 315 |     |     |     |     | 320 |      |
| AGG | GGA | CCA | GGG | AGA | GCA | TTT | GTT | ACA | ATA | GGA | AAA | ATA | GGA | AAT | ATG | 1008 |
| Arg | Gly | Pro | Gly | Arg | Ala | Phe | Val | Thr | Ile | Gly | Lys | Ile | Gly | Asn | Met |      |
|     |     |     |     | 325 |     |     |     |     | 330 |     |     |     |     | 335 |     |      |
| AGA | CAA | GCA | CAT | TGT | AAC | ATT | AGT | AGA | GCA | AAA | TGG | AAT | GCC | ACT | TTA | 1056 |
| Arg | Gln | Ala | His | Cys | Asn | Ile | Ser | Arg | Ala | Lys | Trp | Asn | Ala | Thr | Leu |      |
|     |     |     | 340 |     |     |     |     | 345 |     |     |     |     | 350 |     |     |      |
| AAA | CAG | ATA | GCT | AGC | AAA | TTA | AGA | GAA | CAA | TTT | GGA | AAT | AAT | AAA | ACA | 1104 |
| Lys | Gln | Ile | Ala | Ser | Lys | Leu | Arg | Glu | Gln | Phe | Gly | Asn | Asn | Lys | Thr |      |
|     |     | 355 |     |     |     |     | 360 |     |     |     |     | 365 |     |     |     |      |
| ATA | ATC | TTT | AAG | CAA | TCC | TCA | GGA | GGG | GAC | CCA | GAA | ATT | GTA | ACG | CAC | 1152 |
| Ile | Ile | Phe | Lys | Gln | Ser | Ser | Gly | Gly | Asp | Pro | Glu | Ile | Val | Thr | His |      |
|     | 370 |     |     |     |     | 375 |     |     |     |     | 380 |     |     |     |     |      |
| AGT | TTT | AAT | TGT | GGA | GGG | GAA | TTT | TTC | TAC | TGT | AAT | TCA | ACA | CAA | CTG | 1200 |
| Ser | Phe | Asn | Cys | Gly | Gly | Glu | Phe | Phe | Tyr | Cys | Asn | Ser | Thr | Gln | Leu |      |

| | | | | | | | | | | | | | | | | |
|---|---|---|---|---|---|---|---|---|---|---|---|---|---|---|---|---|
| 385 | | | | | 390 | | | | | 395 | | | | | 400 | |
| TTT | AAT | AGT | ACT | TGG | TTT | AAT | AGT | ACT | TGG | AGT | ACT | GAA | GGG | TCA | AAT | 1248 |
| Phe | Asn | Ser | Thr | Trp 405 | Phe | Asn | Ser | Thr | Trp 410 | Ser | Thr | Glu | Gly | Ser 415 | Asn | |
| AAC | ACT | GAA | GGA | AGT | GAC | ACA | ATC | ACA | CTC | CCA | TGC | AGA | ATA | AAA | CAA | 1296 |
| Asn | Thr | Glu | Gly 420 | Ser | Asp | Thr | Ile | Thr 425 | Leu | Pro | Cys | Arg | Ile 430 | Lys | Gln | |
| TTT | ATA | AAC | ATG | GTG | CAG | GAA | GTA | GGA | AAA | GCA | ATG | TAT | GCC | CCT | CCC | 1344 |
| Phe | Ile | Asn 435 | Met | Val | Gln | Glu | Val 440 | Gly | Lys | Ala | Met | Tyr 445 | Ala | Pro | Pro | |
| ATC | AGC | GGA | CAA | ATT | AGA | TGT | TCA | TCA | AAT | ATT | ACA | GGG | CTG | CTA | TTA | 1392 |
| Ile | Ser 450 | Gly | Gln | Ile | Arg | Cys 455 | Ser | Ser | Asn | Ile | Thr 460 | Gly | Leu | Leu | Leu | |
| ACA | AGA | GAT | GGT | GGT | AAT | AAC | AAC | AAT | GGG | TCC | GAG | ATC | TTC | AGA | CCT | 1440 |
| Thr 465 | Arg | Asp | Gly | Gly | Asn 470 | Asn | Asn | Asn | Gly | Ser 475 | Glu | Ile | Phe | Arg | Pro 480 | |
| GGA | GGA | GGA | GAT | ATG | AGG | GAC | AAT | TGG | AGA | AGT | GAA | TTA | TAT | AAA | TAT | 1488 |
| Gly | Gly | Gly | Asp | Met 485 | Arg | Asp | Asn | Trp | Arg 490 | Ser | Glu | Leu | Tyr | Lys 495 | Tyr | |
| AAA | GTA | GTA | AAA | ATT | GAA | CCA | TTA | GGA | GTA | GCA | CCC | ACC | AAG | GCA | AAG | 1536 |
| Lys | Val | Val | Lys 500 | Ile | Glu | Pro | Leu | Gly 505 | Val | Ala | Pro | Thr | Lys 510 | Ala | Lys | |
| AGA | AGA | GTG | GTG | CAG | AGA | GAA | AAA | TGA | GCG | G | CCGC | | | | | 1571 |
| Arg | Arg | Val 515 | Val | Gln | Arg | Glu | Lys 520 | | | | | | | | | |

( 2 ) INFORMATION FOR SEQ ID NO:26:

( i ) SEQUENCE CHARACTERISTICS:
        ( A ) LENGTH: 520 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

| | | | | | | | | | | | | | | |
|---|---|---|---|---|---|---|---|---|---|---|---|---|---|---|
| Met 1 | Asp | Ala | Met | Lys 5 | Arg | Gly | Leu | Cys | Cys 10 | Val | Leu | Leu | Leu | Cys 15 | Gly |
| Ala | Val | Phe | Val 20 | Ser | Pro | Ser | Gln | Glu 25 | Ile | His | Ala | Arg | Phe 30 | Arg | Arg |
| Gly | Ala | Arg 35 | Thr | Glu | Lys | Leu | Trp 40 | Val | Thr | Val | Tyr | Tyr 45 | Gly | Val | Pro |
| Val | Trp 50 | Lys | Glu | Ala | Thr | Thr 55 | Thr | Leu | Phe | Cys | Ala 60 | Ser | Asp | Ala | Lys |
| Ala 65 | Tyr | Asp | Thr | Glu | Val 70 | His | Asn | Val | Trp | Ala 75 | Thr | His | Ala | Cys | Val 80 |
| Pro | Thr | Asp | Pro | Asn 85 | Pro | Gln | Glu | Val | Val 90 | Leu | Val | Asn | Val | Thr 95 | Glu |
| Asn | Phe | Asn | Met 100 | Trp | Lys | Asn | Asp | Met 105 | Val | Glu | Gln | Met | His 110 | Glu | Asp |
| Ile | Ile | Ser 115 | Leu | Trp | Asp | Gln | Ser 120 | Leu | Lys | Pro | Cys | Val 125 | Lys | Leu | Thr |
| Pro | Leu 130 | Cys | Val | Ser | Leu | Lys 135 | Cys | Thr | Asp | Leu | Gly 140 | Asn | Ala | Thr | Asn |
| Thr 145 | Asn | Ser | Ser | Asn | Thr 150 | Asn | Ser | Ser | Ser | Gly 155 | Glu | Met | Met | Met | Glu 160 |
| Lys | Gly | Glu | Ile | Lys 165 | Asn | Cys | Ser | Phe | Asn 170 | Ile | Ser | Thr | Ser | Ile 175 | Arg |
| Gly | Lys | Val | Gln | Lys | Glu | Tyr | Ala | Phe | Phe | Tyr | Lys | Leu | Asp | Ile | Ile |

|     |     |     |     |     | 180 |     |     |     |     | 185 |     |     |     |     | 190 |     |     |
|---|---|---|---|---|---|---|---|---|---|---|---|---|---|---|---|---|---|

Pro Ile Asp Asn Asp Thr Thr Ser Tyr Thr Leu Thr Ser Cys Asn Thr
        195                 200                 205

Ser Val Ile Thr Gln Ala Cys Pro Lys Val Ser Phe Glu Pro Ile Pro
    210             215                 220

Ile His Tyr Cys Ala Pro Ala Gly Phe Ala Ile Leu Lys Cys Asn Asn
225             230                 235                     240

Lys Thr Phe Asn Gly Thr Gly Pro Cys Thr Asn Val Ser Thr Val Gln
            245                 250                 255

Cys Thr His Gly Ile Arg Pro Val Val Ser Thr Gln Leu Leu Leu Asn
        260                 265                 270

Gly Ser Leu Ala Glu Glu Val Val Ile Arg Ser Ala Asn Phe Thr
        275                 280                 285

Asp Asn Ala Lys Thr Ile Ile Val Gln Leu Asn Gln Ser Val Glu Ile
    290                 295                 300

Asn Cys Thr Arg Pro Asn Asn Thr Arg Lys Ser Ile Arg Ile Gln
305                 310                 315                     320

Arg Gly Pro Gly Arg Ala Phe Val Thr Ile Gly Lys Ile Gly Asn Met
                325                 330                 335

Arg Gln Ala His Cys Asn Ile Ser Arg Ala Lys Trp Asn Ala Thr Leu
            340                 345                 350

Lys Gln Ile Ala Ser Lys Leu Arg Glu Gln Phe Gly Asn Asn Lys Thr
        355                 360                 365

Ile Ile Phe Lys Gln Ser Ser Gly Gly Asp Pro Glu Ile Val Thr His
        370                 375                 380

Ser Phe Asn Cys Gly Gly Glu Phe Phe Tyr Cys Asn Ser Thr Gln Leu
385                 390                 395                     400

Phe Asn Ser Thr Trp Phe Asn Ser Thr Trp Ser Thr Glu Gly Ser Asn
                405                 410                 415

Asn Thr Glu Gly Ser Asp Thr Ile Thr Leu Pro Cys Arg Ile Lys Gln
            420                 425                 430

Phe Ile Asn Met Val Gln Glu Val Gly Lys Ala Met Tyr Ala Pro Pro
        435                 440                 445

Ile Ser Gly Gln Ile Arg Cys Ser Ser Asn Ile Thr Gly Leu Leu Leu
450                 455                 460

Thr Arg Asp Gly Gly Asn Asn Asn Asn Gly Ser Glu Ile Phe Arg Pro
465                 470                 475                     480

Gly Gly Gly Asp Met Arg Asp Asn Trp Arg Ser Glu Leu Tyr Lys Tyr
                485                 490                 495

Lys Val Val Lys Ile Glu Pro Leu Gly Val Ala Pro Thr Lys Ala Lys
            500                 505                 510

Arg Arg Val Val Gln Arg Glu Lys
            515                 520

(2) INFORMATION FOR SEQ ID NO:27:

(i) SEQUENCE CHARACTERISTICS:
        (A) LENGTH: 1532 base pairs
        (B) TYPE: nucleic acid
        (C) STRANDEDNESS: single
        (D) TOPOLOGY: linear (ii) MOLECULE TYPE: DNA (genomic)

(ix) FEATURE:
        (A) NAME/KEY: CDS
        (B) LOCATION: 1..1522
        (D) OTHER INFORMATION:

( x i ) SEQUENCE DESCRIPTION: SEQ ID NO:27:

| | | | | | | | | | | | | | | | | |
|---|---|---|---|---|---|---|---|---|---|---|---|---|---|---|---|---|
| ATG | GAT | GCA | ATG | AAG | AGA | GGG | CTC | TGC | TGT | GTG | CTG | CTG | CTG | TGT | GGA | 48 |
| Met | Asp | Ala | Met | Lys | Arg | Gly | Leu | Cys | Cys | Val | Leu | Leu | Leu | Cys | Gly | |
| 1 | | | | 5 | | | | | 10 | | | | | 15 | | |
| GCA | GTC | TTC | GTT | TCG | CCC | AGC | CAG | GAA | ATC | CAT | GCC | CGA | TTC | AGA | AGA | 96 |
| Ala | Val | Phe | Val | Ser | Pro | Ser | Gln | Glu | Ile | His | Ala | Arg | Phe | Arg | Arg | |
| | | | 20 | | | | | 25 | | | | | 30 | | | |
| GGC | GGC | AGA | GTA | GAA | AAG | TTG | TGG | GTC | ACA | GTC | TAT | TAT | GGG | GTA | CCT | 144 |
| Gly | Gly | Arg | Val | Glu | Lys | Leu | Trp | Val | Thr | Val | Tyr | Tyr | Gly | Val | Pro | |
| | | 35 | | | | | 40 | | | | | 45 | | | | |
| GTG | TGG | AAA | GAA | GCA | ACC | ACC | ACT | CTA | TTT | TGT | GCA | TCA | GAT | GCT | AAA | 192 |
| Val | Trp | Lys | Glu | Ala | Thr | Thr | Thr | Leu | Phe | Cys | Ala | Ser | Asp | Ala | Lys | |
| | 50 | | | | | 55 | | | | | 60 | | | | | |
| GCA | TAT | GAT | ACA | GAG | GTA | CAT | AAT | GTT | TGG | GCC | ACA | CAT | GCC | TGT | GTA | 240 |
| Ala | Tyr | Asp | Thr | Glu | Val | His | Asn | Val | Trp | Ala | Thr | His | Ala | Cys | Val | |
| 65 | | | | | 70 | | | | | 75 | | | | | 80 | |
| CCC | ACA | GAC | CCC | AAC | CCA | CAA | GAA | GTA | GTA | TTG | GAA | AAT | GTA | ACA | GAA | 288 |
| Pro | Thr | Asp | Pro | Asn | Pro | Gln | Glu | Val | Val | Leu | Glu | Asn | Val | Thr | Glu | |
| | | | | 85 | | | | | 90 | | | | | 95 | | |
| CAT | TTT | AAC | ATG | TGG | AAA | AAT | AAC | ATG | GTA | GAA | CAG | ATG | CAG | GAG | GAT | 336 |
| His | Phe | Asn | Met | Trp | Lys | Asn | Asn | Met | Val | Glu | Gln | Met | Gln | Glu | Asp | |
| | | | 100 | | | | | 105 | | | | | 110 | | | |
| ATA | ATC | AGT | TTA | TGG | GAT | CAA | AGC | CTA | AAG | CCA | TGT | GTA | AAA | TTA | ACC | 384 |
| Ile | Ile | Ser | Leu | Trp | Asp | Gln | Ser | Leu | Lys | Pro | Cys | Val | Lys | Leu | Thr | |
| | | 115 | | | | | 120 | | | | | 125 | | | | |
| CCA | CTC | TGT | GTT | ACT | TTA | AAT | TGC | AAG | GAT | GTG | AAT | GCT | ACT | AAT | ACC | 432 |
| Pro | Leu | Cys | Val | Thr | Leu | Asn | Cys | Lys | Asp | Val | Asn | Ala | Thr | Asn | Thr | |
| | 130 | | | | | 135 | | | | | 140 | | | | | |
| ACT | AAT | GAT | AGC | GAG | GGA | ACG | ATG | GAG | AGA | GGA | GAA | ATA | AAA | AAC | TGC | 480 |
| Thr | Asn | Asp | Ser | Glu | Gly | Thr | Met | Glu | Arg | Gly | Glu | Ile | Lys | Asn | Cys | |
| 145 | | | | | 150 | | | | | 155 | | | | | 160 | |
| TCT | TTC | AAT | ATC | ACC | ACA | AGC | ATA | AGA | GAT | GAG | GTG | CAG | AAA | GAA | TAT | 528 |
| Ser | Phe | Asn | Ile | Thr | Thr | Ser | Ile | Arg | Asp | Glu | Val | Gln | Lys | Glu | Tyr | |
| | | | | 165 | | | | | 170 | | | | | 175 | | |
| GCT | CTT | TTT | TAT | AAA | CTT | GAT | GTA | GTA | CCA | ATA | GAT | AAT | AAT | AAT | ACC | 576 |
| Ala | Leu | Phe | Tyr | Lys | Leu | Asp | Val | Val | Pro | Ile | Asp | Asn | Asn | Asn | Thr | |
| | | | 180 | | | | | 185 | | | | | 190 | | | |
| AGC | TAT | AGG | TTG | ATA | AGT | TGT | GAC | ACC | TCA | GTC | ATT | ACA | CAG | GCC | TGT | 624 |
| Ser | Tyr | Arg | Leu | Ile | Ser | Cys | Asp | Thr | Ser | Val | Ile | Thr | Gln | Ala | Cys | |
| | | 195 | | | | | 200 | | | | | 205 | | | | |
| CCA | AAG | ATA | TCC | TTT | GAG | CCA | ATT | CCC | ATA | CAT | TAT | TGT | GCC | CCG | GCT | 672 |
| Pro | Lys | Ile | Ser | Phe | Glu | Pro | Ile | Pro | Ile | His | Tyr | Cys | Ala | Pro | Ala | |
| | 210 | | | | | 215 | | | | | 220 | | | | | |
| GGT | TTT | GCG | ATT | CTA | AAG | TGT | AAT | GAT | AAG | ACG | TTC | AAT | GGA | AAA | GGA | 720 |
| Gly | Phe | Ala | Ile | Leu | Lys | Cys | Asn | Asp | Lys | Thr | Phe | Asn | Gly | Lys | Gly | |
| 225 | | | | | 230 | | | | | 235 | | | | | 240 | |
| CCA | TGT | AAA | AAT | GTC | AGC | ACA | GTA | CAA | TGT | ACA | CAT | GGA | ATT | AGG | CCA | 768 |
| Pro | Cys | Lys | Asn | Val | Ser | Thr | Val | Gln | Cys | Thr | His | Gly | Ile | Arg | Pro | |
| | | | | 245 | | | | | 250 | | | | | 255 | | |
| GTA | GTA | TCA | ACT | CAA | CTG | CTG | CTA | AAT | GGC | AGT | CTA | GCA | GAA | GAA | GAG | 816 |
| Val | Val | Ser | Thr | Gln | Leu | Leu | Leu | Asn | Gly | Ser | Leu | Ala | Glu | Glu | Glu | |
| | | | 260 | | | | | 265 | | | | | 270 | | | |
| GTA | GTA | ATT | AGA | TCT | GAC | AAT | TTC | ACG | AAC | AAT | GCT | AAA | ACC | ATA | ATA | 864 |
| Val | Val | Ile | Arg | Ser | Asp | Asn | Phe | Thr | Asn | Asn | Ala | Lys | Thr | Ile | Ile | |
| | | 275 | | | | | 280 | | | | | 285 | | | | |
| GTA | CAG | CTG | AAA | GAA | TCT | GTA | GAA | ATT | AAT | TGT | ACA | AGA | CCC | AAC | AAC | 912 |
| Val | Gln | Leu | Lys | Glu | Ser | Val | Glu | Ile | Asn | Cys | Thr | Arg | Pro | Asn | Asn | |
| | 290 | | | | | 295 | | | | | 300 | | | | | |
| AAT | ACA | AGA | AAA | AGT | ATA | CAT | ATA | GGA | CCA | GGG | AGA | GCA | TTT | TAT | ACT | 960 |

| | | | | | | | | | | | | | | | |
|---|---|---|---|---|---|---|---|---|---|---|---|---|---|---|---|
| Asn | Thr | Arg | Lys | Ser | Ile | His | Ile | Gly | Pro | Gly | Arg | Ala | Phe | Tyr | Thr |
| 305 | | | | | 310 | | | | | 315 | | | | | 320 |

| ACA | GGA | GAA | ATA | ATA | GGA | GAT | ATA | AGA | CAA | GCA | CAT | TGT | AAC | ATT | AGT | 1008 |
|---|---|---|---|---|---|---|---|---|---|---|---|---|---|---|---|---|
| Thr | Gly | Glu | Ile | Ile | Gly | Asp | Ile | Arg | Gln | Ala | His | Cys | Asn | Ile | Ser | |
| | | | | 325 | | | | | 330 | | | | | 335 | | |

| AGA | GCA | AAA | TGG | AAT | GAC | ACT | TTA | AAA | CAG | ATA | GTT | ATA | AAA | TTA | AGA | 1056 |
|---|---|---|---|---|---|---|---|---|---|---|---|---|---|---|---|---|
| Arg | Ala | Lys | Trp | Asn | Asp | Thr | Leu | Lys | Gln | Ile | Val | Ile | Lys | Leu | Arg | |
| | | | 340 | | | | | 345 | | | | | 350 | | | |

| GAA | CAA | TTT | GAG | AAT | AAA | ACA | ATA | GTC | TTT | AAT | CAC | TCC | TCA | GGA | GGG | 1104 |
|---|---|---|---|---|---|---|---|---|---|---|---|---|---|---|---|---|
| Glu | Gln | Phe | Glu | Asn | Lys | Thr | Ile | Val | Phe | Asn | His | Ser | Ser | Gly | Gly | |
| | | 355 | | | | | 360 | | | | | 365 | | | | |

| GAC | CCA | GAA | ATT | GTA | ATG | CAC | AGT | TTT | AAT | TGT | GGA | GGA | GAA | TTT | TTC | 1152 |
|---|---|---|---|---|---|---|---|---|---|---|---|---|---|---|---|---|
| Asp | Pro | Glu | Ile | Val | Met | His | Ser | Phe | Asn | Cys | Gly | Gly | Glu | Phe | Phe | |
| | 370 | | | | | 375 | | | | | 380 | | | | | |

| TAC | TGT | AAT | TCA | ACA | CAA | CTG | TTT | AAT | AGT | ACT | TGG | AAT | AAT | AAT | ACT | 1200 |
|---|---|---|---|---|---|---|---|---|---|---|---|---|---|---|---|---|
| Tyr | Cys | Asn | Ser | Thr | Gln | Leu | Phe | Asn | Ser | Thr | Trp | Asn | Asn | Asn | Thr | |
| 385 | | | | | 390 | | | | | 395 | | | | | 400 | |

| GAA | GGG | TCA | AAT | AAC | ACT | GAA | GGA | AAT | ACT | ATC | ACA | CTC | CCA | TGC | AGA | 1248 |
|---|---|---|---|---|---|---|---|---|---|---|---|---|---|---|---|---|
| Glu | Gly | Ser | Asn | Asn | Thr | Glu | Gly | Asn | Thr | Ile | Thr | Leu | Pro | Cys | Arg | |
| | | | | 405 | | | | | 410 | | | | | 415 | | |

| ATA | AAA | CAA | ATT | ATA | AAC | ATG | GTG | CAG | GAA | GTA | GGA | AAA | GCA | ATG | TAT | 1296 |
|---|---|---|---|---|---|---|---|---|---|---|---|---|---|---|---|---|
| Ile | Lys | Gln | Ile | Ile | Asn | Met | Val | Gln | Glu | Val | Gly | Lys | Ala | Met | Tyr | |
| | | | 420 | | | | | 425 | | | | | 430 | | | |

| GCC | CCT | CCC | ATC | AGA | GGA | CAA | ATT | AGA | TGT | TCA | TCA | AAT | ATT | ACA | GGG | 1344 |
|---|---|---|---|---|---|---|---|---|---|---|---|---|---|---|---|---|
| Ala | Pro | Pro | Ile | Arg | Gly | Gln | Ile | Arg | Cys | Ser | Ser | Asn | Ile | Thr | Gly | |
| | | 435 | | | | | 440 | | | | | 445 | | | | |

| CTG | CTA | TTA | ACA | AGA | GAT | GGT | GGT | ATT | AAT | GAG | AAT | GGG | ACC | GAG | ATC | 1392 |
|---|---|---|---|---|---|---|---|---|---|---|---|---|---|---|---|---|
| Leu | Leu | Leu | Thr | Arg | Asp | Gly | Gly | Ile | Asn | Glu | Asn | Gly | Thr | Glu | Ile | |
| | 450 | | | | | 455 | | | | | 460 | | | | | |

| TTC | AGA | CCT | GGA | GGA | GGA | GAT | ATG | AGG | GAC | AAT | TGG | AGA | AGT | GAA | TTA | 1440 |
|---|---|---|---|---|---|---|---|---|---|---|---|---|---|---|---|---|
| Phe | Arg | Pro | Gly | Gly | Gly | Asp | Met | Arg | Asp | Asn | Trp | Arg | Ser | Glu | Leu | |
| 465 | | | | | 470 | | | | | 475 | | | | | 480 | |

| TAT | AAA | TAT | AAA | GTA | GTA | AAA | ATT | GAA | CCA | TTA | GGA | GTA | GCA | CCC | ACC | 1488 |
|---|---|---|---|---|---|---|---|---|---|---|---|---|---|---|---|---|
| Tyr | Lys | Tyr | Lys | Val | Val | Lys | Ile | Glu | Pro | Leu | Gly | Val | Ala | Pro | Thr | |
| | | | | 485 | | | | | 490 | | | | | 495 | | |

| AAG | GCA | AAG | AGA | AGA | GTG | GTG | CAA | AGA | GAA | AAA | T | GAGCGGCCGC | | | | 1532 |
|---|---|---|---|---|---|---|---|---|---|---|---|---|---|---|---|---|
| Lys | Ala | Lys | Arg | Arg | Val | Val | Gln | Arg | Glu | Lys | | | | | | |
| | | | 500 | | | | | 505 | | | | | | | | |

( 2 ) INFORMATION FOR SEQ ID NO:28:

( i ) SEQUENCE CHARACTERISTICS:
        ( A ) LENGTH: 507 amino acids
        ( B ) TYPE: amino acid
        ( D ) TOPOLOGY: linear ( i i ) MOLECULE TYPE: protein ( x i ) SEQUENCE DESCRIPTION: SEQ ID NO:28:

| Met | Asp | Ala | Met | Lys | Arg | Gly | Leu | Cys | Cys | Val | Leu | Leu | Leu | Cys | Gly |
|---|---|---|---|---|---|---|---|---|---|---|---|---|---|---|---|
| 1 | | | | 5 | | | | | 10 | | | | | 15 | |

| Ala | Val | Phe | Val | Ser | Pro | Ser | Gln | Glu | Ile | His | Ala | Arg | Phe | Arg | Arg |
|---|---|---|---|---|---|---|---|---|---|---|---|---|---|---|---|
| | | | 20 | | | | | 25 | | | | | 30 | | |

| Gly | Gly | Arg | Val | Glu | Lys | Leu | Trp | Val | Thr | Val | Tyr | Tyr | Gly | Val | Pro |
|---|---|---|---|---|---|---|---|---|---|---|---|---|---|---|---|
| | | 35 | | | | | 40 | | | | | 45 | | | |

| Val | Trp | Lys | Glu | Ala | Thr | Thr | Thr | Leu | Phe | Cys | Ala | Ser | Asp | Ala | Lys |
|---|---|---|---|---|---|---|---|---|---|---|---|---|---|---|---|
| | 50 | | | | | 55 | | | | | 60 | | | | |

| Ala | Tyr | Asp | Thr | Glu | Val | His | Asn | Val | Trp | Ala | Thr | His | Ala | Cys | Val |
|---|---|---|---|---|---|---|---|---|---|---|---|---|---|---|---|
| 65 | | | | | 70 | | | | | 75 | | | | | 80 |

| Pro | Thr | Asp | Pro | Asn | Pro | Gln | Glu | Val | Val | Leu | Glu | Asn | Val | Thr | Glu |
|---|---|---|---|---|---|---|---|---|---|---|---|---|---|---|---|
| | | | | 85 | | | | | 90 | | | | | 95 | |

```
His Phe Asn Met Trp Lys Asn Asn Met Val Glu Gln Met Gln Glu Asp
            100                 105                 110

Ile Ile Ser Leu Trp Asp Gln Ser Leu Lys Pro Cys Val Lys Leu Thr
            115                 120                 125

Pro Leu Cys Val Thr Leu Asn Cys Lys Asp Val Asn Ala Thr Asn Thr
            130                 135                 140

Thr Asn Asp Ser Glu Gly Thr Met Glu Arg Gly Glu Ile Lys Asn Cys
145                     150                 155                 160

Ser Phe Asn Ile Thr Thr Ser Ile Arg Asp Glu Val Gln Lys Glu Tyr
                165                 170                 175

Ala Leu Phe Tyr Lys Leu Asp Val Val Pro Ile Asp Asn Asn Asn Thr
            180                 185                 190

Ser Tyr Arg Leu Ile Ser Cys Asp Thr Ser Val Ile Thr Gln Ala Cys
            195                 200                 205

Pro Lys Ile Ser Phe Glu Pro Ile Pro Ile His Tyr Cys Ala Pro Ala
    210                 215                 220

Gly Phe Ala Ile Leu Lys Cys Asn Asp Lys Thr Phe Asn Gly Lys Gly
225                 230                 235                     240

Pro Cys Lys Asn Val Ser Thr Val Gln Cys Thr His Gly Ile Arg Pro
                245                 250                 255

Val Val Ser Thr Gln Leu Leu Leu Asn Gly Ser Leu Ala Glu Glu
                260                 265                 270

Val Val Ile Arg Ser Asp Asn Phe Thr Asn Asn Ala Lys Thr Ile Ile
            275                 280                 285

Val Gln Leu Lys Glu Ser Val Glu Ile Asn Cys Thr Arg Pro Asn Asn
    290                 295                 300

Asn Thr Arg Lys Ser Ile His Ile Gly Pro Gly Arg Ala Phe Tyr Thr
305                 310                 315                 320

Thr Gly Glu Ile Ile Gly Asp Ile Arg Gln Ala His Cys Asn Ile Ser
                325                 330                 335

Arg Ala Lys Trp Asn Asp Thr Leu Lys Gln Ile Val Ile Lys Leu Arg
            340                 345                 350

Glu Gln Phe Glu Asn Lys Thr Ile Val Phe Asn His Ser Ser Gly Gly
            355                 360                 365

Asp Pro Glu Ile Val Met His Ser Phe Asn Cys Gly Gly Glu Phe Phe
    370                 375                 380

Tyr Cys Asn Ser Thr Gln Leu Phe Asn Ser Thr Trp Asn Asn Asn Thr
385                 390                 395                 400

Glu Gly Ser Asn Asn Thr Glu Gly Asn Thr Ile Thr Leu Pro Cys Arg
                405                 410                 415

Ile Lys Gln Ile Ile Asn Met Val Gln Glu Val Gly Lys Ala Met Tyr
            420                 425                 430

Ala Pro Pro Ile Arg Gly Gln Ile Arg Cys Ser Ser Asn Ile Thr Gly
            435                 440                 445

Leu Leu Leu Thr Arg Asp Gly Gly Ile Asn Glu Asn Gly Thr Glu Ile
    450                 455                 460

Phe Arg Pro Gly Gly Gly Asp Met Arg Asp Asn Trp Arg Ser Glu Leu
465                 470                 475                 480

Tyr Lys Tyr Lys Val Val Lys Ile Glu Pro Leu Gly Val Ala Pro Thr
                485                 490                 495

Lys Ala Lys Arg Arg Val Val Gln Arg Glu Lys
            500                 505
```

( 2 ) INFORMATION FOR SEQ ID NO:29:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:29:

```
Ala  Pro  Thr  Lys  Ala  Lys  Arg  Arg  Val  Val  Gln  Arg  Glu  Lys  Arg
1                  5                           10                      15
```

HIV-1 ANTIGENS, ANTIBODY COMPOSITIONS RELATED THERETO, AND THERAPEUTIC AND PROPHYLACTIC USES THEREOF

BACKGROUND OF THE INVENTION

This application is a 371 of PCT/US94/03282, filed Mar. 25, 1994 which is a continuation of application Ser. No. 08/037,816, filed Mar. 26, 1993. Throughout this application, various publications are referenced by Arabic numerals. Full citations for these references may be found at the end of the specification immediately preceding the claims. The disclosure of these publications is hereby incorporated by reference into this application to describe more fully the art to which this invention pertains.

The life cycle of animal viruses is characterized by a series of events that are required for the productive infection of the host cell. The initial step in the replicative cycle is the attachment of the virus to the cell surface, which attachment is mediated by the specific interaction of the viral attachment protein (VAP) to receptors on the surface of the target cell. The differential pattern of expression of these receptors is largely responsible for the host range and tropic properties of viruses. In addition, an effective immune response against many viruses is mediated through neutralizing antibodies directed against the VAP. The interaction of the VAP with cellular receptors and the immune system therefore plays a critical role in infection and pathogenesis of viral disease.

The human immunodeficiency virus type 1 (HIV-1) infects primarily helper T lymphocytes, dendritic cells, and monocytes/macrophages—cells that express surface CD4—leading to a gradual loss of immune function. This loss of function results in the development of the human acquired immunodeficiency syndrome (AIDS) (1). The initial phase of the HIV-1 replicative cycle involves the high-affinity interaction between the HIV-1 exterior envelope glycoprotein gp120 and cell surface CD4 ($K_d$ approximately $4 \times 10^{-9}$ M) (2). Several lines of evidence demonstrate the requirement of this interaction for viral infectivity. The introduction into CD4$^-$ human cells of cDNA encoding CD4 is sufficient to render otherwise resistant cells susceptible to HIV-1 infection (3). In vivo, viral infection appears to be restricted to cells expressing CD4, indicating that the cellular tropism of HIV-1 is largely determined by the pattern of cellular expression of CD4. Following the binding of HIV-1 gp120 to cell surface CD4, viral and target cell membranes fuse by a mechanism that is poorly understood, resulting in the introduction of the viral capsid into the target cell cytoplasm (4).

Mature CD4 has a relative molecular mass (Mr) of 55 kDa and consists of an N-terminal 372-amino acid extracellular domain containing four tandem immunoglobulin-like regions (V1–V4), followed by a 23-amino acid transmembrane domain and a 38-amino acid cytoplasmic segment (5, 6). In experiments using truncated sCD4 proteins, it has been shown that the determinants for high-affinity binding to HIV-1 gp120 lie solely within the N-terminal immunoglobulin-like domain V1) (7–9). Mutational analysis of V1 has defined a discrete binding site (residues 38–52) that comprises a region structurally homologous to the second complementarity-determining region (CDR2) of immunoglobulin genes (9).

The production of large quantities of sCD4 has permitted a structural analysis of the two N-terminal immunoglobulin-like domains (V1V2). The structure determined at 2.3 angstrom resolution reveals that the molecule has two tightly-associated domains, each of which contains the immunoglobulin-fold connected by a continuous beta strand. The putative binding sites for monoclonal antibodies, class II major histocompatibility complex (MHC) molecules, and HIV-1 gp120, as determined by mutational analyses, map on the molecular surface (10, 11).

The HIV-1 envelope gene env encodes an envelope glycoprotein precursor, gp160, which is cleaved by cellular proteases before transport to the plasma membrane to yield gp120 and gp41. The membrane-spanning glycoprotein, gp41, is non-covalently associated with gp120, a purely extracellular glycoprotein. The mature gp120 molecule is heavily glycosylated (approximately 24 N-linked oligosaccharides), contains approximately 480 amino acid residues with 9 intrachain disulfide bonds (12), and projects from the viral membrane as a dimeric or multimeric molecule (13).

Mutational studies of HIV-1 gp120 have delineated important functional regions of the molecule. The regions of gp120 that interact with gp41 map primarily to the N- and C-termini (14). The predominant strain-specific neutralizing epitope on gp120 is located in the 32–34 amino acid residue third variable loop, herein referred to as the V3 loop, which resides near the center of the gp120 sequence (15). The CD4 binding site maps to discontinuous regions of gp120 that include highly conserved or invariant amino acid residues in the second, third, and fourth conserved domains (the C2, C3, and C4 domains) of gp120 (16). It has been postulated that a small pocket formed by these conserved residues within gp120 could accommodate the CDR2 loop of CD4, a region defined by mutational analyses as important in interacting with gp120 (17).

HIV-1 gp120 not only mediates viral attachment to surface CD4 molecules, but also serves as the major target of antibodies which neutralize non-cell-associated virus and inhibit cell to cell viral transmission.

There are two major classifications of HIV-1-neutralizing antibodies: type-specific and group-common (15). Type-specific neutralizing antibodies primarily recognize linear determinants in the highly variable V3 loop of gp120. These antibodies act by inhibiting fusion between HIV-1 and the target cell membrane, and generally neutralize only a particular isolate of, or closely related strains of, HIV-1. Sequence variation within the V3 loop, as well as outside of this region, permits viruses to escape neutralization by anti-V3 loop antibodies. In contrast, group-common neutralizing antibodies primarily recognize discontinuous or conformational epitopes in gp120, and possess the ability to neutralize a diverse range of HIV-1 isolates. These broadly neutralizing antibodies often recognize a site on gp120 which overlaps the highly conserved CD4-binding site, and thus inhibits gp120 -CD4 binding.

A structural relationship has been demonstrated between the V3 loop and the C4 region of gp120 which region constitutes both part of the CD4 binding site and part of the conserved neutralization epitopes. It was observed that deleting the V3 loop resulted in significantly increased binding of a panel of broadly neutralizing hMoAbs (neutralizing human monoclonal antibodies) to the CD4 binding site (18).

A major goal in AIDS vaccine development is to develop a vaccine able to protect a subject against the numerous genetic variants of HIV-1 that infect humans. Although cell-mediated immune responses might serve to control infection in HIV-1-infected individuals, several lines of evidence demonstrate that protection against infection is mainly mediated by neutralizing antibodies directed against gp120. Early experiments showed that immunization of chimpanzees with recombinant gp120 induced a protective immune response against challenge with the homologous HIV-1 strain (17). This protection correlated with the presence of high-titer neutralizing antibodies against the V3 loop of gp120. In addition, passive immunization of chimpanzees with a V3-loop neutralizing monoclonal antibody resulted in protection against challenge with the homologous HIV-1 strain (19). Although protection against challenge was demonstrated in these two experiments, recent studies have questioned the clinical relevance of these findings. For example, these neutralizing antibodies recognize the V3 loop determinants of a single strain, and not conserved or discontinuous epitopes. Thus, these antibodies lack the ability to neutralize the broad spectrum of HIV-1 strains present in an HIV-1 population. Furthermore, the challenge virus was the homologous HIV-1 laboratory adapted LAI (HTLV-IIIB) strain and not one of the primary isolates that contain considerable gp120 sequence heterogeneity. Since these experiments showed that gp120 subunit vaccination induces an immune response effective against only the homogeneous HIV-1 strain used as an antigen, it is unlikely that the vaccination regimens used in these studies would be useful in humans.

Individuals infected by HIV-1 typically develop antibodies that neutralize the virus in vitro, and neutralization titers decrease with disease progression (19). Analysis of sera from HIV-1-infected humans indicates that type-specific neutralizing antibodies appear early in infection. Later in the course of infection, a more broadly neutralizing antibody response develops. However this antibody response is of significantly lower titer and/or affinity.

Fractionation studies of HIV-1 antibody-positive human sera reveal that the type-specific neutralizing activity is primarily directed against linear determinants in the V3 loop of gp120 (20). There was no correlation found among antibodies between the ability to neutralize divergent HIV-1 isolates and reactivity to the V3 loop of these isolates. In contrast, the broadly neutralizing antibodies present in HIV-1 antibody-positive human sera primarily recognize discontinuous epitopes in gp120 which overlap the CD4-binding site and block gp120-CD4 binding. In other words, the broadly neutralizing activity of neutralizing antibodies is not merely the result of additive anti-V3 loop reactivities against diverse HIV-1 isolates which appear during infection.

Recently, several groups have generated human monoclonal antibodies (hMoAbs) derived from HIV-1 infected individuals which possess type-specific or group-common neutralizing activities (17). The type-specific neutralizing hMoAbs were found to recognize linear determinants in the V3 loop of gp120. In contrast, the group-common neutralizing hMoAbs generally recognize discontinuous epitopes which overlap the CD4-binding site and block gp120 -CD4 binding.

The V3 loop is a highly immunodominant region of gp120 which partially interacts with the CD4-binding region. The presence of the V3 loop region on gp120 may skew the humoral immune response away from producing antibodies which specifically bind to the CD4-binding domain of gp120. Furthermore, the advantages of removing the V3 loop to expose the CD4-binding domain of gp120 to the immune system would be countered by the fact that the exposed CD4-binding site would still have a high affinity for cell surface CD4. In other words, a mutant gp120 protein missing only the V3 loop would quickly bind to CD4+ cells and would thus be hampered in generating an immune response against the exposed CD4-binding site.

The subject invention provides a mutant HIV-1 gp120 envelope glycoprotein which overcomes both the problems of V3 loop immunodominance and of the high affinity to CD4. The subject invention further provides vaccines comprising the mutant HIV-1 gp120 envelope glycoprotein, antibodies which specifically bind to the CD4-binding site of HIV-1 gp120 envelope glycoprotein, pharmaceutical compositions comprising these antibodies, and methods of using these vaccines and compositions to treat or prevent HIV-1 infection.

SUMMARY OF THE INVENTION

The subject invention provides a recombinant nucleic acid molecule which encodes a mutant HIV-1 gp120 envelope glycoprotein comprising a V3 loop deletion and a C4 domain$_{(W \to X)}$ point mutation, wherein X is an amino acid residue other than tryptophan. In the preferred embodiment, X is a valine residue.

In one embodiment, the nucleic acid molecule is a DNA molecule. The DNA molecule may be a plasmid. In one embodiment, the plasmid comprises the sequence of the plasmid designated PPI4-tPA.

In one embodiment, the C4 domain is an HIV-1$_{LAI}$ gp120 envelope glycoprotein C4 domain. The mutant HIV-1 gp120 envelope glycoprotein may be a mutant HIV-1$_{LAI}$ gp120 envelope glycoprotein.

In another embodiment, the C4 domain is an HIV-1$_{JR-FL}$ gp120 envelope glycoprotein C4 domain. The mutant HIV-1 gp120 envelope glycoprotein may be a mutant HIV-1$_{JR-FL}$ gp120 envelope glycoprotein.

The subject invention also provides the mutant HIV-1 gp120 envelope glycoprotein encoded by the recombinant nucleic acid molecule of the subject invention.

The subject invention further provides a vaccine which comprises a therapeutically effective amount of the mutant HIV-1 gp120 envelope glycoprotein of the subject invention, and an adjuvant.

The subject invention further provides a method of treating an HIV-1-infected subject, which comprises immunizing the HIV-1-infected subject with the vaccine of the subject invention, thereby treating the HIV-1-infected subject.

The subject invention further provides a vaccine which comprises a prophylactically effective amount of the mutant HIV-1 gp120 envelope glycoprotein of the subject invention, and an adjuvant.

The subject invention further provides a method of reducing the likelihood of an HIV-1-exposed subject's becoming infected with HIV-1, which comprises immunizing the HIV-1-exposed subject with the vaccine of the subject invention, thereby reducing the likelihood of the HIV-1-exposed subject's becoming infected with HIV-1.

The subject invention further provides a method of reducing the likelihood of a non-HIV-1-exposed subject's becoming infected with HIV-1, which comprises immunizing the non-HIV-1-exposed subject with the vaccine of the subject invention, thereby reducing the likelihood of the non-HIV-1-exposed subject's becoming infected with HIV-1.

The subject invention further provides a method of obtaining partially purified antibodies which specifically bind to the CD4-binding domain of HIV-1 gp120 envelope glycoprotein, which method comprises (a) immunizing a non-HIV-1-exposed subject with the vaccine of the subject invention, (b) recovering from the immunized subject serum comprising said antibodies, and (c) partially purifying said antibodies, thereby obtaining partially purified antibodies which specifically bind to the CD4-binding domain of HIV-1 gp120 envelope glycoprotein. In the preferred embodiment, the subject is a human.

The subject invention further provides the partially purified antibodies produced by the method of the subject invention.

The subject invention further provides a pharmaceutical composition, which comprises a therapeutically effective amount of the partially purified antibodies of the subject invention, and a pharmaceutically acceptable carrier.

The subject invention further provides a method of treating an HIV-1-infected subject, which comprises administering to the subject a dose of the pharmaceutical composition of the subject invention effective to reduce the population of HIV-1-infected cells in the HIV-1-infected subject, thereby treating the HIV-1-infected subject.

The subject invention further provides a method of treating an HIV-1-infected subject, which comprises administering to the subject a dose of the pharmaceutical composition of the subject invention effective to reduce the population of HIV-1 in the HIV-1-infected subject, thereby treating the HIV-1-infected subject.

The subject invention further provides a composition which comprises a prophylactically effective amount of the partially purified antibodies of the subject invention, and a pharmaceutically acceptable carrier.

The subject invention further provides a method of reducing the likelihood of an HIV-1-exposed subject's becoming infected with HIV-1, which comprises administering to the HIV-1-exposed subject a dose of the composition of the subject invention effective to reduce the population of HIV-1 in the HIV-1-exposed subject, thereby reducing the likelihood of the subject's becoming infected with HIV-1.

In one embodiment, the subject is a medical practitioner. In another embodiment, the subject is a newborn infant.

Finally, the subject invention provides a method of reducing the likelihood of a non-HIV-1-exposed subject's becoming infected with HIV-1 as a result of exposure thereto during an incident wherein there is an increased risk of exposure to HIV-1, which comprises administering to the subject immediately prior to the incident a dose of the composition of the subject invention effective to reduce the population of HIV-1 to which the subject is exposed during the incident, thereby reducing the likelihood of the subject's becoming infected with HIV-1. In one embodiment, the subject is a medical practitioner.

BRIEF DESCRIPTION OF THE FIGURES

FIG. 1 gp120 structure. Shown is a box diagram of HIV-1 gp120 depicting the boundaries of the five constant domains. (C1–C5) and the five variable domains (V1–V5). The amino acid residue numbering above the box begins at the initiator methionine found at the beginning of the signal sequence (S) and is approximated based on a consensus of all known HIV-1 gp120 amino acid sequences. Also shown are the C4 domain amino acid sequences of HIV-1 strains LAI and JR-FL. Above the C4 domain sequences are indicated two mutations that reduce gp120 binding to cell surface CD4; tryptophan to valine and aspartate to alanine.

FIG. 2

Figure 1:
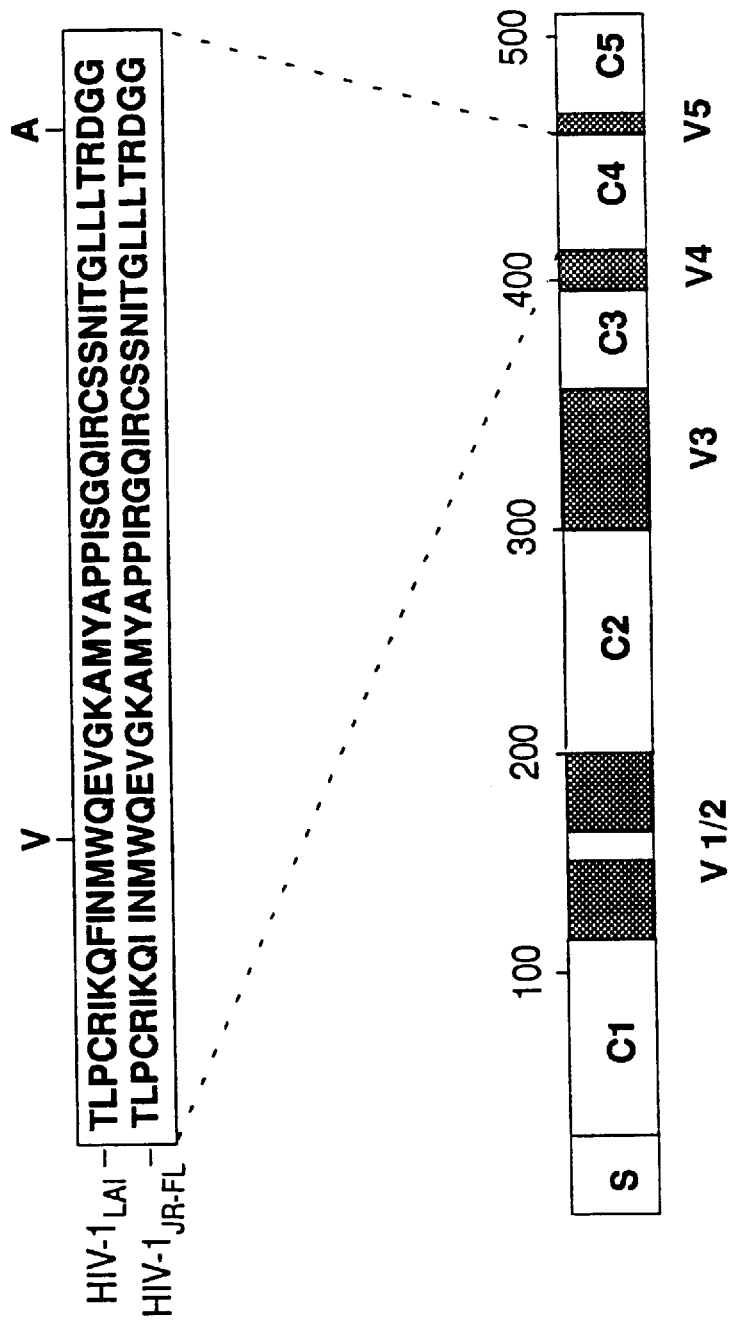

PPI4-tPA-gp120$_{LAI}$. Expression vector with the HIV-1$_{LAI}$ gp120 gene fused to the CMV MIE promoter, and the tPA signal sequence replacing the HIV-1 gp120 signal sequence. Abbreviations: CMV MIE=cytomegalovirus major immediate early, E=enhancer, P=promoter, EXA=Exon A, INA=Intron A, EXB=Exon B, tPA ss=human tissue plasminogen activator signal sequence, gp120=glycoprotein 120, BGH=bovine growth hormone, AMP=ampicillin resistance gene, and DHFR=dihydrofolate reductase gene.

FIGS. 3A, 3B, 3C, 3D, 3E, and 3F

CMV MIE promoter fused to tPA-gp120$_{LAI}$. The nucleotide sequence of the CMV MIE promoter/enhancer region is shown fused to the HIV-1$_{LAI}$ gp120 gene that contains the tPA signal sequence. The numbering of nucleotide sequence begins with the HincII site and the numbering of the amino acid sequence begins with the first methionine found in the tPA signal sequence. The tPA signal sequence is fused in-frame to Thr$_{31}$ of gp120, the first amino acid found in mature gp120. The signal sequence is shown in bold as are various landmark restriction sites used for cloning as discussed in the text. The locations of Exon A, Intron A, Exon B and the transcription start site and the signal cleavage site are indicated.

FIG. 4

Transient expression of gp120. Autoradiograph of $^{35}$S-labeled supernatants from COS cell transfectants, immunoprecipitated with a CD4-immunoglobulin-Protein A-Sepharose complex, and run on a reducing 10% SDS-PAGE gel. The plasmids used for transfection were: Lane 1: Mock transfected cells; lane 2: a vector encoding a CD4-immunoglobulin chimera as a positive transfection control; lane 3: PPI4-tPA-gp120$_{LAI}$; and lane 4: PPI4-tPA-gp120$_{JR-FL}$. Positions of molecular weight markers are indicated.

FIG. 5

Determination of gp120 concentration by ELISA. FIG. 5A: Concentrations of gp120 in media of CHO cell lines, stably transfected with PPI4-tPA-gp120$_{LAI}$, determined by ELISA. FIG 5B: A standard curve was established using known amounts of gp120.

FIG. 6

Expression of gp120 in stably transfected CHO cells. Autoradiograph of $^{35}$S-labeled supernatants from stable CHO cell lines, immunoprecipitated with a CD4-immunoglobulin-Protein A-Sepharose complex, and run on a reducing 10% SDS-PAGE gel. Lane 1: clone 9; lane 2: clone 13; lane 3: clone 6; lane 4: Clone 5. Positions of molecular weight markers are indicated.

FIGS. 7A, 7B, and 7C tPA-gp120$_{JR-FL}$. The nucleotide and deduced amino acid sequence of the tPA signal sequence fused to HIV-1$_{JR-FL}$ gp120 is shown. The NarI and NotI restriction endonuclease sites used for cloning are shown in bold. The predicted site of cleavage by signal peptidase between Arg$_{35}$ and Val$_{36}$ is indicated.

FIGS. 8A, 8B, and 8C tPA-gp120$_{LAI}$-V3$^{(-)}$. The nucleotide and deduced amino acid sequence of the tPA signal sequence fused to HIV-1$_{LAI}$ gp120 with the V3 loop deleted and replaced with the pentapeptide TGAGH is shown. The V3 loop replacement and the NarI and NotI restriction endonuclease sites used for cloning are shown in bold. The predicted site of cleavage by signal peptidase between Arg$_{35}$ and Thr$_{36}$ is indicated.

FIGS. 9A, 9B, and 9C tPA-gp120$_{JR-FL}$-V3$^{(-)}$. The nucleotide and deduced amino acid sequence of the tPA signal sequence fused to HIV-1$_{JR-FL}$ gp120 with the V3 loop deleted and replaced with the pentapeptide TGAGH is shown. The V3 loop replacement and the NarI and NotI restriction endonuclease sites used for cloning are shown in bold. The predicted site of cleavage by signal peptidase between $Arg_{35}$ and $Val_{36}$ is indicated.

FIGS. 10A, 10B, and 10C tPA-gp120$_{LAI}$-V3$^{(-)}$-CD4$^{(-)}$. Shown is the nucleotide and deduced amino acid sequence of the tPA signal sequence fused to HIV-1$_{LAI}$ gp120, with the V3 loop deleted and replaced with the pentapeptide TGAGH, and $Trp_{408}$ mutated to Val. The mutations and the NarI and NotI restriction endonuclease sites used for cloning are shown in bold. The predicted site of cleavage by signal peptidase between $Arg_{35}$ and $Thr_{36}$ is indicated.

Figure 11A:
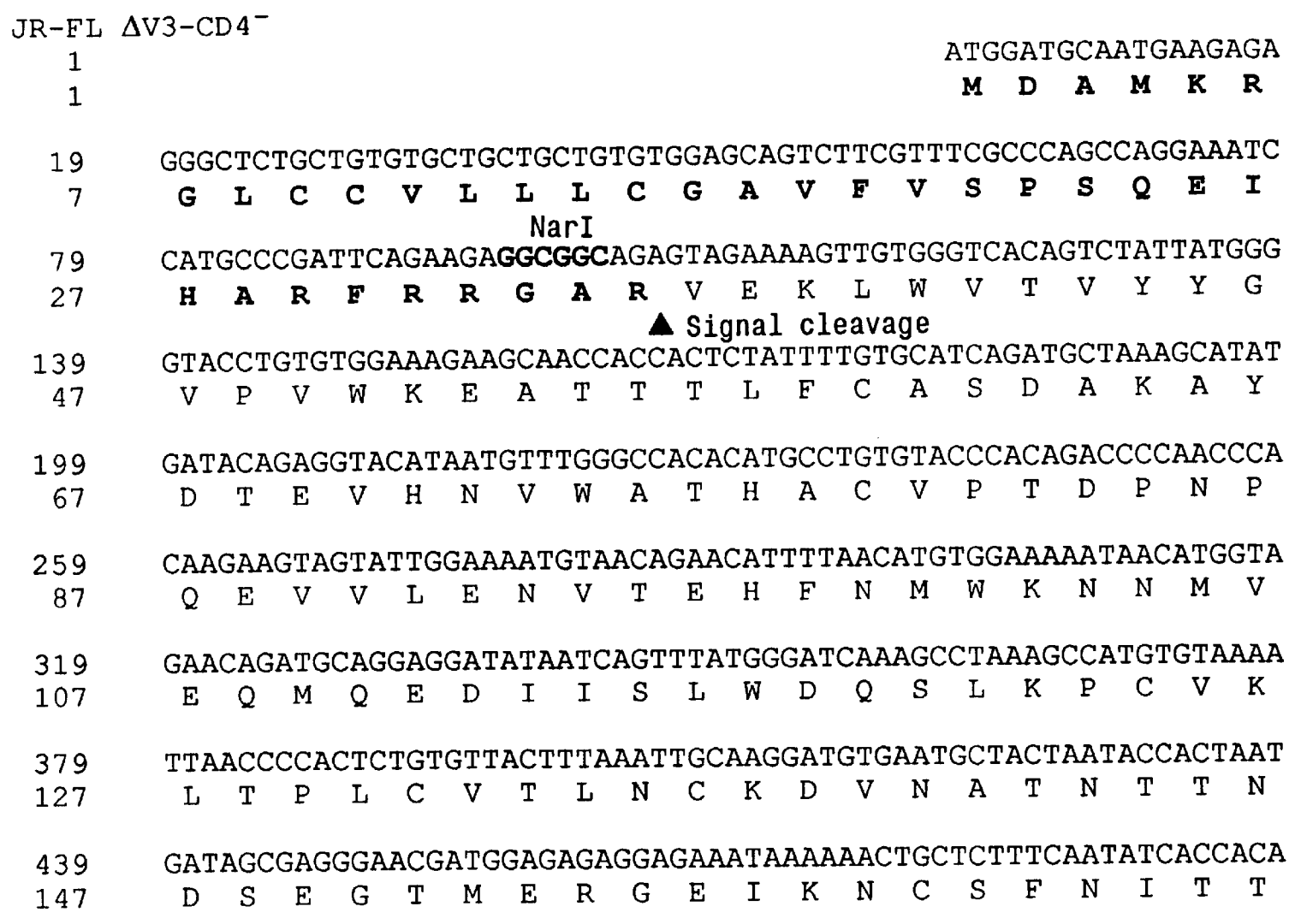

FIGS. 11A, 11B, and 11C, tPA-gp120$_{JR-FL}$-V3$^{(-)}$-CD41$^{(-)}$. Shown is the nucleotide and deduced amino acid sequence of the tPA signal sequence fused to HIV-1$_{JR-FL}$ gp120, with the V3 loop deleted and replaced with the pentapeptide TGAGH, and $Trp_{396}$ mutated to Val. The mutations and the NarI and NotI restriction endonuclease sites used for cloning are shown in bold. The predicted site of cleavage by signal peptidase between $Arg_{35}$ and $Val_{36}$ is indicated.

FIGS. 12A, 12B, and 12C tPA-gp120$_{LAI}$-CD4$^{(-)}$. Shown is the nucleotide and deduced amino acid sequence of the tPA signal sequence fused to HIV-1$_{LAI}$ gp120. The $Trp_{437}$ to Val CD4 binding mutation, the NarI and NotI restriction endonuclease sites used for cloning, and the predicted site of cleavage by signal peptidase between $Arg_{35}$ and $Thr_{36}$ are shown in bold.

FIG. 13A, 13B, 13C, and 13D tPA-gp120$_{JR-FL}$-CD4$^{(-)}$. Shown is the nucleotide and deduced amino acid sequence of the tPA signal sequence fused to HIV-1$_{JR-FL}$ gp120. The $Trp_{424}$ to Val CD4 binding mutation, the NarI and NotI restriction endonuclease sites used for cloning and the predicted cleavage by signal peptidase between $Arg_{35}$ and $Val_{36}$ are shown in bold.

Figure 14A:
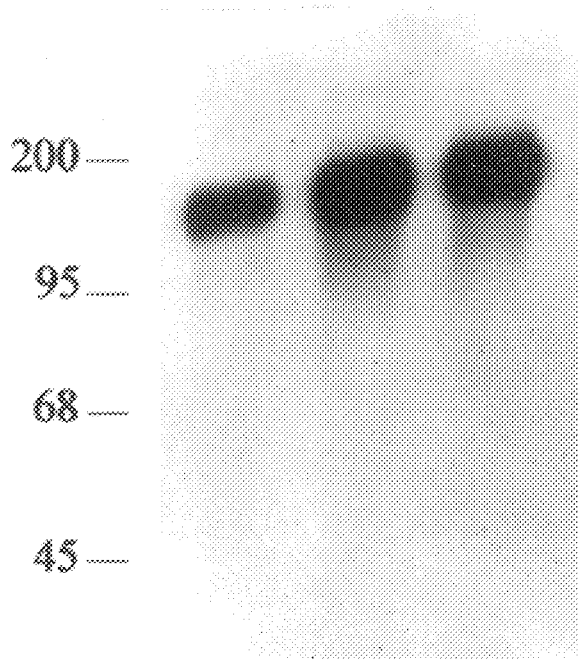
Figure 14B:
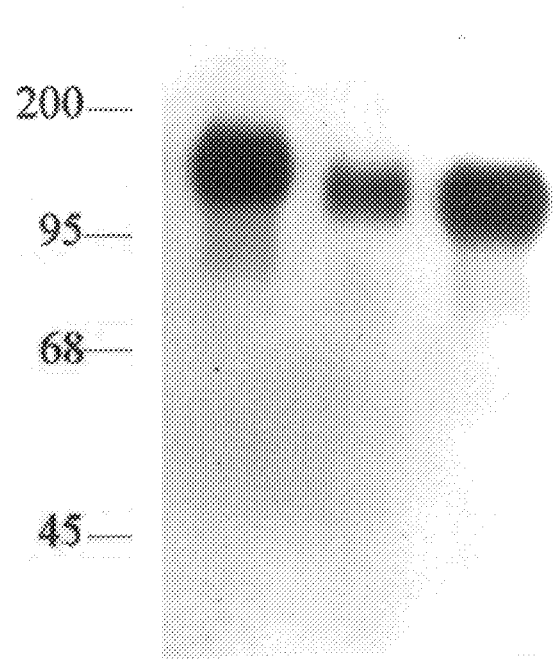

FIGS. 14A and 14B

Expression of gp120 in stably transfected CHO cells. Autoradiograph of super $^{35}$S-labeled supernatants from stable CHO cell lines, immunoprecipitated with MoAb F105-Protein A-Sepharose complex, and run on a reducing 10% SDS-PAGE gel. FIG. 14A: Lane 1: tPA-gp120$_{LAI}$ CHO cells; lane 2: tPA-gp120$_{LAI}$-V3$^{(-)}$ CHO cells; lane 3: tPA-gp120$_{LAI}$-V3$^{(-)}$-CD4$^{(-)}$ CHO cells. FIG. 14B: Lane 1: tPA-gp120$_{JR-FL}$ CHO cells; lane 2: tPA-gp120$_{JR-FL}$-V3$^{(-)}$ CHO cells; lane 3: tPA- gp120$_{JR-FL}$-V3$^{(-)}$-CD4$^{(-)}$ CHO cells. Positions of molecular weight markers are indicated.

Figure 15A:
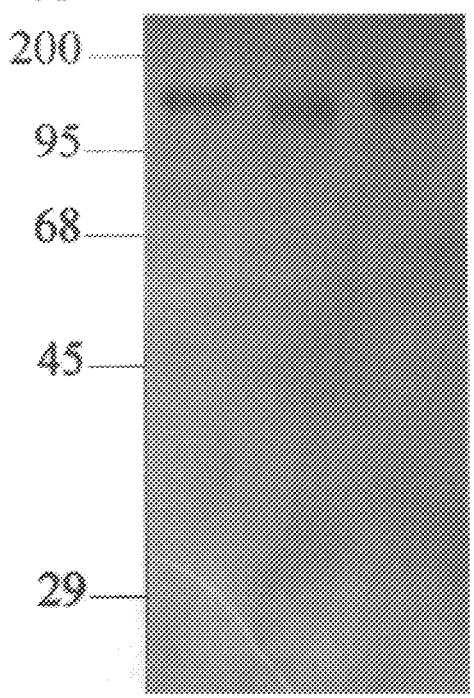
Figure 15B:
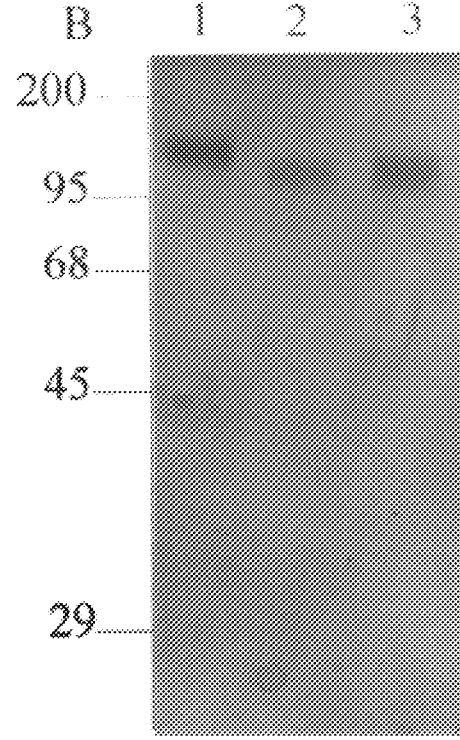

FIGS. 15A and 15B

Purified gp120 proteins. Silver stained 10% SDS-PAGE gel with a sample of purified gp120 proteins. FIG. 15A: Lane 1: tPA-gp120$_{LAI}$ CHO cells; lane 2: tPA-gp120$_{LAI}$-V3$^{(-)}$ CHO cells; lane 3: tPA-gp120$_{LAI}$-V3$^{(-)}$-CD4$^{(-)}$ CHO cells. FIG. 15B: Lane 1: tPA-gp120$_{JR-FL}$ CHO cells; lane 2: tPA-gp120$_{JR-FL}$-V3$^{(-)}$ CHO cells; lane 3: tPA-gp120$_{JR-FL}$-V3$^{(-)}$-CD4$^{(-)}$ CHO cells. Positions of molecular weight markers are indicated.

FIG. 16A–16D

Figure 16A:
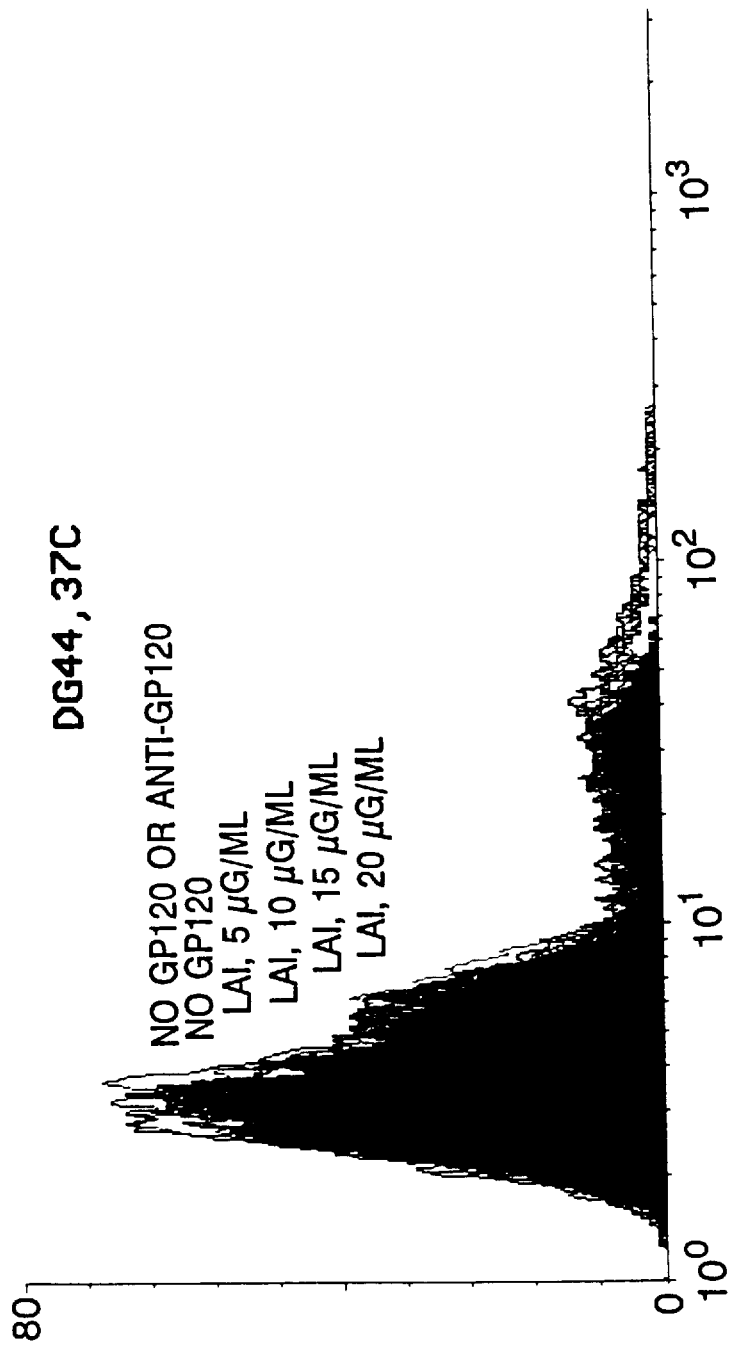

Analysis of binding of recombinant mutant gp120 to cell surface human CD4 by FACS. FIG. 16A. DG44 cells, a subclone of CHO cells which lack expression of the human CD4 protein, were used as control. Increasing concentrations of HIV-1 gp120$_{LAI}$ did not show an increase in specific fluoresence when compared to background. FIG. 16B. DG44 #3 cells are a CHO cell line transfected with the cDNA clone encoding the human CD4 protein. Increasing concentrations of HIV-1 gp120$_{LAI}$ show a dramatic increase (or shift) in fluoresence. FIG. 16C. Similar to Plate 2 but the HIV-1 gp120$_{LAI}$-V3$^{(-)}$ protein was added. Again a large shift indicating binding to the DG44 #3 cells was seen. FIG. 16D. DG44 #3 cells were incubated with either HIV-1 gp120$_{LAI}$-V3$^{(-)}$-CD4$^{(-)}$ protein or MoAb OKT4A an antibody with high affinity for human CD4. Only OKT4A bound to the cells.

DETAILED DESCRIPTION OF THE INVENTION

The plasmids designated PPI4-tPA-gp120$_{LAI}$ and PPI4-tPA-gp120$_{JR-FL}$ were deposited pursuant to, and in satisfaction of, the requirements of the Budapest Treaty on the International Recognition of the Deposit of Microorganisms for the Purposes of Patent Procedure with the American Type Culture Collection (ATCC), 12301 Parklawn Drive, Rockville, Md. 20852 under ATCC Accession Nos. 75431 and 75432, respectively. The plasmids PPI4-tPA-gp120$_{LAI}$ and PPI4-tPA-gp120$_{JR-FL}$ were deposited with the ATCC on Mar. 12, 1993.

The subject invention provides a recombinant nucleic acid molecule which encodes a mutant HIV-1 gp120 envelope glycoprotein comprising a V3 loop deletion and a C4 domain$_{(W \to X)}$ point mutation, wherein X is an amino acid residue other than tryptophan. In the preferred embodiment, X is a valine residue.

In one embodiment, the nucleic acid molecule is a DNA molecule. The DNA molecule may be a plasmid. In one embodiment, the plasmid comprises the sequence of the plasmid designated PPI4-tPA.

The V3 loop of HIV-1 gp120 envelope glycoprotein is shown in FIG. 1. The V3 loop is demarcated by cysteine residues at both its N- and C-termini. As used herein, a V3 loop deletion means a deletion of one or more amino acid residues between the terminal cysteine residues, with the proviso that there must be three or more amino acid residues situated between the two terminal cysteine residues in a V3 loop deletion. These three or more amino acid residues may either be residues originally present in the V3 loop, or exogenous residues. For example, as shown in the Experimental Details section infra, the pentapeptide TGAGH is situated between the two terminal cysteine residues. Variations in the size of the V3 loop deletion illustrated herein are tolerable without affecting the overall structure of the mutant HIV-1 gp120 envelope glycoprotein, as is-well known to those skilled in the art.

As used herein, "C4 domain" means the HIV-1 gp120 envelope glycoprotein C4 domain having the following consensus sequence:

$X_1X_2X_3CX_4IX_5X_6X_7X_8X_9X_{10}WX_{11}X_{12}X_{13}X_{14}X_{15}$
$AX_{16}YX_{17}X_{18}PX_{19}X_{20}X_{21}X_{22}X_{23}X_{24}X_{25}X_{26}SX_{27}X_{28}$
$TGX_{29}X_{30}X_{31}X_{32}RX_{33}GX_{34}$, wherein $X_1$=T, I, V, K or R; $X_2$=L, I or H; $X_3$=P, Q, L or T; $X_4$=R, K or G; $X_5$=K or E; $X_6$=Q or E; $X_7$=F, I or V; $X_8$=I, V or M; $X_9$=N, R or K; $X_{10}$=M, R, L or T; $X_{11}$=Q, R or V; $X_{12}$=E, K, G, R, V or A; $X_{13}$=V, T, A or G; $X_{14}$=G or E; $X_{15}$=K, R, E, or Q; $X_{16}$=M, V, I or L; $X_{17}$=A, T or D; $X_{18}$=P or L; $X_{19}$=I or F; $X_{20}$=S, R, G, K, N, A, E or Q; $X_{21}$=G or R; $X_{22}$=Q, L, P, N, K, V, T, E or I; $X_{23}$=I, V or L; $X_{24}$=R, K, S, N, G, I, T, E or I; $X_{25}$=C or R; $X_{26}$=S, L, I, T, P, E, V, K, D or N; $X_{27}$=N, K or L; $X_{28}$=I or V; $X_{29}$=L, P or I; $X_{30}$=L or I; $X_{31}$=L or I; $X_{32}$=T, A, I, V or E; $X_{33}$=D or E; $X_{34}$=G or V.

The C4 domain consensus sequence is based on existing C4 domain sequence information from various HIV-1 strains, and thus is not necessarily an exhaustive consensus sequence. The conserved tryptophan residue shown in bold after residue $X_{10}$ is the only conserved tryptophan residue in the C4 domain. As used herein, a C4 domain$_{(W \rightarrow X)}$ point mutation is a mutation of the above-identified conserved C4 domain tryptophan residue to an amino acid residue other than tryptophan. For example, a C4 domain$_{(W \rightarrow X)}$ point mutation is a mutation of the conserved C4 domain tryptophan residue to a valine residue.

In one embodiment, the C4 domain is an HIV-1$_{LAI}$ gp120 envelope glycoprotein C4 domain. The sequence of the HIV-1$_{LAI}$ gp120 C4 domain is: TLPCRIKQFINM-WQEVGKAMYAPPISGQIRCSSNITGLLLTRDGG. The mutant HIV-1 gp120 envelope glycoprotein may be a mutant HIV-1$_{LAI}$ gp120 envelope glycoprotein.

In another embodiment, the C4 domain is an HIV-1$_{JR-FL}$ gp120 envelope glycoprotein C4 domain. The sequence of the HIV-1$_{JR-FL}$ gp120 C4 domain is: TLPCRIKQIINM-WQEVGKAMYAPPIRGQIRCSSNITGLLLTRDGG. The mutant HIV-1 gp120 envelope glycoprotein may be a mutant HIV-1$_{JR-FL}$ gp120 envelope glycoprotein.

HIV-1$_{LAI}$ is a laboratory-adapted strain that is tropic for phytohemagglutinin (PHA)-stimulated peripheral blood lymphocytes (PBLs) and immortalized human T-cell lines. In contrast, HIV-1$_{JR-FL}$ was isolated from brain tissue taken at autopsy that was co-cultured with lectin-activated normal human PBLs. HIV-1$_{JR-FL}$ is tropic for PHA-stimulated PBLs and blood-derived macrophages but will not replicate in transformed T-cell lines. Mutant HIV-1 gp120 envelope glycoproteins derived from a clinical isolate of HIV-1 such as JR-FL may possess new or different epitopes compared to the laboratory-adapted HIV-1 strains that are beneficial for successful vaccination. Although only the HIV-1$_{LAI}$ and HIV-1$_{JR-FL}$ strains are used herein to generate the mutant HIV-1 gp120 envelope glycoproteins of the subject invention, other HIV-1 strain could be substituted in their place as is well known to those skilled in the art.

The V1 and V2 variable regions of gp120 are unnecessary for CD4 binding (21). Therefore the mutant HIV-1 gp120 envelope glycoprotein of this invention can either include or exclude the V1 and V2 variable regions.

The subject invention additionally provides a recombinant nucleic acid molecule which encodes a mutant HIV-1 gp120 envelope glycoprotein comprising a V3 loop deletion and a C4 domain$_{(Asp \rightarrow X)}$ point mutation, wherein the aspartate residue is between amino acid residues $X_{15}$ and $X_{16}$ in the C4 consensus sequence, and X is an amino acid residue other than aspartate or glutamate. In the preferred embodiment, X is an alanine residue.

The subject invention additionally provides a recombinant nucleic acid molecule which encodes a mutant HIV-1 gp120 envelope glycoprotein comprising a V3 loop deletion and a C4 domain$_{(Glu \rightarrow X)}$ point mutation, wherein the glutamate residue is between amino acid residues $X_{15}$ and $X_{16}$ in the C4 consensus sequence, and X is an amino acid residue other than aspartate or glutamate. In the preferred embodiment, X is an alanine residue.

The subject invention additionally provides a recombinant nucleic acid molecule which encodes a mutant HIV-1$_{LAI}$ gp120 envelope glycoprotein comprising a V3 loop deletion and a C3 domain$_{(asp378 \rightarrow X)}$ point mutation, wherein X is an amino acid residue other than aspartate or glutamate. In the preferred embodiment, X is a lysine residue.

The subject invention additionally provides a recombinant nucleic acid molecule which encodes a mutant HIV-1$_{JR-FL}$ gp120 envelope glycoprotein comprising a V3 loop deletion and a C3 domain$_{(asp369 \rightarrow X)}$ point mutation, wherein X is an amino acid residue other than aspartate or glutamate. In the preferred embodiment, X is a lysine residue.

The subject invention additionally provides a recombinant nucleic acid molecule which encodes a mutant HIV-1$_{LAI}$ gp120 envelope glycoprotein comprising a V3 loop deletion and a C3 domain$_{(glu380 \rightarrow X)}$ point mutation, wherein X is an amino acid residue other than glutamate. In the preferred embodiment, X is a glutamine residue.

The subject invention additionally provides a recombinant nucleic acid molecule which encodes a mutant HIV1$_{JR-FL}$ gp120 envelope glycoprotein comprising a V3 loop deletion and a C3 domain$_{(glu371 \rightarrow X)}$ point mutation, wherein X is an amino acid residue other than glutamate. In the preferred embodiment, X is a glutamine residue.

The subject invention additionally provides a recombinant nucleic acid molecule which encodes a mutant HIV-1$_{LAI}$ gp120 envelope glycoprotein comprising a V3 loop deletion and a C2 domain$_{(thr267 \rightarrow X)}$ point mutation, wherein X is an amino acid residue other than threonine. In the preferred embodiment, X is an arginine residue.

The subject invention additionally provides a recombinant nucleic acid molecule which encodes a mutant HIV-1$_{JR-FL}$ gp120 envelope glycoprotein comprising a V3 loop deletion and a C2 domain$_{(thr260 \rightarrow X)}$ point mutation, wherein X is an amino acid residue other than threonine. In the preferred embodiment, X is an arginine residue.

The subject invention additionally provides a recombinant nucleic acid molecule which encodes a mutant HIV-1 gp120 envelope glycoprotein comprising (a) a V3 loop deletion, or (b) a one of the C2, C3 or C4 domain point mutations discussed supra.

The point mutations in the recombinant nucleic acid molecules described supra are selected based on their ability to reduce the affinity of the mutant gp120 glycoprotein encoded thereby for CD4. As used herein, the term "reduce the affinity" means to reduce the affinity by at least two-fold.

One skilled in the art would know how to make recombinant nucleic acid molecules which encode mutant HIV-1 gp120 envelope glycoproteins comprising a V3 loop deletion and the specific C2, C3 or C4 domain point mutations corresponding to those mutations exemplified in the HIV-1$_{JR-FL}$ and HIV-1$_{LAI}$ strains, supra. Furthermore, one skilled in the art would know how to use these recombinant nucleic acid molecules to obtain the proteins encoded thereby, and practice the therapeutic and prophylactic methods of using same, as described herein for the recombinant nucleic acid molecule which encodes a mutant HIV-1 gp120 envelope glycoprotein comprising a V3 loop deletion and a C4 domain$_{(W \rightarrow X)}$ point mutation.

The subject invention also provides the mutant HIV-1 gp120 envelope glycoprotein encoded by the recombinant nucleic acid molecule of the subject invention.

In accordance with the invention, numerous vector systems for expression of the mutant HIV-1 gp120 envelope glycoprotein may be employed. For example, one class of vectors utilizes DNA elements which are derived from animal viruses such as bovine papilloma virus, polyoma virus, adenovirus, vaccinia virus, baculovirus, retroviruses (RSV, MMTV or MoMLV), Semliki Forest virus or SV40 virus.

Additionally, cells which have stably integrated the DNA into their chromosomes may be selected by introducing one or more markers which allow for the selection of transfected host cells. The marker may provide, for example, prototropy to an auxotrophic host, biocide resistance, (e.g., antibiotics) or resistance to heavy metals such as copper or the like. The selectable marker gene can be either directly linked to the DNA sequences to be expressed, or introduced into the same cell by cotransformation. Additional elements may also be needed for optimal synthesis of mRNA. These elements may include splice signals, as well as transcriptional promoters, enhancers, and termination signals. The cDNA expression vectors incorporating such elements include those described by Okayama (22).

The vectors used in the subject invention are designed to express high levels of mutant HIV-1 gp120 envelope glycoproteins in cultured eukaryotic cells as well as efficiently secrete these proteins into the culture medium. The targeting of the mutant HIV-1 gp120 envelope glycoproteins into the culture medium is accomplished by fusing in-frame to the mature N-terminus of the mutant HIV-1 gp120 envelope glycoprotein the tissue plasminogen activator (tPA) prepro-signal sequence.

The mutant HIV-1 gp120 envelope glycoprotein may be produced by a) transfecting a mammalian cell with an expression vector for producing mutant HIV-1 gp120 envelope glycoprotein; b) culturing the resulting transfected mammalian cell under conditions such that mutant HIV-1 gp120 envelope glycoprotein is produced; and c) recovering the mutant HIV-1 gp120 envelope glycoprotein so produced.

Once the expression vector or DNA sequence containing the constructs has been prepared for expression, the expression vectors may be transfected or introduced into an appropriate mammalian cell host. Various techniques may be employed to achieve this, such as, for example, protoplast fusion, calcium phosphate precipitation, electroporation or other conventional techniques. In the case of protoplast fusion, the cells are grown in media and screened for the appropriate activity. Expression of the gene encoding a mutant HIV-1 gp120 envelope glycoprotein results in production of the mutant glycoprotein.

Methods and conditions for culturing the resulting transfected cells and for recovering the mutant HIV-1 gp120 envelope glycoprotein so produced are well known to those skilled in the art, and may be varied or optimized depending upon the specific expression vector and mammalian host cell employed.

In accordance with the claimed invention, the preferred host cells for expressing the mutant HIV-1 gp120 envelope glycoprotein of this invention are mammalian cell lines. Mammalian cell lines include, for example, monkey kidney CV1 line transformed by SV40 (COS-7); human embryonic kidney line 293; baby hamster kidney cells (BHK); Chinese hamster ovary-cells-DHFR (CHO); Chinese hamster ovary-cells DHFR$^-$ (DXB11); monkey kidney cells (CV1); African green monkey kidney cells (VERO-76); human cervical carcinoma cells (HELA); canine kidney cells (MDCK); human lung cells (W138); human liver cells (Hep G2); mouse mammary tumor (MMT 060562); mouse cell line (C127); and myeloma cell lines.

Other eukaryotic expression systems utilizing non-mammalian vector/cell line combinations can be used to produce the mutant HIV-1 gp120 envelope glycoproteins. These include, but are not limited to, baculovirus vector/insect cell expression systems and yeast shuttle vector/yeast cell expression systems.

Methods and conditions for purifying mutant HIV-1 gp120 envelope glycoproteins from the culture media are provided in the invention, but it should be recognized that these procedures can be varied or optimized as is well known to those skilled in the art.

The subject invention further provides a vaccine which comprises a therapeutically effective amount of the mutant HIV-1 gp120 envelope glycoprotein of the subject invention, and an adjuvant.

A therapeutically effective amount of the mutant HIV-1 gp120 envelope glycoprotein may be determined according to methods well known to those skilled in the art.

As used herein, adjuvants include, but are not limited to, alum, Freund's incomplete adjuvant (FIA), Saponin, Quil A, Monophosphoryl lipid A (MPL), and nonionic block copolymers (SAF) such as L-121 (Pluronic; Syntex SAF). In the preferred embodiment, the adjuvant is alum, especially in the form of a thixotropic, viscous, and homogeneous aluminum hydroxide gel. The vaccine of the subject invention may be administered as an oil in water emulsion. Methods of combining adjuvants with antigens are well known to those skilled in the art.

The subject invention further provides a method of treating an HIV-1-infected subject, which comprises immunizing the HIV-1-infected subject with the vaccine of the subject invention, thereby treating the HIV-1-infected subject.

As used herein, treating an HIV-1-infected subject with the vaccine of the subject invention means reducing in the subject either the population of HIV-1 or HIV-1-infected cells, or ameliorating the progression of an HIV-1-related disorder in the subject.

As used herein, an "HIV-infected subject" means an individual having at least one of his own cells invaded by HIV-1.

As used herein, "immunizing" means administering a primary dose of the vaccine to a subject, followed after a suitable period of time by one or more subsequent administrations of the vaccine, so as to generate in the subject an immune response against the CD4-binding region of the mutant HIV-1 gp120 envelope glycoprotein in the vaccine. A suitable period of time between administrations of the vaccine may readily be determined by one skilled in the art, and is usually in the order of several weeks to months.

In the preferred embodiment, the dose of vaccine administered is an amount sufficient to deliver to the subject between 10ug and 1mg of the mutant HIV-1 gp120 envelope glycoprotein.

The subject invention further provides a vaccine which comprises a prophylactically effective amount of the mutant HIV-1 gp120 envelope glycoprotein of the subject invention, and an adjuvant.

A prophylactically effective amount of the mutant HIV-1 gp120 envelope glycoprotein may be determined according to methods well known to those skilled in the art.

The subject invention further provides a method of reducing the likelihood of an HIV-1-exposed subject's becoming infected with HIV-1, which comprises immunizing the HIV-1-exposed subject with the vaccine of the subject invention, thereby reducing the likelihood of the HIV-1-exposed subject's becoming infected with HIV-1.

As used herein, the subject's becoming infected with HIV-1 means the invasion of the subject's own cells by HIV-1.

As used herein, reducing the likelihood of a subject's becoming infected with HIV-1 means reducing the likelihood of the subject's becoming infected with HIV-1 by at least two-fold. For example, if a subject has a 1% chance of becoming infected with HIV-1, a two-fold reduction in the likelihood of the subject's becoming infected with HIV-1 would result in the subject's having a 0.5% chance of becoming infected with HIV-1. In the preferred embodiment of this invention, reducing the likelihood of the subject's becoming infected with HIV-1 means reducing the likelihood of the subject's becoming infected with HIV-1 by at least ten-fold.

As used herein, an HIV-1-exposed subject is a subject who has HIV-1 present in his body, but has not yet become HIV-1-infected.

The subject invention further provides a method of reducing the likelihood of a non-HIV-1-exposed subject's becoming infected with HIV-1, which comprises immunizing the non-HIV-1-exposed subject with the vaccine of the subject invention, thereby reducing the likelihood of the non-HIV-1-exposed subject's becoming infected with HIV-1.

As used herein, a non-HIV-1-exposed subject is a subject who does not have HIV-1 present in his body.

The subject invention further provides a method of obtaining partially purified antibodies which specifically bind to the CD4-binding domain of HIV-1 gp120 envelope glycoprotein, which method comprises (a) immunizing a non-HIV-1-exposed subject with the vaccine of the subject invention, (b) recovering from the immunized subject serum comprising said antibodies, and (c) partially purifying said antibodies, thereby obtaining partially purified antibodies which specifically bind to the CD4-binding domain of HIV-1 gp120 envelope glycoprotein. In the preferred embodiment, the subject is a human.

As used herein, partially purified antibodies means a composition which comprises antibodies which specifically bind to the CD4-binding domain of HIV-1 gp120 envelope glycoprotein, and consists of fewer protein impurities than does the serum from which the anti-CD4-binding domain antibodies are derived. A protein impurity means a protein other than the anti-CD4-binding domain antibodies. For example, the partially purified antibodies might be an IgG preparation.

Methods of recovering serum from a subject are well known to those skilled in the art. Methods of partially purifying antibodies are also well known to those skilled in the art, and include, by way of example, filtration, ion exchange chromatography, and precipitation.

In one embodiment, the partially purified antibodies comprise an immune globulin (IG) preparation. IG can be purified from serum by a two-step process. Initially, serum is fractionated by the cold ethanol method of Cohn, et al. (29). Cohn Fraction II has as its main protein component IgG immunoglobulin present as monomers, dimers and aggregates. Fraction II is then purified to produce IVIG (immune globulin intravenous) using a variety of purification methods which include, for example, ion exchange, DEAE chromatography, acid pH 4.25 diafiltration, PEG precipitation or Pepsin treatment. The final product is stabilized (e.g., glucose+NaCl) and the final. IgG concentration is fixed at between about 3% and about 6%.

The subject invention further provides the partially purified antibodies produced by the method of the subject invention.

The subject invention further provides a pharmaceutical composition, which comprises a therapeutically effective amount of the partially purified antibodies of the subject invention, and a pharmaceutically acceptable carrier.

A therapeutically effective amount of the partially purified antibodies of the subject invention may be determined according to methods well known to those skilled in the art.

Pharmaceutically acceptable carriers are well known to those skilled in the art and include, but are not limited to, 0.01–0.1M and preferably 0.05M phosphate buffer or 0.8% saline. Additionally, such pharmaceutically acceptable carriers may be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases and the like.

The subject invention further provides a method of treating an HIV-1-infected subject, which comprises administering to the subject a dose of the pharmaceutical composition of the subject invention effective to reduce the population of HIV-1-infected cells in the HIV-1-infected subject, thereby treating the HIV-1-infected subject.

As used herein, administering may be effected or performed using any of the various methods known to those skilled in the art. The administering may comprise administering intravenously. The administering may also comprise administering intramuscularly. The administering may further comprise administering subcutaneously.

The dose of the pharmaceutical composition of the subject invention effective to reduce the population of HIV-1-infected cells in the HIV-1-infected subject may be readily determined using methods well known to those skilled in the art. In the preferred embodiment, the dose is sufficient to deliver to the subject between about 10 mg/kg and 150 mg/kg of protein if administered intramuscularly. In the preferred embodiment, the dose is sufficient to deliver to the subject between about 100 mg/kg and 2 g/kg of protein if administered intravenously.

The subject invention further provides a method of treating an HIV-1-infected subject, which comprises administering to the subject a dose of the pharmaceutical composition of the subject invention effective to reduce the population of HIV-1 in the HIV-1-infected subject, thereby treating the HIV-1-infected subject.

The dose of the pharmaceutical composition of the subject invention effective to reduce the population of HIV-1 in the HIV-1-infected subject may be readily determined using methods well known to those skilled in the art. In the preferred embodiment, the dose is sufficient to deliver to the subject between about 10 mg/kg and 150 mg/kg of protein if administered intramuscularly. In the preferred embodiment, the dose is sufficient to deliver to the subject between about 100 mg/kg and 2 g/kg of protein if administered intravenously.

The subject invention further provides a composition which comprises a prophylactically effective amount of the partially purified antibodies of the subject invention, and a pharmaceutically acceptable carrier.

A prophylactically effective amount of the partially purified antibodies of the subject invention may be determined according to methods well known to those skilled in the art.

The subject invention further provides a method of reducing the likelihood of an HIV-1-exposed subject's becoming infected with HIV-1, which comprises administering to the HIV-1-exposed subject a dose of the composition of the subject invention effective to reduce the population of HIV-1 in the HIV-1-exposed subject, thereby reducing the likelihood of the subject's becoming infected with HIV-1.

In one embodiment, the subject is a medical practitioner. The medical practitioner may be a medical practitioner exposed to an HIV-1-containing bodily fluid. As used herein, the term "medical practitioner" includes, but is in no way limited to, doctors, dentists, surgeons, nurses, medical laboratory assistants, and students in health care programs.

In another embodiment, the subject is a newborn infant. The newborn infant may be a newborn infant born to an HIV-1-infected mother.

The dose of the composition of the subject invention effective to reduce the population of HIV-1 in the HIV-1-exposed subject may be readily determined using methods well known to those skilled in the art. In the preferred embodiment, the dose is sufficient to deliver to the subject between about 10 mg/kg and 150 mg/kg of protein if administered intramuscularly. In the preferred embodiment, the dose is sufficient to deliver to the subject between about 100 mg/kg and 2 g/kg of protein if administered intravenously.

The vaccines and pharmaceutical compositions of the subject invention may also ameliorate the progression of an HIV-1-related disorder in a subject to whom the vaccines or pharmaceutical compositions were administered while the subject was either non-HIV-1-exposed or HIV-1-exposed, but not yet HIV-1-infected.

Finally, the subject invention provides a method of reducing the likelihood of a non-HIV-1-exposed subject's becoming infected with HIV-1 as a result of exposure thereto during an incident wherein there is an increased risk of exposure to HIV-1, which comprises administering to the subject immediately prior to the incident a dose of the composition of the subject invention effective to reduce the population of HIV-1 to which the subject is exposed during the incident, thereby reducing the likelihood of the subject's becoming infected with HIV-1. In one embodiment, the subject is a medical practitioner.

An incident wherein there is an increased risk of exposure to HIV-1 includes, for example, receiving a blood transfusion, sexual contact with an HIV-1-infected individual, and performing a HIV-1-containing bodily fluid-exposing medical procedure.

As used herein, "immediately prior to the incident" means within one month of the incident. In the preferred embodiment, "immediately prior to the incident" means within one day of the incident.

The dose of the composition of the subject invention effective to reduce the population of HIV-1 to which the subject is exposed during the incident may be readily determined using methods well known to those skilled in the art. In the preferred embodiment, the dose is sufficient to deliver to the subject between about 10 mg/kg and 150 mg/kg of protein if administered intramuscularly. In the preferred embodiment, the dose is sufficient to deliver to the subject between about 100 mg/kg and 2 g/kg of protein if administered intravenously.

One embodiment of this invention is a method of substantially reducing the likelihood of a non-infected medical practitioner's becoming infected with HIV-1 during a bodily fluid-exposing medical procedure involving a patient, which comprises administering to the patient during a suitable time period an amount of the composition of the subject invention effective to substantially reduce the likelihood of the non-infected medical practitioner's becoming infected with HIV-1 by virtue of contact with the patient's bodily fluid during the medical procedure.

As used herein, a bodily fluid is any fluid which is present in the human body and is capable of containing infectious HIV-1 in an HIV-1-infected patient. Bodily fluids include, but are not limited to, saliva, cerebrospinal fluid, tears, vaginal secretions, urine, alveolar fluid, synovial fluid and pleural fluid.

Another embodiment of this invention is a method of substantially reducing the likelihood of a non-HIV-1-infected newborn infant's becoming infected with HIV-1 prior to or during birth from an HIV-1-infected mother, which comprises administering to the mother prior to birth an amount of the composition of the subject invention effective to substantially reduce the likelihood of the non-HIV-1-infected newborn infant's becoming infected with HIV-1 by virtue of contact with the patient's bodily fluid.

In order to facilitate an understanding of the Experimental Details section which follows, certain frequently occurring methods and/or terms are best described in Maniatis et al. (23).

This invention will be better understood by reference to the Experimental Details which follow, but those skilled in the art will readily appreciate that the specific experiments detailed are only illustrative of the invention as described more fully in the claims which follow thereafter.

Experimental Details

Nomenclature

As used herein, $V3^{(-)}$ indicates a V3 loop deletion from HIV-1 gp120 envelope glycoprotein. As used herein, $CD4^{(-)}$ indicates a point mutation in the C4 domain of HIV-1 gp120 envelope glycoprotein which mutation inhibits CD4 binding to the mutant HIV-1 gp120 envelope glycoprotein. The structure of HIV-1 gp120 envelope glycoprotein is shown in FIG. 1.

Materials and Methods

1. Construction of PPI4-tPA-gp120$_{LAI}$ expression vector.

An expression vector was constructed that consisted of the cytomegalovirus major immediate early (CMV MIE) promoter/enhancer linked to the HIV-1$_{LAI}$env gene, which gene had its signal sequence replaced by the tPA signal sequence. The CMV MIE promoter/enhancer sequences were derived from pSVCC1 (24) consisting of 1580 base pairs of contiguous DNA that is immediately 5' to the initiator ATG. In sequential order, the functional domains of the CMV promoter are: the promoter/enhancer region; a transcriptional initiator site; exon A (a non-coding exon); intron A; and 17 nucleotides of exon B (non-coding sequences). The viral promoter sequences were ligated to a gene construct consisting of the nucleotide sequences encoding amino acids −35 to −1 of human tPA (25) fused in-frame to HIV-1$_{LAI}$env amino acids 31 through 515, ending with a TGA stop codon. The construction was performed in two parts. The majority of the CMV promoter could be isolated as a 1560 bp Hinc II/Pst I fragment which was ligated to a Pst I/Not I 1590 bp DNA fragment that contained the remainder of the CMV promoter, the initiator ATG, the tPA signal sequence and the mature HIV-1$_{LAI}$ env protein coding sequence.

Figure 2:
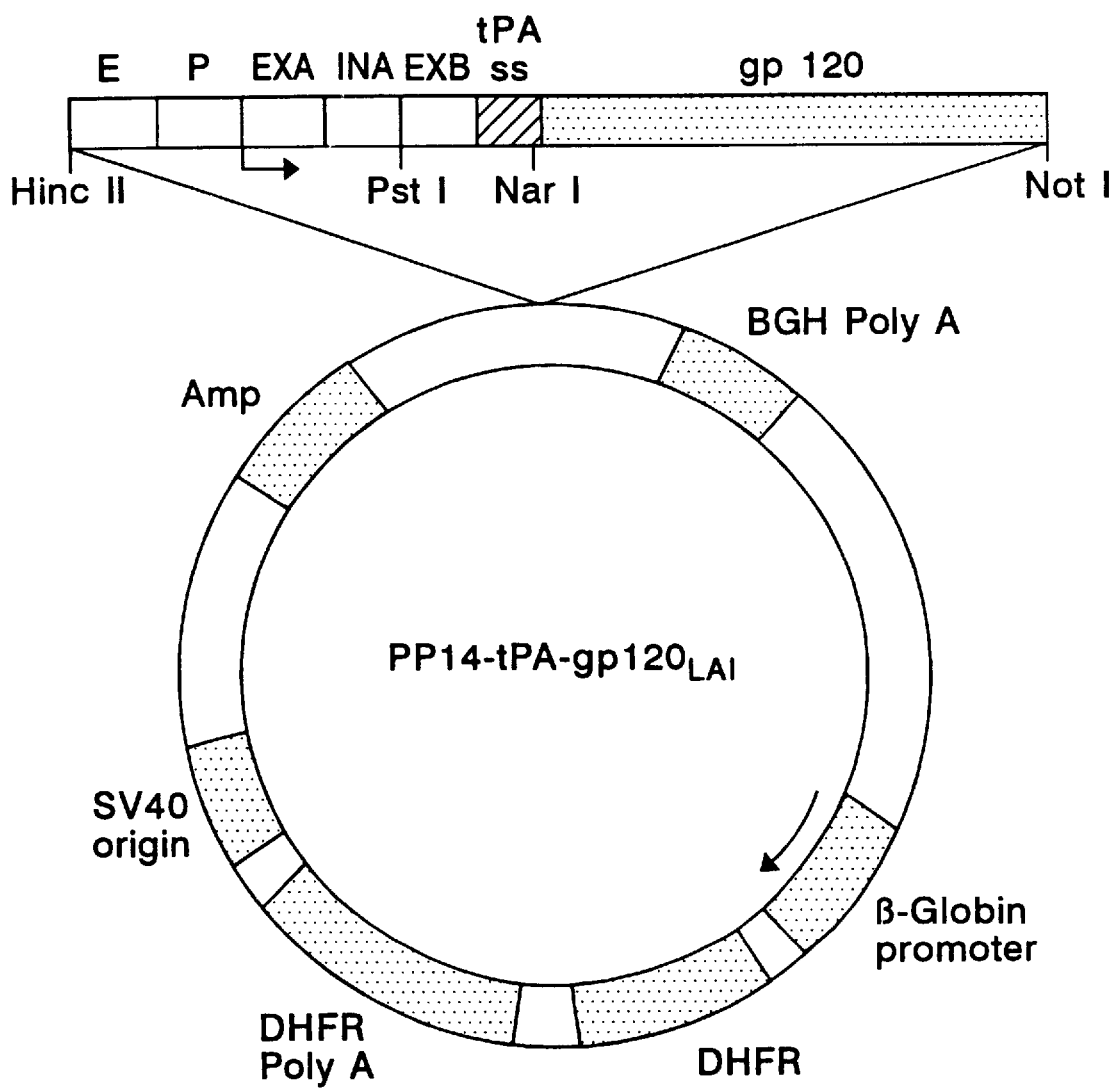
Figure 6:
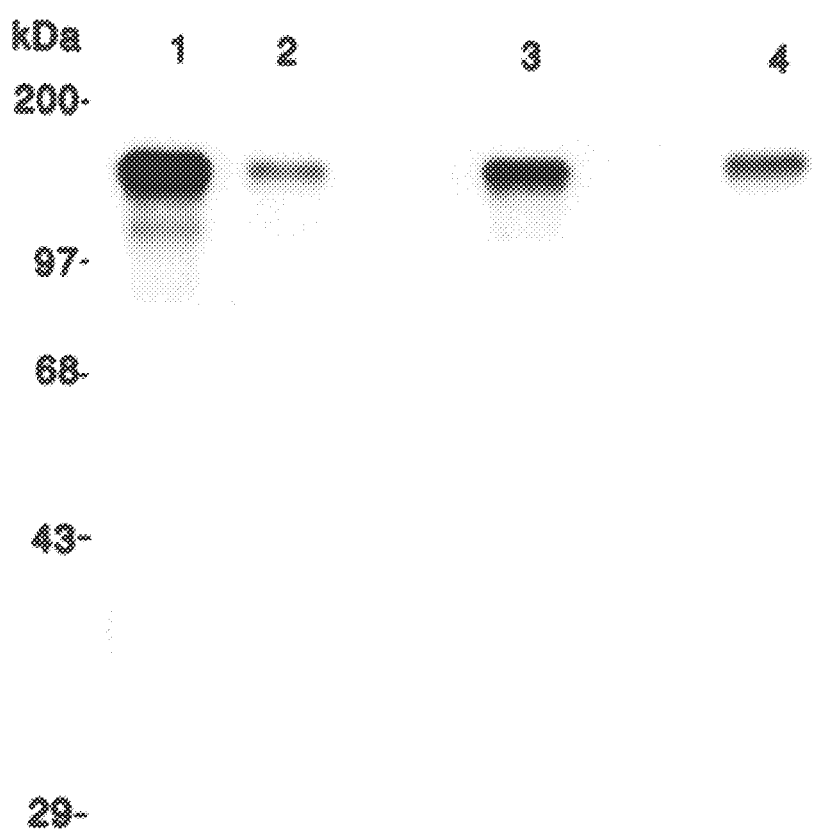

The latter fragment was assembled using the polymerase chain reaction as follows. Primer 1 (GATCCTGCAGTCACCGTCCTTGACACGATGGATG-CAATGAAGAGA) and primer 2 (AAGTC-TTCTCCTCGGTCTTGTCTRTTTTAACACCCAG) were used to amplify the nucleic acid sequences encoding the tPA signal sequence amino acids−35 to−1 from plasmid PMAM neo-s (Clonetech), thus producing a 150 bp fragment. A second 1440 bp DNA fragment was amplified using primer 3 (TTCAGAAGAGGAGCCAGAACAGAAAAATTG-TGGGTC), primer 4 (GGAAAAAA-GCGGCCGCTCATTTTTCTCTCTGCACCACTC), and pENV (26) as a template. The PCR fragments were pooled, desalted, and excess primer removed by ultrafiltration through a centricon-100 unit (Amicon). An aliquot of the pooled material was then subjected to a second round of amplification in the presence of primers 1 and 4 to produce a 1590 bp fragment, which was then digested with Pst I and Not I. The CMV promoter fragment and the HIV-1$_{LAI}$env fragment were then ligated together, and the entire transcription unit subcloned into PPI4, which is a eukaryotic shuttle vector that contains an ampicillin resistance gene, an SV40 origin of replication and a DHFR gene whose transcription is driven by the β-globin promoter. The final construct, PPI4-tPA-gp120$_{LAI}$, is shown in FIG. 2.

The expression vector is then used as the prototype vector for the expression of gp120 proteins that are derived from other HIV-1 strains or mutated as described in the methods section. The vector was constructed so that unique Nar I and Not I sites flank the gp120 sequence, thus facilitating the removal of the gp120 gene cassette and the subsequent insertion of other gene cassettes (FIG. 2).

2. Expression of HIV-1$_{LAI}$120 in mammalian cells.

a. Transient expression.

CosM5 cells grown in DMEM containing 10% fetal calf serum were split to 75% confluence. On the following day, the cells were transfected for 16–20 hours with 10 micrograms of CsCl-purified PPI4-tPA-gp120$_{LAI}$ DNA by the standard $CaPO_4$ (5) precipitation technique. After transfection, fresh medium was added to the cells. Analysis of the products synthesized 96–120 hours post-transfection was performed by radiolabelling the transfectants with $^{35}$S-cysteine for 12–18 hours, followed by precipitation of media using a CD4-immunoglobulin-Protein A-Sepharose complex, followed by SDS-PAGE under reducing conditions (FIG. 4).

b. Stable expression. Dhfr$^-$ Chinese hamster ovary cells (CHO) were transfected with 20 micrograms of CsCl-purified DNA. Approximately 3–5 days post-transfection, cells were placed in selective medium (nucleoside-free alpha MEM containing 10% dialyzed fetal calf serum). Approximately 10–15 days post-selection, individual cell clones were picked. Media was analyzed for gp120 expression by radiolabelling the cells with $^{35}$S-cystein cysteine for 12–18 hours, followed by precipitation of media using a CD4-immunoglobulin-Protein A-Sepharose complex, followed in turn by SDS-PAGE under reducing conditions (FIG. 6). The levels of gp120 in the media of these clones were also quantitated (FIG. 5) by ELISA performed as follows. The method involves coating 96-well plates overnight with sheep polyclonal IgG against the highly conserved C-terminus of gp120 (D7234, Aalto Bioreagents). After washing, dilutions of a standard gp120 preparation in cell growth medium, or supernatant from the stably-transfected cells, were incubated for 1 hour. The plates were washed again, and incubated for one hour with a horseradish peroxidase-conjugated anti-gp120 monoclonal antibody (9204, DuPont). Following a final wash, the peroxidase substrate OPD (DuPont) was added and the amount of gp120 determined by comparing absorbance of unknowns with a standard curve. Standards were prepared from purified gp120 made in CHO cells, a small quantity of which was obtained from Celltech Ltd. Clones expressing the highest levels were subjected to successive rounds of amplification of the newly introduced DNA sequences in increasing concentrations of methotrexate. Stable CHO cell lines were thus generated which secrete at least 1 microgram/milliliter of HIV-1$_{LAI}$ gp120.

3. Construction of PPI4-tPA-gp120$_{JR-FL}$.

a. The HIV-1$_{LAI}$ gp120 env nucleotide sequence in PPI4-tPA-gp120$_{LAI}$ was replaced by the nucleotide sequence encoding the mature gp120$_{JR-FL}$ protein. Using the polymerase chain reaction, the JR-FL sequences were amplified from pUC112-1 (27) using primer 5 (GATCGGCGCCAGAGTAGAAAAGTTGTGGGTCAC) and primer 4. The PCR fragment was digested with the restriction endonucleases Nar I and Not I, and the fragment subcloned in between the Nar I and Not I sites in PPI4-tPA-gp120$_{LAI}$ to generate PPI4-tPA-gp120$_{JR-FL}$ (FIG. 7).

b. Transient expression.

CosMS cells grown in DMEM containing 10% fetal calf serum were split to 75% confluence. On the following day, the cells were transfected for 16–20 hours with 10 micrograms of CsCl-purified PPI$^4$-tPA-gp120$_{JR-FL}$ DNA by the standard $CaPO_4$ (5) precipitation technique. After transfection, fresh medium was added to the cells. Analysis of the products synthesized 96–120 hours post-transfection was performed by radiolabelling the transfectants with $^{35}$S-cysteine for 12–18 hours, followed by precipitation of media using a CD4-immunoglobulin-Protein A-Sepharose complex, followed by SDS-PAGE under reducing conditions (FIG. 4).

4. Construction of PPI4-tPA-gp120$_{LAI}$-V3$^{(-)}$.

The V3 loop in tPA-gp120$_{LAI}$ consists of amino acids $Cys_{306}$ through $Cys_{333}$. In the V3$^{(-)}$ mutant, the amino acids in between these cysteines are replaced by the pentapeptide sequence Thr-Gly-Ala-Gly-His. Using the Transformer Site-Directed Mutagenesis Kit (Clonetech), the V3 loop sequence in PPI4-tPA-gp120$_{LAI}$ is altered using the mutagenic primer 6 (CTGTA-GAAATTAATTGTACAGGTGCTGGACATTGTAACA-TTAGTAGAGC) and primer 7 (CTCGAGCATGCATTCGAAGCTCGCTGATC) as a selection primer. Primer 7 changes a unique Xba I site in the backbone of the parent PPI4 plasmid into a unique BstB I site. Briefly, the mutagenesis method requires incubating of the parent plasmid with the mutagenic primer and the selection primer, denaturing at 100° C. for 3 minutes and then chilling on ice. In the presence of buffered deoxynucleotide triphosphates and T4 DNA polymerase, the primers are allowed to initiate the polymerization of one strand of plasmid DNA. T4 DNA ligase is used to seal the newly synthesized DNA strand to form a covalently closed circle. Hybrid plasmids are then transformed into a MutS strain of *E. coli* that is deficient in mismatch repair. After allowing for the growth of transformed cells, DNA is purified from the cells and digested with the selection restriction endonuclease, in this case Xba I. Parental plasmids are cleaved by Xba I while the mutant plasmid remains resistant to cleavage by virtue of the Xba I to BstB I conversion. Digested DNA is then used to transform *E. coli*, and colonies harboring the mutant plasmid are picked. Multiple mutagenic primers can be used in a single round of mutagenesis. The amino acid sequence of the modified protein is shown in FIG. 8.

5. Construction of PPI4-tPA-gp120$_{JR-FL}$-V3$^{(-)}$.

The V3 loop in tPA-gp120$_{JR-FL}$ consists of amino acids $Cys_{293}$ through $Cys_{327}$. In the V3$^{(-)}$ mutant, the amino acids in between these cysteines are replaced by the pentapeptide sequence Thr-Gly-Ala-Gly-His. Using the Transformer Site-Directed Mutagenesis Kit (Clonetech), the V3 loop sequence in PPI4-tPA-gp2$_{JR-FL}$ is altered using the mutagenic primer 6 (CTGTAG-AAATTAATTGTACAGGTGCTGGACATTGTAACATT-AGTAGAGC) and primer 7 as a selection primer. The amino acid sequence of the modified protein is shown in FIG. 9.

6. Construction of PPI4-tPA-gp120$_{LAI}$-CD4$^{(-)}$.

Using the Transformer Site-Directed Mutagenesis Kit (Clonetech), the selection primer 7, and the mutagenic primer 8 (CAATTTATAAACATGGTGCAGGAAGTAGG), $Trp_{437}$ of tPA-gp120$_{LAI}$, which is in an equivalent position to the tryptophan residue in the HXBc2 strain of HIV-1, is mutated to a Val in the expression vector PPI4-tPA-gp120$_{LAI}$ to generate PPI4-tPA-gp120$_{LAI}$-CD4$^{(-)}$. The sequence for gp120$_{LAI}$-CD4$^{(-)}$ is shown in FIG. 12.

7. Construction of PPI4-tPA-gp120$_{JR-FL}$-CD4$^{(-)}$.

In a fashion similar to that described above, Trp$_{424}$ of tPA-gp120$_{JR-FL}$ is mutated to a Val in the expression vector PPI4-tPA-gp120$_{JR-FL}$ using the selection primer 7 and the mutagenic primer 9 (CAAATTATAAACATGGTGCAGGAAGTAGG) to generate PPI4-tPA-gp120$_{JR-FL}$-CD4$^{(-)}$. The sequence for gp120$_{JR-FL}$-CD4$^{(-)}$ is shown in FIG. 13.

8. Construction of PPI4-tPA-gp120$_{LAI}$-V3$^{(-)}$-CD4$^{(-)}$.

The tPA-gp120$_{LAI}$ double mutant, V3$^{(-)}$-CD4$^{(-)}$, is constructed by including the mutagenic primers 6 and 8, and the selection primer 7 simultaneously in the reaction tube with PPI4-tPA-gp120$_{LAI}$ as the DNA template. The final construct is named PPI4-tPA-gp120$_{LAI}$-V3$^{(-)}$-CD4$^{(-)}$ and its sequence is shown in FIG. 10.

9. Construction of PPI4-tPA-gp120$_{JR-FL}$-V3$^{(-)}$-CD4$^{(-)}$.

The tPA-gp120$_{JR-FL}$ double mutant, V3$^{(-)}$-CD4$^{(-)}$, is constructed by including the mutagenic primers 6 and 9, and the selection primer 7 simultaneously in the reaction tube with PPI4-tPA-gp120$_{JR-FL}$ as the DNA template. The final construct is named PPI4-tPA-gp120$_{JR-FL}$-V3$^{(-)}$-CD4$^{(-)}$, and its sequence is shown in FIG. 11.

10. Expression of mutant HIV-1 gp120 in mammalian cells.

a. Transient expression.

CosM5 cells grown in DMEM containing 10% fetal calf serum are split to 75% confluence. On the next day, the cells are transfected for 16–20 hours with 10 micrograms of CsCl-purified mutant HIV-1 DNA by the standard CaPO$_4$ (5) precipitation technique. After transfection, fresh medium is added to the cells. Analysis of the products synthesized 96–120 hours post-transfection is performed by radiolabelling the transfectants with $^{35}$S-cysteine for 12–18 hours, followed by precipitation of media using a sheep polyclonal IgG against the highly conserved C-terminus of gp120.

b. Stable expression.

Dhfr$^-$ Chinese hamster ovary cells (CHO) are transfected with 20 micrograms of CsCl-purified DNA encoding the native or mutant HIV-1 gp120 glycoproteins. Approximately 3–5 days post-transfection, cells are placed in selective medium (nucleoside-free alpha MEM containing 10% dialyzed fetal calf serum). Approximately 10–15 days post-selection, individual cell clones are picked. Media is analyzed for gp120 expression by radiolabelling the cells with $^{35}$S-cysteine for 12–18 hours, followed by quantitative immunoprecipitation of media using a sheep polyclonal IgG against the highly conserved C-terminus of gp120, followed in turn by SDS-PAGE under reducing conditions. Alternatively, one can quantitate the level of gp120 by ELISA performed as follows. The method involves coating 96-well plates overnight with sheep polyclonal IgG against the highly conserved C-terminus of gp120 (D7234, Aalto Bioreagents). After washing, dilutions of a standard gp120 preparation in cell growth medium, or supernatant from the stably-transfected cells, are incubated for 1 hour. The plates are washed again, and incubated for one hour with a human MoAb (F105, AIDS Research & Reference Reagent Program, No. 857). The plates are washed again, and incubated again for 1 hour with a horseradish-peroxidase-conjugated goat anti-human IgG (Cappel). Following a final wash, the peroxidase substrate OPD (DuPont) is added and the amount of gp120 determined by comparing absorbance of unknowns with a standard curve. Standards are prepared from purified gp120 made in CHO cells, a small quantity of which is obtained from Celltech Ltd. Clones expressing the highest levels are subjected to successive rounds of amplification of the newly introduced DNA sequences in increasing concentrations of methotrexate. Stable CHO cell lines are thus generated which secrete at least 1 microgram/milliliter of mutant HIV-1 gp120.

11. Purification of HIV-1 qp120 proteins.

A one-step immunoaffinity procedure is used to purify the recombinant gp120 molecules described. Briefly, culture supernatant is collected and clarified by centrifugation. An immunoaffinity column consisting of a matrix coupled to a sheep polyclonal anti-gp120 IgG (D7234, Aalto Bioreagents) directed against the highly conserved C-terminal end (APTKAKRRVVQREKR) of gp120 is used to specifically adsorb gp120 from the cell culture media. This antisera recognizes native gp120, the V3 loop deletion mutants, and the CD4$^{(-)}$ mutants since the C-terminal ends of these molecules remain unaltered. The bound gp120 is then eluted with 2M MgCl$_2$, concentrated by Amicon filtration, and dialyzed into 10 mM HEPES, pH 7.0. The purity of the proteins is determined by SDS-PAGE and silver staining.

12. Characterization of recombinant HIV-1 gp120 proteins.

The purified glycoproteins are subjected to extensive biochemical and immunologic characterization. The integrity of the proteins is monitored by SDS-PAGE and silver staining under reducing and non-reducing conditions. The glycoproteins are deglycosylated by treatment with the enzyme N-glycosidase F which cleaves N-linked oligo-saccharides, and are assayed by SDS-PAGE and silver staining to monitor molecular weight shifts. The purified glycoproteins are also tested for reactivity with several well characterized anti-gp120 monoclonal antibodies that recognize both linear and discontinuous epitopes. The binding affinity to sCD4 is estimated using an ELISA assay.

The purified proteins HIV-1 gp120$_{LAI}$, gp120$_{LAI}$-V3$^{(-)}$, gp120$_{LAI}$-V3$^{(-)}$-CD4$^{(-)}$, gp120$_{JR-FL}$, gp120$_{JR-FL}$-V3$^{(-)}$, and gp120$_{JR-FL}$-V3$^{(-)}$-CD4$^{(-)}$, were tested for their ability to bind cell surface human CD4. DG44 #3 cells, a recombinant cell line designed to express human CD4 on the membrane surface, were grown in T flasks and trypsinized. 5×10$^5$ cells/experiment were aliquoted into FACS buffer (PBS+2% BSA and 0.1% NaN$_3$), washed several times in the same buffer, and then incubated with 100 ul of a solution of purified gp120 protein at 5 ug/ml in FACS buffer at 37° C. for 2 hr. The cells were washed in FACS buffer, and then incubated in 100 ul solution containing 5 ug/ml sheep polyclonal IgG against the highly conserved C-terminus of gp120 in FACS buffer at 37° C. for 2 hr. The cells were washed in FACS buffer then incubated in 100 ul solution containing FITC-labeled rabbit anti-sheep IgG polyclonal antibody at 37° C. for 2 hr. The cells were washed with FACS buffer and then resuspended in 500 ul FACS buffer. The cells were then analyzed on a Becton Dickinson FACScan according to the manufacturer's instructions. As a control for expression of CD4 on the DG44 #3 cells, FITC-labeled OKT4A (Becton Dickinson) was used.

13. A protocol for inoculation of animals with the mutant HIV-1 gp120 envelope glycoproteins.

Alum is used as an adjuvant during the inoculation series. The inoculum is prepared by dissolving the mutant HIV-1 gp120 envelope glycoprotein antigen in physiologic saline at a final antigen concentration of 100 ug/ml. Preformed alum (aluminum hydroxide gel) is added to the solution to a final level of 500 ug/ml aluminum. The antigen is allowed to adsorb onto the alum gel for two hours at room temperature. Following adsorption, the gel with the antigen is washed twice with physiologic saline and resuspended in the saline to a protein concentration of 100 ug/ml.

Monkeys and/or Guinea Pigs are individually inoculated with four 100 ug doses of the mutant HIV-1 gp120 envelope glycoprotein antigen adsorbed onto alum. Each dose is injected intramuscularly. The doses are delivered one or five months apart (week 0, 4, 8 and 28). the animals are bled at intervals of two or four weeks. Serum samples are prepared from each bleed to assay for the development of specific antibodies as described in the subsequent sections.

14. Analysis of sera for anti-mutant HIV-1 gp120 envelope glycoprotein IgG antibodies.

Each serum sample is analyzed by ELISA. Polystyrene microtiter plates are coated with 0.5 ug per well of pure mutant HIV-1 gp120 envelope glycoprotein in phosphate-buffered physiological saline (PBS) at 4° C. Each well is then washed with PBS containing 0.5% TWEEN-20 (PBS-TW). Test serum, diluted serially in PBS-TW, is added to the mutant HIV-1 gp120 envelope glycoprotein-containing wells and allowed to react with the adsorbed mutant HIV-1 gp120 envelope glycoprotein for one hour at 37° C. The wells are then washed extensively in PBS-TW. Each well then receives 0.1% p-nitrophenyl phosphate in 10% diethanolamine, pH 9.8, containing 0.5 mM $MgCl_2.6H_2O$. The ensuing reaction is allowed to proceed at room temperature for 30 minutes, at which time it is terminated by the addition of 3.0N NaOH. The greater the interaction of antibodies in the test serum with the mutant HIV-1 gp120 envelope glycoprotein, the greater is the amount of alkaline phosphatase bound onto the well. The phosphatase enzyme mediates the breakdown of p-nitrophenyl phosphate into a molecular substance which absorbs light at a wavelength of 405 nm. Hence, there exists a direct relationship between the absorbance at 405 nm of light at the end of the ELISA reaction and the amount of mutant HIV-1 gp120 envelope glycoprotein-bound antibody. All animals inoculated with mutant HIV-1 gp120 envelope glycoprotein whose serum reacts specifically with the mutant HIV-1 gp120 envelope glycoprotein in the ELISA have a positive antibody response against mutant HIV-1 gp120 envelope glycoprotein.

15. Analysis of sera for activity which specifically neutralizes HIV-1 infectivity.

Virus-neutralizing activity is determined with an assay based on the use of multiplicity curves in which the ratio of infectious virus surviving antibody treatment $V_n$) is compared to infectious virus in uninhibited cultures ($V_o$) at various dilutions of antisera. The neutralization titer of the sera is then interpolated as that sera dilution which yields one log reduction in infectious titer (i.e., $V_n/V_o=0.1$). Briefly, 4-fold dilutions of virus (laboratory-adapted and primary isolates) are prepared to yield infectious doses of 0.1 to 100 $TCID_{50}$ (Tissue Culture Infection Dose) in 20 ul. Serial 3-fold dilutions of sera are also prepared and 20 ul of each serum dilution are incubated with each dilution of virus in duplicate for 60 minutes at room temperature in a 96-well microtiter plate. 20 ul of AA5 cells (PHA stimulated PBMCs for primary HIV-1 isolates) are then added to the serum/virus mixtures. Cells are cultured for 7 days by the addition of fresh medium every other day. On the seventh day, supernatant from each well is removed and tested for the presence of reverse transcriptase (RT). Infection in each well is then scored as either positive or negative based on the RT counts, and the infectious dose of virus in each treatment group is calculated using the Reed and Muench (28) formula. The neutralization titers represent the reciprocal serum dilution required to reduced infectious dose of virus by one log. The above culture time is for the prototypic HIV-$1_{LAI}$ isolate tested on the AA5 cell line. In the case of primary isolates, the termination date is usually 11–14 days. Culture conditions for PBMCs is not as demanding since doubling time is restricted. In the case of PBMCs, one day PHA stimulations are used at a final concentration of $1.5 \times 10^6$/ml on day 0. Half that number of fresh PBMCs are then added again on days 4 and 8. This multiple addition of PBMCs is meant to amplify virus output upon successful infection so that the readout RT signal is strong. Again, the final readout titer for the primary isolate/PBMC is the reciprocal serum dilution which reduces infectious titer by one log.

16. Passive hyperimmune therapy.

Non-HIV-1-infected humans are immunized with the mutant HIV-1 gp120 envelope glycoprotein antigens according to a protocol similar to that described above in section 12. For passive hyperimmune therapy in HIV-1-infected individuals, blood plasma is taken from mutant HIV-1 gp120 envelope glycoprotein immunized, non-HIV-1-infected human donors whose plasma has high levels of neutralizing antibodies. The plasma is pooled from several donors, purified to remove nonimmunoglobulin proteins and is then sterilized to kill any other viruses or pathogens. The treated plasma is then injected into individuals infected with HIV-1, with repeated injections every week, every two weeks, or every month.

Results

Eukaryotic expression vectors designed to express high levels of HIV-$1_{LAI}$ gp120 and HIV-$1_{JR-FL}$ gp120 were constructed. The CMV MIE promoter/enhancer was used to drive the transcription of a gene fusion consisting of the human tPA signal sequence fused to mature gp120 (FIGS. 2 and 7). The complete sequence of the transcription unit from the Hinc II site of the CMV promoter/enhancer to the Not I site just 3' from the stop codon in gp120 is shown in FIG. 3. This vector was used to transfect COSM5 cells in a transient assay. The transfected cells were labeled with $^{35}$S-cysteine and the media immunoprecipitated with a CD4-immunoglobulin-Protein A-Sepharose complex. The precipitated products were analyzed using a reducing 10% SDS-PAGE gel and autoradiography (FIG. 4). A 120 kD band was detected when PPI4-tPA-gp120$_{LAI}$ was used to transfect COS cells (lane 3). A band migrating with a slightly lower molecular mass was detected when PPI4-tPA-gp120$_{JR-FL}$ was used to transfect COS cells (lane 4). No radiolabeled products were detected in the mock infected cells. Using a sheep polyclonal antibody directed against the highly conserved C-terminal end of HIV-1 gp120 in an ELISA assay, the level of expression of HIV-1 gp120 was determined to be 2350 ng/ml.

The PPI4-tPA-gp120$_{LAI}$ vector was then used to stably transfect the dhfr⁻ CHO cell line DXB11. Two days post-transfection, the cells were plated at low density in nucleoside-free medium. Eight days post-transfection, surviving clones were isolated and expanded. Individual primary transfectants were tested for gp120 expression using the ELISA method described in the methods section. Several primary CHO transfectants expressed significant quantities (10–120 ng/ml) of gp120 (FIG. 5). Three of the highest expressing clones were then subjected to increasing concentrations of methotrexate in order to amplify, in tandem, the copy number of the dhfr and gp120 genes. Cell lines were established that express high levels of gp120 with rates of secretion greater than 1 mg/liter. These were then used to purify gp120 to homogeneity.

Six CHO cell lines were established, using the procedures of the following proteins: HIV-1 gp120$_{LAI}$, gp120$_{LAI}$-V3$^{(-)}$, gp120$_{LAI}$-V3$^{(-)}$-CD4$^{(-)}$, gp120$_{JR-FL}$, gp120$_{JR-FL}$-V3$^{(-)}$, and gp120$_{JR-FL}$-V3$^{(-)-CD}$4$^{(-)}$. Metabolic labeling of these cells with $^{35}$S-cysteine followed by immunoprecipitation with the human monoclonal antibody F105 and analyzed by SDS-PAGE and autoradiography showed the presence of the gp120 proteins in the culture supernatant (FIG. 14). From these cell lines the gp120 proteins were purified to homogeneity. Analysis by SDS-PAGE followed by silver-staining showed the purity of these proteins to be greater than 90% (FIG. 15).

It was shown by FACScan analysis that the two CD4 binding mutants HIV-1 gp120$_{LAI}$-V3$^{(-)}$-CD4 and HIV-1 gp120$_{JR-FL}$-V3$^{(-)}$-CD4$^{(-)}$ had no appreciable binding to recombinant cell lines designed to express high levels of human CD4 on their membrane surface (FIG. 16, panel 4 and data not shown, respectively).

Discussion

The advantage of using the mutant HIV-1 gp120 envelope glycoproteins as immunogens is that these proteins will not elicit an immune response against the V3 loop, a highly immunodominant epitope on gp120. This is significant because the V3 loop may skew the humoral immune response away from discontinuous epitopes in the CD4-binding site. Mutant HIV-1 gp120 envelope glycoproteins having partial and total V3 loop deletions have been made (30). Deletion of the V3 loop therefore exposes the CD4-binding site to the immune system, allowing the immune system to mount a response against this critical region (18). Another advantage of using the mutant HIV-1 gp120 envelope glycoprotein as an immunogen is that it has significantly reduced affinity for cell surface CD4. An efficient humoral immune response depends on the binding of antigen to B cell surface immunoglobulin. The presence of the high-affinity CD4 receptor on large numbers of cells in the body may significantly diminish the ability of native gp120 to induce an effective humoral immune response. The rationale of mutating gp120 at the CD4 binding site is to redirect the mutant HIV-1 gp120 envelope glycoprotein away from cell surface CD4 toward immunoglobulin-bearing B cells, thereby allowing the immune system to mount a response against, inter alia, the CD4-binding site.

References

1. Klatzmann, D. R., et. al. (1990) Immunodeficiency Reviews 2, 43–66.
2. Lasky, L. A., et. al. (1987) Cell 50, 975–985.
3. Maddon, P. J., et. al. (1986) Cell 47, 333–348.
4. Maddon, P. J., et. al. (1988) Cell 54, 865–674.
5. Maddon, P. J., et. al. (1985) Cell 42, 93–104.
6. Maddon, P. J., et. al. (1987) Proc. Natl. Acad. Sci. U.S.A. 84, 9155–9159.
7. Richardson, N. E., et. al. (1988) Proc. Natl. Acad. Sci. U.S.A. 85, 6102–6106.
8. Chao, B. H., et. al. (1989) J. Biol. Chem. 264, 5812–5817.
9. Arthos, J., et. al. (1989) Cell 57, 469–481.
10. Wang, J., et. al. (1990) Nature 348, 411–418.
11. Ryu, S. -E., et. al. (1990) Nature 348, 419–426.
12. Leonard, C. K., et. al. (1990) J. Biol. Chem. 265, 10373–10382.
13. Earl, P. L., et. al. (1990) Proc. Natl. Acad. Sci. U.S.A. 87, 648–652.
14. Helseth, E., et. al. (1991) J. Virol. 65, 2119–2123.
15. Bolognesi, D. P. (1990) TIBTech 8, 40–45.
16. Olshevsky, U., et. al. (1990) J. Virol. 64, 5701–5707.
17. Steimer, K. S., et. al. (1991) AIDS 5, S135–143.
18. Wyatt, R., et. al. (1992) J. Virol. 66, 6997–7004.
19. Zolla-Pazner, S., et. al. (1992) Sem. in Virology 3, 203–211.
20. Steimer, K. S., et. al. (1991) Science 254, 105–108.
21. Pollard, S. R., et. al. (1992) EMBO J. 11, 585–591.
22. Okayama, H. (1983) Mol. Cell. Biol. 3, 280–289.
23. Maniatis, T., et. al. (1990) Molecular Cloning, Vol. 1–3.
24. Thomsen, D. R., et. al. (1984) Proc. Natl. Acad. Sci. U.S.A. 81, 659–663.
25. Pennica, D., et. al. (1983) Nature 301, 214–221.
26. Wain-Hobson, S., et. al. (1985) Cell 40, 9–17.
27. Koyanagi, Y. (1987) Science 236, 819–822.
28. Reed, L. J. (1938) Am. J. Hyg., 27, 493–497.
29. Cohn, E. J. et al., (1944) J. Clin. Invest. 23, 417–432.
30. Shiow-Her, C., et al. (1992) J. of Cellular Biochem., Supplement 16E, Abstrtact Q105.

---

What is claimed is:

1. A recombinant nucleic acid molecule which encodes a mutant HIV-1 gp120 envelope glycoprotein comprising a V3 loop deletion and a C4 domain$_{(W \rightarrow X)}$ point mutation, wherein X is an amino acid residue other than tryptophan.

2. The recombinant nucleic acid molecule of claim 1, wherein X is a valine residue.

3. The recombinant nucleic acid molecule of claim 1, wherein the nucleic acid molecule is a DNA molecule.

4. The recombinant nucleic acid molecule of claim 3, wherein the DNA molecule is a plasmid.

5. The recombinant nucleic acid molecule of claim 4, wherein the plasmid comprises the sequence of the plasmid designated PPI4-tPA.

6. The recombinant nucleic acid molecule of claim 1, wherein the C4 domain is an HIV-1$_{LAI}$ gp120 envelope glycoprotein C4 domain.

7. The recombinant nucleic acid molecule of claim 6, wherein the mutant HIV-1 gp120 envelope glycoprotein is a mutant HIV-1$_{LAI}$ gp120 envelope glycoprotein.

8. The recombinant nucleic acid molecule of claim 1, wherein the C4 domain is an HIV-1$_{JR-FL}$ gp120 envelope glycoprotein C4 domain.

9. The recombinant nucleic acid molecule of claim 8, wherein the mutant HIV-1 gp120 envelope glycoprotein is a mutant HIV-1$_{JR-FL}$ gp120 envelope glycoprotein.

\* \* \* \* \*